(12) United States Patent
Gao et al.

(10) Patent No.: US 11,312,710 B2
(45) Date of Patent: Apr. 26, 2022

(54) COMPOUND AND ORGANIC LIGHT-EMITTING DISPLAY DEVICE

(71) Applicant: SHANGHAI TIANMA AM-OLED CO., LTD., Shanghai (CN)

(72) Inventors: Wei Gao, Shanghai (CN); Xiangcheng Wang, Shanghai (CN); Lei Zhang, Shanghai (CN); Jinghua Niu, Shanghai (CN); Ying Liu, Shanghai (CN); Dongyang Deng, Shanghai (CN); Xueqiang Luo, Shanghai (CN); Ping An, Shanghai (CN); Gaojun Huang, Shanghai (CN)

(73) Assignee: SHANGHAI TIANMA AM-OLED CO., LTD., Shanghai (CN)

( * ) Notice: Subject to any disclaimer, the term of this patent is extended or adjusted under 35 U.S.C. 154(b) by 506 days.

(21) Appl. No.: 16/239,546

(22) Filed: Jan. 4, 2019

(65) Prior Publication Data

US 2019/0135797 A1     May 9, 2019

(30) Foreign Application Priority Data

Jul. 27, 2018    (CN) .......................... 201810847531.2

(51) Int. Cl.
*H01L 51/00*      (2006.01)
*C07D 409/14*      (2006.01)
(Continued)

(52) U.S. Cl.
CPC ......... *C07D 409/14* (2013.01); *C07D 405/14* (2013.01); *C07D 413/14* (2013.01);
(Continued)

(58) Field of Classification Search
None
See application file for complete search history.

(56) References Cited

U.S. PATENT DOCUMENTS 9,373,794 B2*   6/2016   Lee ..................... H01L 51/0072
2007/0270595 A1*   11/2007   Kim .................... H01L 51/0052
                                                548/469
(Continued)

FOREIGN PATENT DOCUMENTS

CN     103764786 A     4/2014
CN     107311979 A     11/2017
(Continued)

OTHER PUBLICATIONS

Seo et al. "Synthesis of novel benzothiophene derivative as a host material for blue phosphorescent organic light-emitting diodes." Dyes and Pigments 136 (2017): 145-149. (Year: 2017).*
(Continued)

*Primary Examiner* — Robert S Loewe
(74) *Attorney, Agent, or Firm* — Kilpatrick Townsend & Stockton, LLP

(57) ABSTRACT

The present disclosure provides a compound having property of thermally activated delayed fluorescence (TADF) and a display device. The compound has a structure represented by Formula (I), in which X is S, O, Se, or C; D is an electron donor, A is an electron acceptor; m is a number of the electron donor D, and the m electron donors D are the same or different; n is a number of the electron acceptor, and the n electron acceptors are the same or different, m and n are integers each independently selected from 1, 2, 3, 4 or 5, and m+n≤6. The above compound provides a high luminescence efficiency. The organic light-emitting display device has advantages of improved luminescence efficiency, lower cost and long service life by using the above compound as a light-emitting material, a host material, or a guest material.

(Continued)

(I)

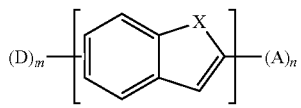

Formula (I)

16 Claims, 3 Drawing Sheets

(51) Int. Cl.
  *C07D 405/14* (2006.01)
  *C07D 471/10* (2006.01)
  *H01L 51/50* (2006.01)
  *C07D 413/14* (2006.01)

(52) U.S. Cl.
  CPC ........ C07D 471/10 (2013.01); H01L 51/0067 (2013.01); H01L 51/0072 (2013.01); H01L 51/0073 (2013.01); H01L 51/0074 (2013.01); H01L 51/5016 (2013.01); H01L 51/5092 (2013.01); H01L 51/5096 (2013.01); *H01L 51/001* (2013.01); *H01L 51/0037* (2013.01); *H01L 51/0042* (2013.01); *H01L 51/0061* (2013.01); *H01L 51/0094* (2013.01); *H01L 51/5012* (2013.01); *H01L 51/5056* (2013.01); *H01L 51/5072* (2013.01); *H01L 2251/308* (2013.01); *H01L 2251/552* (2013.01)

(56) References Cited

U.S. PATENT DOCUMENTS

| | | | | |
|---|---|---|---|---|
| 2015/0171342 A1* | 6/2015 | Jung | ............... | C07D 405/14 257/40 |
| 2015/0303384 A1* | 10/2015 | Kim | ............... | H01L 51/0052 257/40 |
| 2015/0311451 A1* | 10/2015 | Kim | ............... | H01L 51/0072 257/40 |
| 2016/0111650 A1* | 4/2016 | Noh | ............... | H01L 51/0052 257/40 |
| 2017/0244049 A1* | 8/2017 | Aspuru-Guzik | ..... | C07D 209/88 |
| 2017/0320855 A1* | 11/2017 | Wong | ............... | C07D 403/06 |
| 2018/0212158 A1* | 7/2018 | Aspuru-Guzik | ..... | C07D 519/00 |
| 2019/0027693 A1* | 1/2019 | Zysman-Colman | ......... | H01L 51/5016 |
| 2020/0013962 A1* | 1/2020 | Miyazaki | ............ | H01L 51/0068 |
| 2020/0020867 A1* | 1/2020 | Lin | ............... | C07D 403/14 |

FOREIGN PATENT DOCUMENTS

| | | | | |
|---|---|---|---|---|
| EP | 2878599 A1 | 6/2015 | | |
| JP | 2011046851 A | * | 10/2011 | ............. C09K 11/06 |
| JP | 2012089777 A | | 5/2012 | |
| KR | 20110120078 A | | 11/2011 | |
| KR | 20150116337 A | | 10/2015 | |
| KR | 2016027940 | * | 3/2016 | ............. C09K 11/06 |
| KR | 2016057018 | * | 5/2016 | ........... C07D 333/10 |
| WO | 2017104994 A1 | | 6/2017 | |

OTHER PUBLICATIONS

Lin et al. "Geometrical effect of stilbene on the performance of organic dye-sensitized solar cells." Journal of Materials Chemistry 21, No. 38 (2011): 14907-14916. (Year: 2011).*

Mishra et al. "Ruthenium-Catalyzed Direct and Selective C—H CYanation of N-(Hetero)aryl-7-azaindoles" J. Org. Chem. 2016, 81, 6525-6534. (Year: 2016).*

Tavadyan et al. "Antioxidant Properties of Selenophene, THiophene and Their Aminocarbonitrile Derivative" Antioxidants, 2017, 6, 22. (Year: 2017).*

Office Action of Chinese Patent Application No. 201810847531.2 dated Dec. 30, 2019.

Chinh T. Bui et al; "Solid-Phase Synthesis of 2,3-Disubstituted Benzo[b]thiophenes and Benzo[b]selenophenes"; Iliad Chemicals Pty Ltd, c/o The Department of Chemistry, La Trobe University, Bundoora, Victoria 3086, Austraiia.

* cited by examiner (I)

COMPOUND AND ORGANIC LIGHT-EMITTING DISPLAY DEVICE

CROSS-REFERENCE TO RELATED APPLICATIONS

The present disclosure claims priority to Chinese Patent Application No. 201810847531.2, filed on Jul. 27, 2018, the content of which is incorporated herein by reference in its entirety.

FIELD

The present disclosure relates to the field of organic electroluminescent materials, and in particular to a material having thermally activated delayed fluorescence (TADF) properties and its use in an organic light-emitting display device.

BACKGROUND

With the rapid development of electronic display technology. Organic Light-emitting Diode (OLED) is widely used in various display devices, and research on light-emitting materials of OLED is also more intensive.

Based on light-emitting mechanism, materials applicable in a light-emitting layer of the OLED can be mainly divided into four types:

(1) fluorescent materials; (2) phosphorescent materials; (3) triplet-triplet annihilation (TTA) materials; (4) thermally activated delayed fluorescence (TADF) materials.

As regards the fluorescent materials, according to spin-statistics, a ratio of singlet excitons to triplet excitons is 1:3, and thus the maximum internal quantum yield of fluorescent materials does not exceed 25%. According to the Lambertian luminescence mode, the light extraction efficiency is about 20%, and thus an external quantum efficiency (EQE) of the OLED device based on the fluorescent material does not exceed 5%.

With respect to the phosphorescent materials, an intersystem crossing of molecules can be enhanced due to a heavy atom effect of the phosphorescent materials, and 75% of triplet excitons can be directly utilized to complete emission involving both S1 and T1 at room temperature, where a theoretical maximum internal quantum yield can reach 100%. According to the Lambertian luminescence mode, a light extraction efficiency is about 20%, and thus the EQE of the OLED device based on the phosphorescent materials can reach 20%. However, the phosphorescent materials are basically complexes of a heavy metal such as Ir, Pt, Os, Re, Ru, etc., and are unsuitable for a large-scale production due to the high production cost. Under a high electric current density, a substantial efficiency fall can be observed in the phosphorescent materials, which lead to a deterioration of the stability of the phosphorescent devices.

As regards TAA materials, two adjacent triplet excitons are combined to form a singlet excited state molecule with higher energy level and a ground state molecule. However, since the two triplet excitons merely produce one singlet state exciton, the theoretical maximum internal quantum yield can only reach 62.5%. In order to prevent the substantial fall of efficiency, a concentration of triplet excitons should be regulated during this process.

For the TADF materials, when an energy level difference between the singlet excited state and the triplet excited state is relatively small, a reverse intersystem crossing (RISC) may occur among the molecules, and the excitons are converted from T1 state to S1 state by absorbing the ambient heat, so that 75% of triplet excitons and 25% of singlet excitons can be utilized at the same time. In this way, the theoretical maximum internal quantum yield can reach 100%. The TADF materials are mainly organic compounds without rare metal element, so that the production cost is relatively low. The TADF materials can be chemically modified by various methods. However, there are few TADF materials that have been discovered so far, and it is urgent to develop new TADF materials applicable in OLED devices.

SUMMARY

The present disclosure aims to provide a novel electroluminescent compound having a property of thermally activated delayed fluorescence (TADF).

The compound having the TADF property according to the present disclosure has a chemical structure represented by the formula (I):

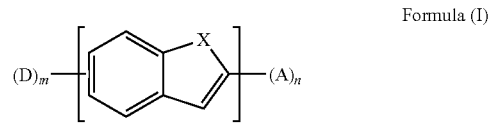

Formula (I)

in which X is S, O, Se, or C;

D is a chemical group acting as an electron donor, A is a chemical group acting as an electron acceptor, m is a number of the electron donor D, and the m electron donors D are the same or different from one another, n is a number of the electron acceptor A, the n electron acceptors A are the same or different from one another.

m and n are integers each independently selected from 1, 2, 3, 4 or 5, and $m+n \leq 6$.

DESCRIPTION OF EMBODIMENTS

Figure 1:
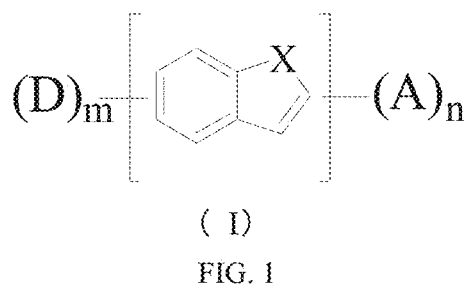
FIG. 1 is a general formula of a compound having a property of thermally activated delayed fluorescence according to the present disclosure.

The present disclosure is further described by the following embodiments.

In one embodiment of the present disclosure provides a compound having TADF property, and the compound has a structure represented by formula (I):

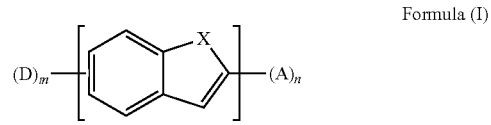

Formula (I)

in which X is S, O, Se, or C:

D is a chemical group acting as an electron donor, A is a chemical group acting as an electron acceptor, m is a number of the electron donor D, and the m electron donors D are the same or different from one another, n is a number of the electron acceptor A, the n acceptors A are the same or different from one another, m and n are integers each independently selected from 1, 2, 3, 4 or 5, and m+n≤6.

It should be noted that in Formula (I), the electron donor D can be bonded either to the benzene ring or to the five-membered heterocyclic ring. Likewise, the electron donor A can be bonded either to the benzene ring or to the five-membered heterocyclic ring.

In the compound according to an embodiment of the present disclosure, the electron donor D is any one of following chemical groups:

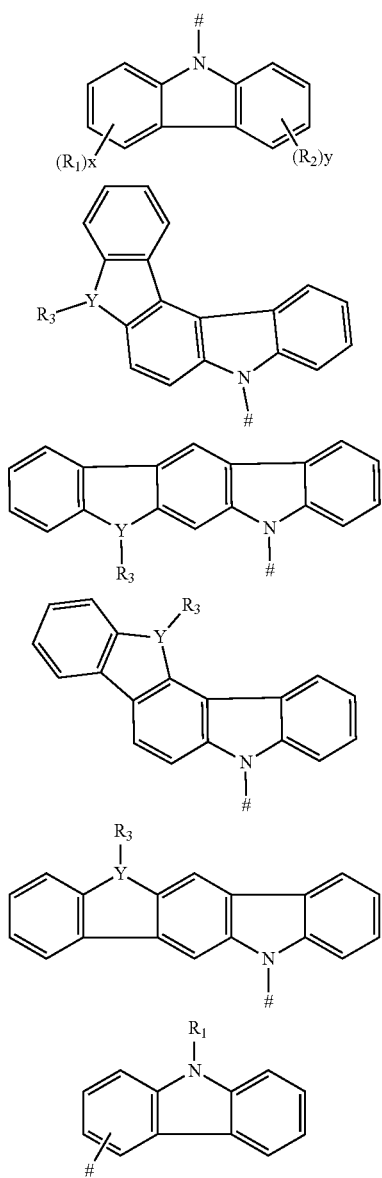

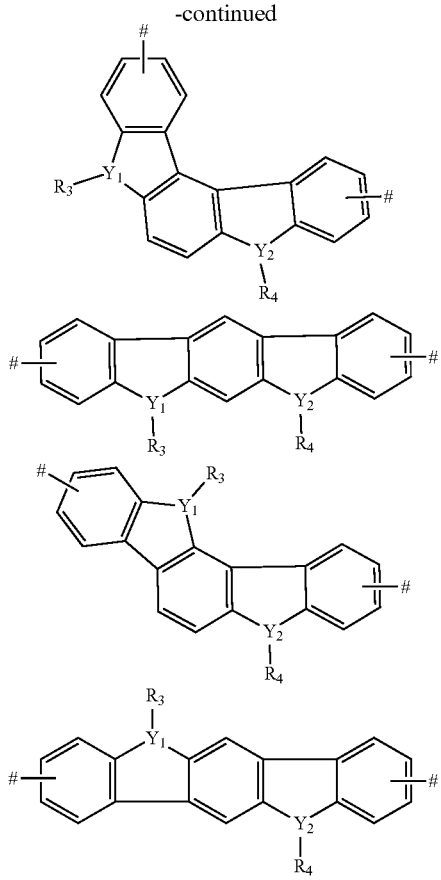

in which Y, $Y_1$ and $Y_2$ are each independently selected from a group consisting of carbon, nitrogen, oxygen, sulfur, and silicon;

x and y are integers each independently selected from 0, 1, 2 or 3:

# indicates a bonding position;

when Y is oxygen or sulfur, $R_3$ is absent;

when $Y_1$ is oxygen or sulfur, $R_3$ is absent;

when $Y_2$ is oxygen or sulfur, $R_4$ is absent; and $R_1$, $R_2$, $R_3$ and $R_4$ are each independently selected from a group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl and its derivative groups, substituted or unsubstituted C12-C40 diphenylamino and its derivative groups, substituted or unsubstituted C3-C40 azine group and its derivative groups, and groups represented by formula (21):

Formula (21)

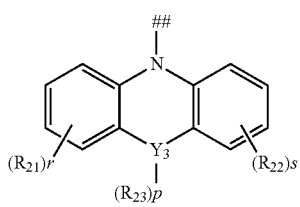

in which $Y_3$ is selected from a group consisting of carbon, nitrogen, oxygen, sulfur, and silicon;

$R_{21}$, $R_{22}$ and $R_{23}$ are each independently selected from a group consisting of hydrogen, C1-C20 alkyl, C1-C20 alkoxy, substituted or unsubstituted C6-C40 aryl, and substituted or unsubstituted C4-C40 heteroaryl;

r and s are integers each independently selected from 0, 1, 2 or 3, and p is 0, 1 or 2;

when $Y_3$ is oxygen or sulfur, p=0;

indicates a bonding position.

In the compound according to an embodiment of the present disclosure, the electron donor D is any one of following chemical groups:

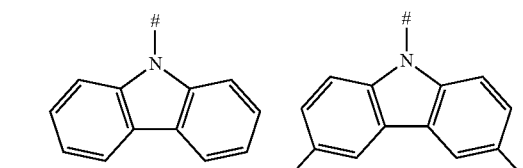
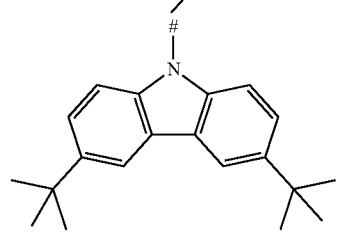
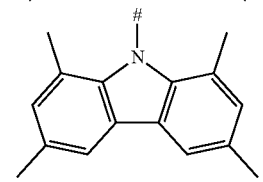
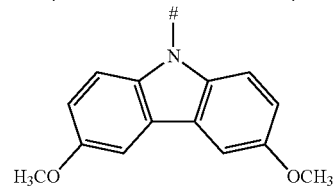
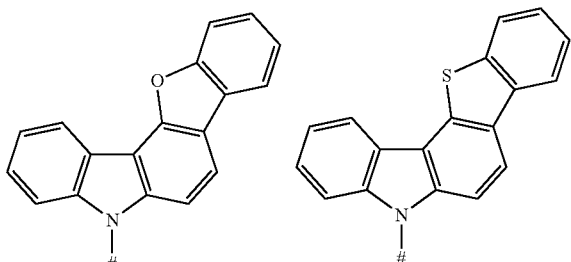
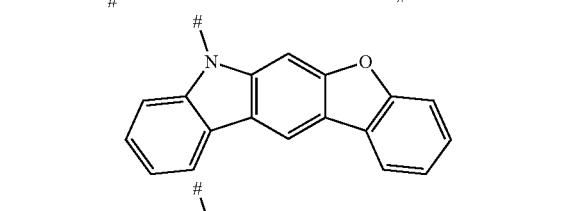
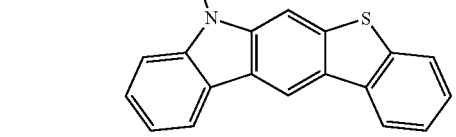

-continued

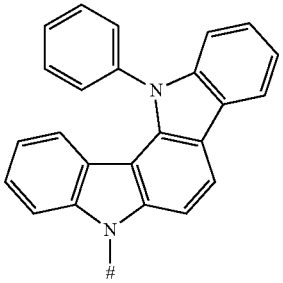
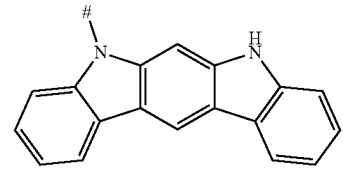
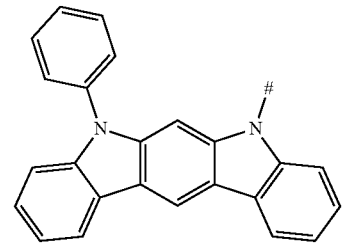
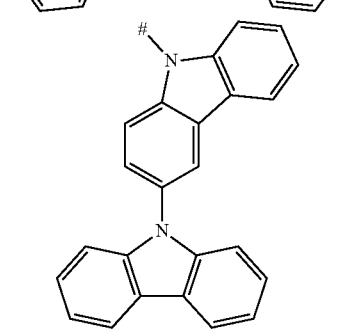
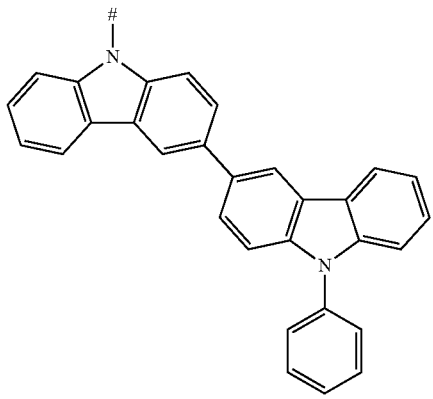
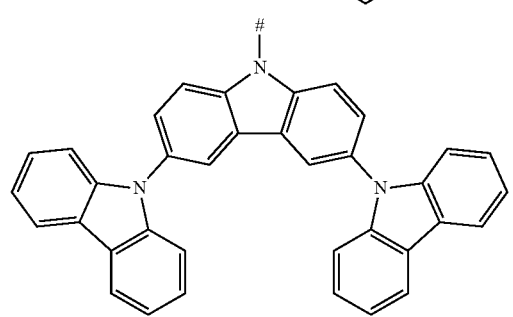

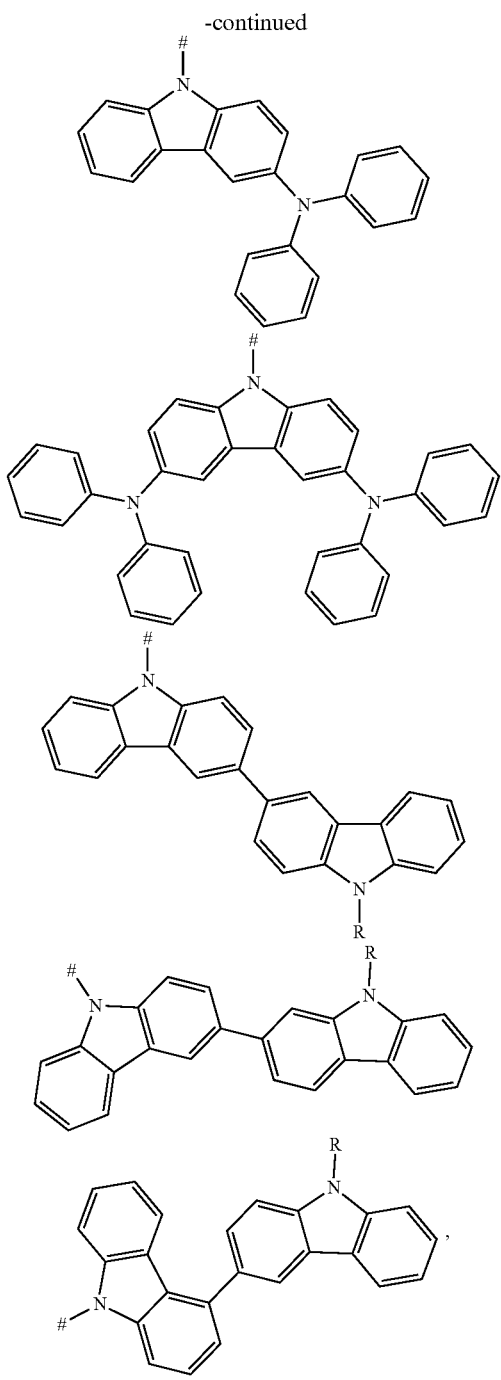

in which R is selected from a group consisting of C1-C20 alkyl, C1-C20 alkoxy, C2-C20 alkenyl, C2-C20 alkynyl, C6-C40 aryl, and C4-C40 heteroaryl; and indicates a bonding position.

In the embodiment of the compound according to the present disclosure, when the electron donor D is a carbazolyl and its derivative groups, the following advantages are obtained: (1) the raw material is inexpensive and of low cost; (2) It is easy to modify the molecular properties without changing a main backbone of molecule; (3) functional modifications can be easily made on the nitrogen atom; (4) multiple bonding positions on the carbazole group can be bonded to other molecular structures; (5) good heat stability and chemical stability; (6) high triplet energy level; and (7) excellent electron donating ability and luminescence performance, and excellent hole transmission property.

In the compound according to an embodiment of the present disclosure, the electron donor D is any one of following chemical groups:

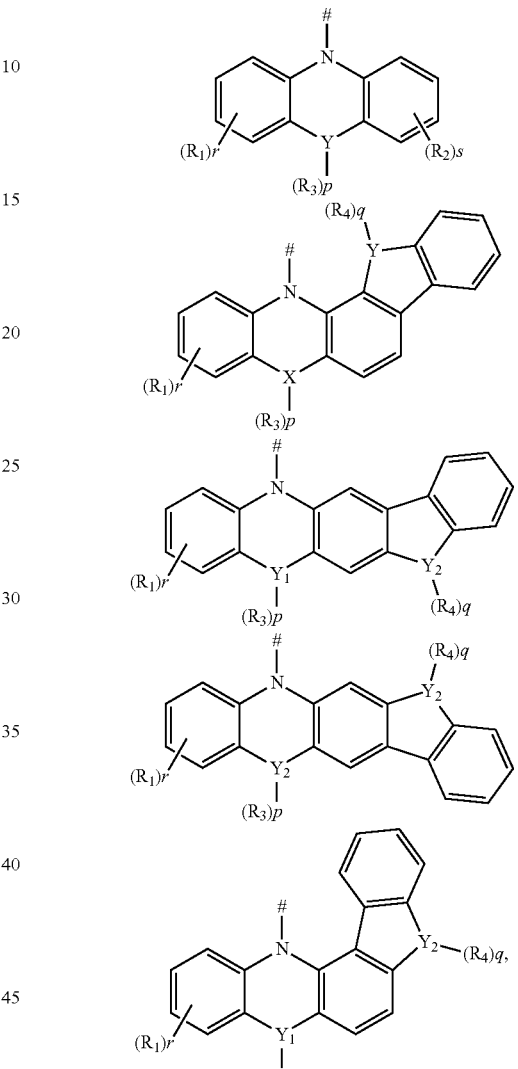

in which Y, $Y_1$ and $Y_2$ are each independently selected from a group consisting of carbon, nitrogen, oxygen, sulfur, and silicon;

# indicates a bonding position;

r and s are integers each independently selected from 0, 1, 2 or 3, and p and q are each independently 0, 1 or 2;

when Y is oxygen or sulfur, p=0 or q=0;

when Y is a nitrogen atom, p and q are each independently 0 or 1;

when Y is a carbon atom or a silicon atom, p and q are each independently 0, 1 or 2;

$R_1$, $R_2$, $R_3$ and $R_4$ are each independently selected from a group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl and its derivative groups, substituted or unsubstituted C12-C40 diphenylamino and its derivative groups, substituted or unsubstituted C3-C40 azine group and its derivative groups, and groups represented by formula (21):

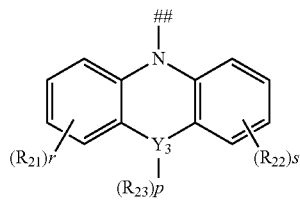

Formula (21)

in which $Y_3$ is selected from a group consisting of carbon atom, nitrogen atom, oxygen atom, sulfur atom or silicon atom;

$R_{21}$, $R_{22}$ and $R_{23}$ are each independently selected from a group consisting of hydrogen, C1-C20 alkyl, C1-C20 alkoxy, substituted or unsubstituted C6-C40 aryl, and substituted or unsubstituted C4-C40 heteroaryl;

r and s are integers each independently selected from 0, 1, 2 or 3, and p is 0, 1 or 2;

when $Y_3$ is oxygen or sulfur, p=0:

indicates a bonding position.

In the compound according to an embodiment of the present disclosure, the electron donor D is any one of following chemical groups:

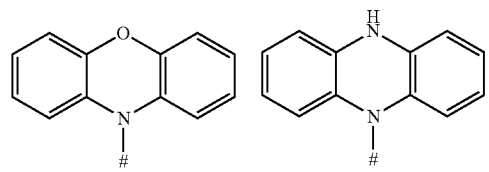

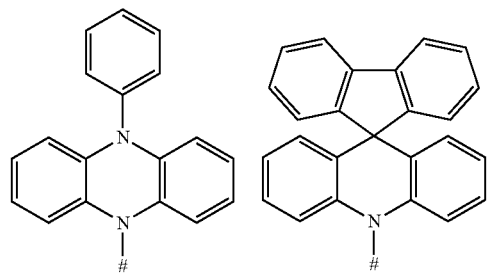

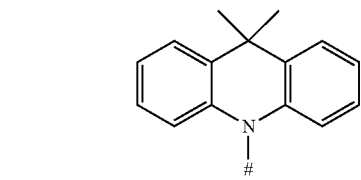

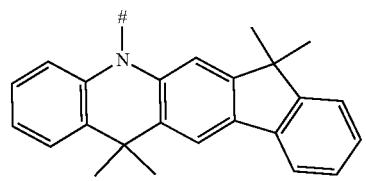

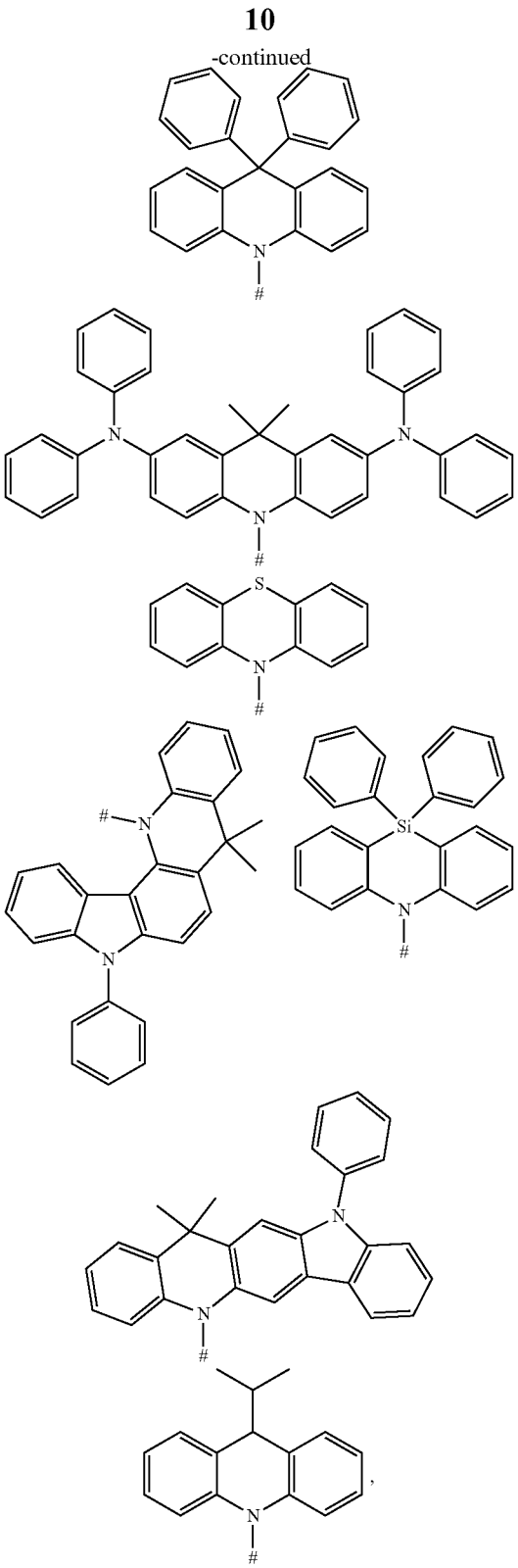

in which # indicates a bonding position.

In this embodiment of the compound according to the present disclosure, when the electron donor D is acridinyl and its derivative groups or other groups having similar structure, the following advantages are obtained: (1) very strong electron donating ability, shorter retarded fluorescence lifetime; (2) better separation of HOMO from LUMO;

(3) rigid molecular structure, which can effectively reduce a non-radiative decay of the excited state; (4) the rigid molecular structure also can inhibit free intramolecular rotation and vibration, which is conductive to improving a monochromaticity of the material and reducing a Full Width Half Maximum (FWHM) of the material; and (5) high triplet energy level.

In the compound according to an embodiment of the present disclosure, the electron donor D is any one of following chemical groups:

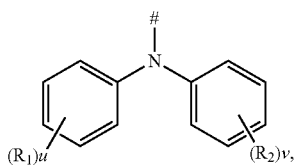

in which # indicates a bonding position;

u and v are integers each independently selected from 0, 1, 2 or 3;

R₁ and R₂ are each independently selected from a group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl and its derivative groups, substituted or unsubstituted C12-C40 diphenylamino and its derivative groups, substituted or unsubstituted C3-C40 azine group and its derivative groups, and groups represented by Formula (21):

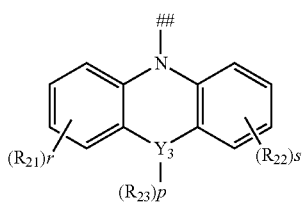

Formula (21)

in which Y₃ is selected from a group consisting of carbon atom, nitrogen atom, oxygen atom, sulfur atom, or silicon atom;

R₂₁, R₂₂ and R₂₃ are each independently selected from a group consisting of hydrogen, C1-C20 alkyl, C1-C20 alkoxy, substituted or unsubstituted C6-C40 aryl, or substituted or unsubstituted C4-C40 heteroaryl;

r and s are integers each independently selected from 0, 1, 2 or 3, and p is 0, 1 or 2;

when Y₃ is oxygen or sulfur, p=0; and indicates a bonding position.

In the compound according to an embodiment of the present disclosure, the electron donor D is any one of following chemical groups:

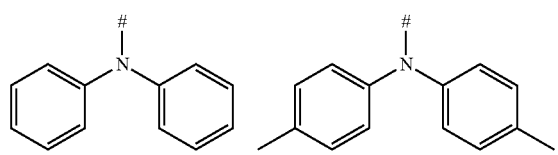

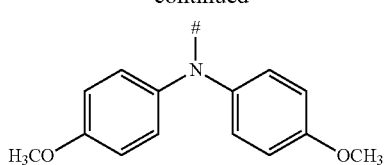

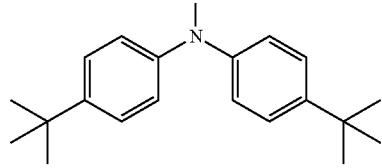

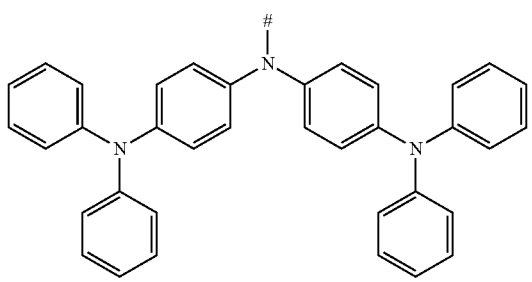

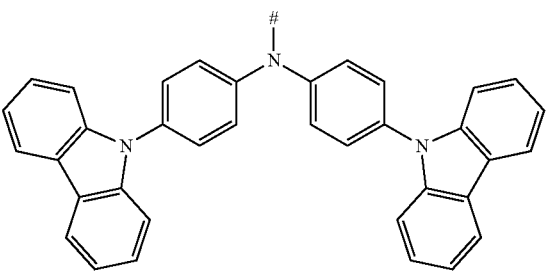

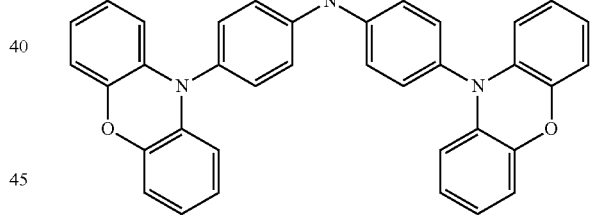

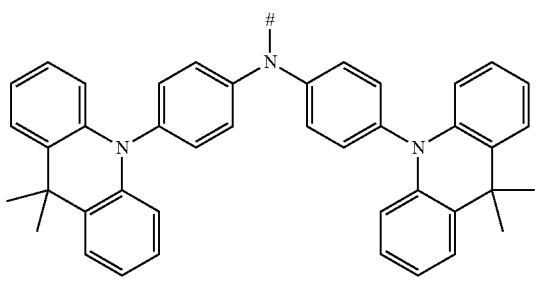

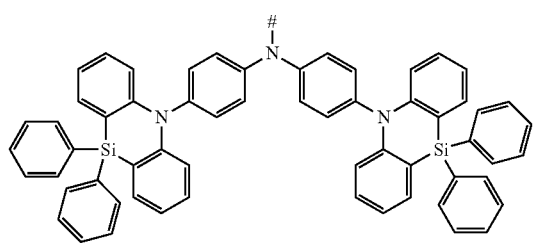

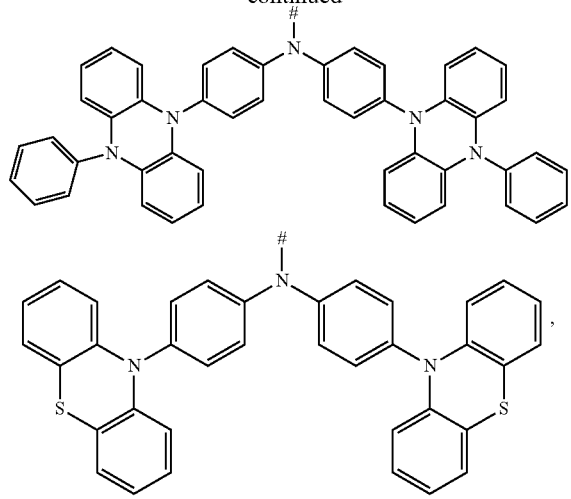

in which # indicates the bonding position.

In this embodiment of the present disclosure, when the electron donor D is a diphenylamino group and its derivative groups, the following advantages are obtained: (1) moderate electron donating ability; and (2) good heat stability and chemical stability, wide sources of raw material, low cost, easy to be chemically modified, and effective spatial separation of HOMO from LUMO.

According to another embodiment of the present disclosure, the electron donor D is any one of following chemical groups:

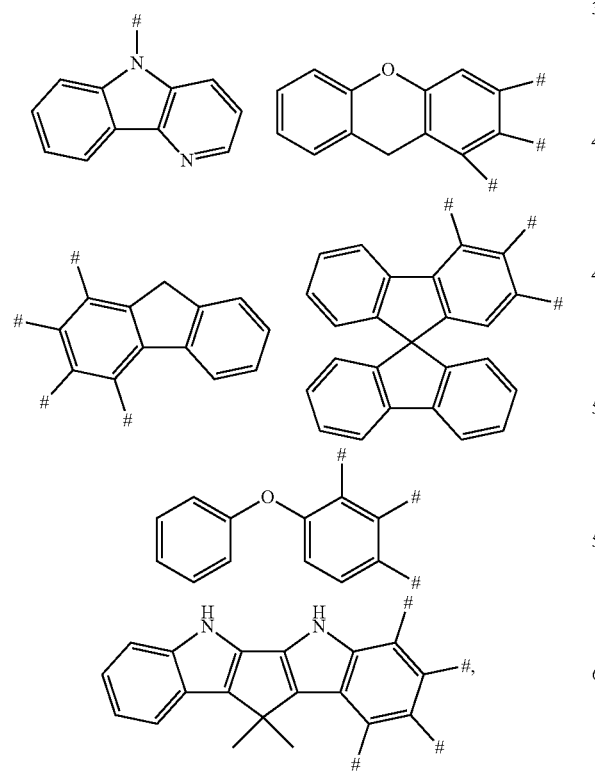

in which # indicates a bonding position. These compounds also have good electron donating ability.

According to an embodiment of to the present disclosure, the electron acceptor A is selected from a group consisting of nitrogenous heterocyclic substituent, cyano-containing substituent, triaryl boron substituent, benzophenone substituent, aromatic heterocyclic ketone substituent, and sulfone substituent.

According to an embodiment according to the present disclosure, the nitrogenous heterocyclic substituent is any one of following chemical groups:

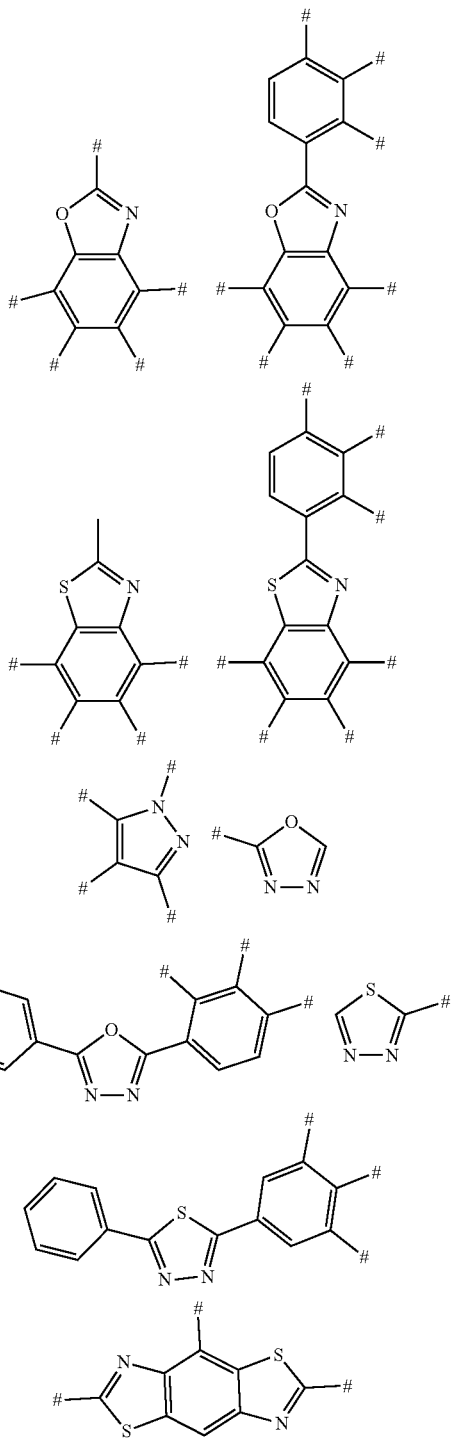

-continued
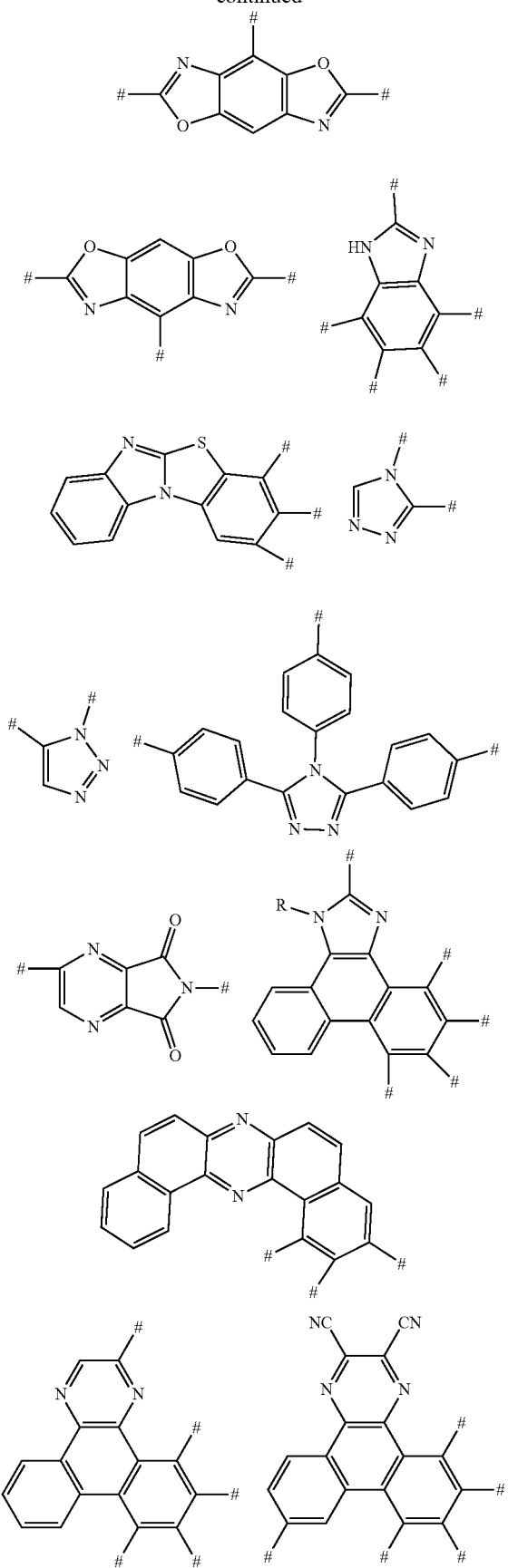
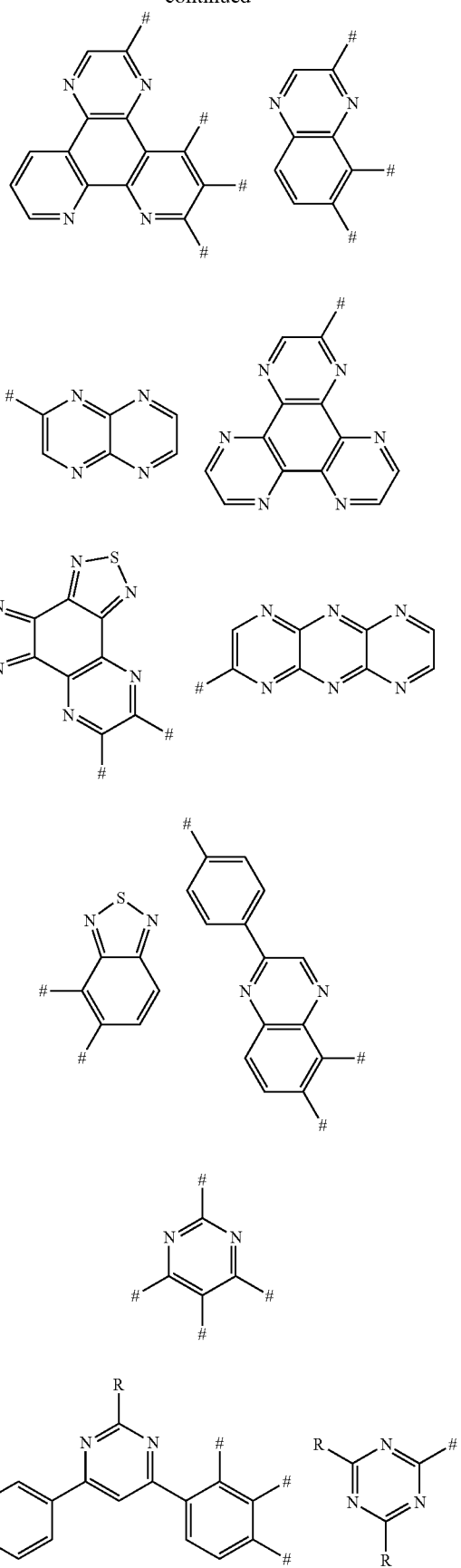

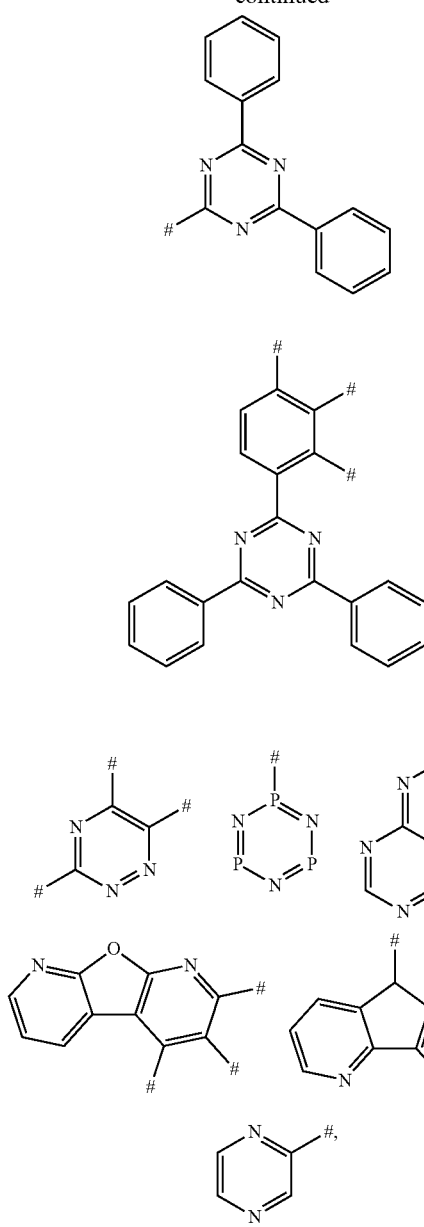

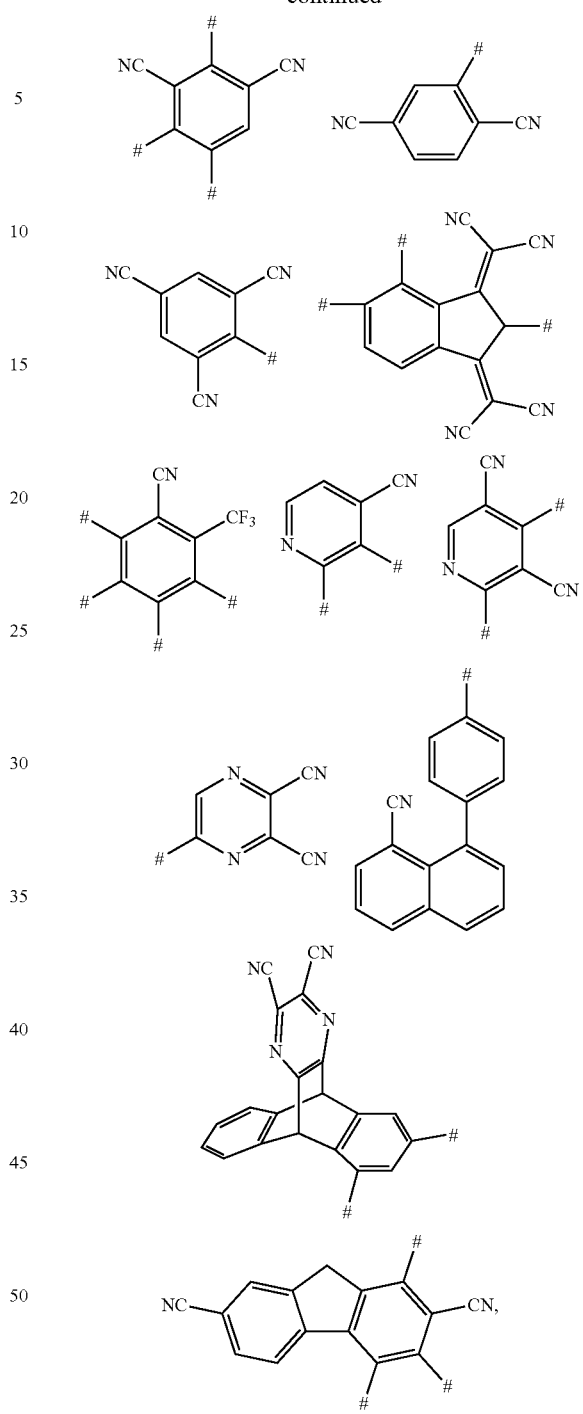

in which # indicates a bonding position;

R is selected from a group consisting of hydrogen, C1-C20 alkyl, C1-C20 alkoxy, C4-C8 cycloalkyl, C6-C40 aryl, and C4-C40 heteroaryl.

According to an embodiment of the present disclosure, the cyano-containing substituent is any one of following groups:

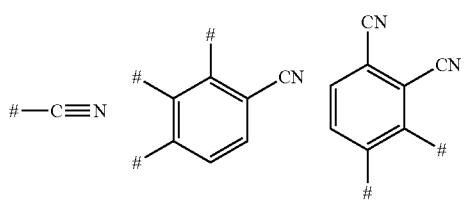

in which # indicates a bonding position.

In this embodiment of the present disclosure, the cyano-containing substituent has a very strong electron-withdrawing ability, so that a non-radiative transition can be effectively suppressed, thereby forming a D-A type TADF molecule with low $\Delta E_{ST}$ and high radiation transition rate constant kr.

In the compound according to another embodiment of the present disclosure, the triaryl boron substituent is any one of following groups:

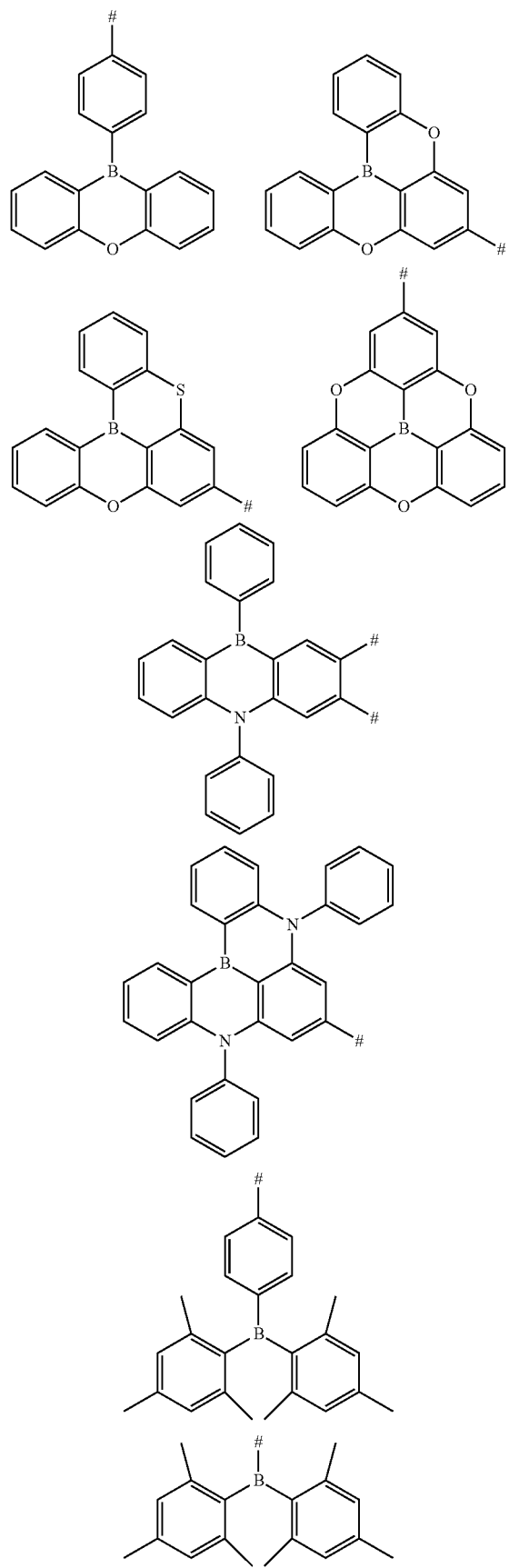

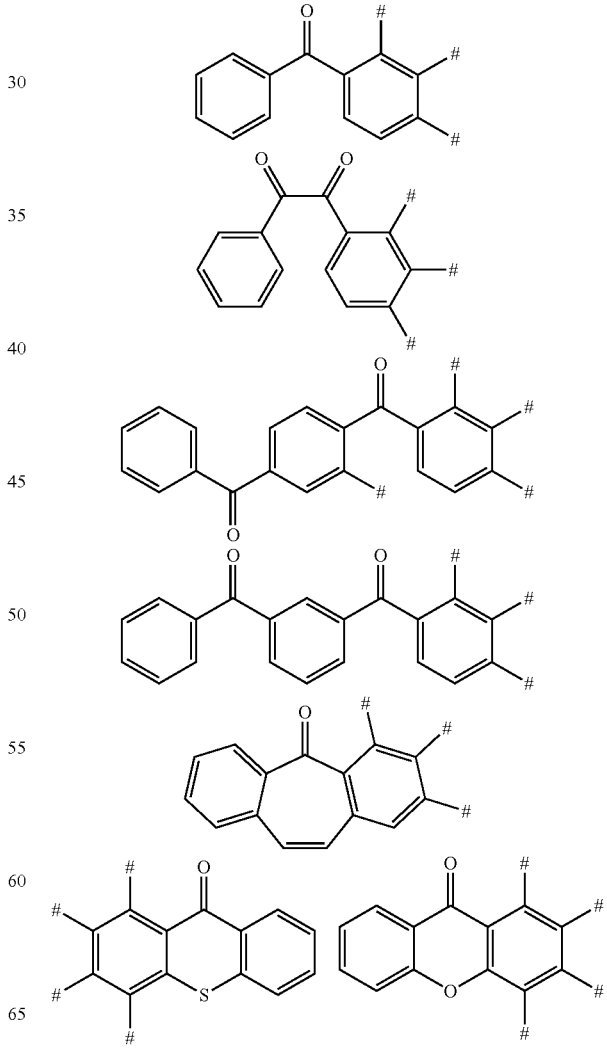

-continued in which # indicates the bonding position.

In this embodiment of the present disclosure, due to an empty p orbital of boron atom, when the aromatic ring is bonded to the boron atom, a conjugate plane can be provided, and the substituent on the aromatic ring protects the boron atom from being affected by oxygen and water. In this way, the group has better optical properties and can be used to synthesize triaryl derivatives. The obtained triaryl boron substituents can be used to form D-A type TADF materials.

According to still another embodiment of the present disclosure, the benzophenone substituent or the heterocyclic ketone substituent is any one of following chemical groups:

-continued

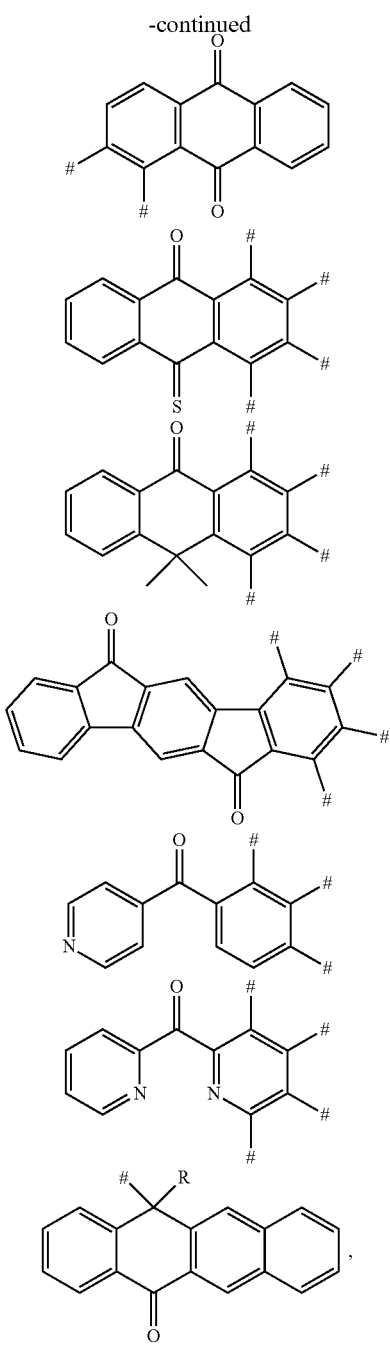

in which # indicates a bonding position;

R is selected from a group consisting of C1-C20 alkyl, C1-C20 alkoxy, C2-C20 alkenyl, C2-C20 alkynyl. C4-C8 cycloalkyl, C6-C40 aryl, and C4-C40 heteroaryl.

In such embodiment of the present disclosure, the benzophenone substituents or the heterocyclic ketone substituents contain an electron-deficient carbonyl group (C═O). The carbonyl group, as an electron acceptor, has a large angle with respect to the carbonyl group and the benzene ring. Therefore, the benzophenone substituents or the heterocyclic ketone substituents are pure organic phosphors with very efficient intersystem crossing (kISC=$10^{11} \cdot s^{-1}$), so that they are very suitable to be used as electron acceptor to form D-A type TADF molecules emitting blue light.

In the compound according to another embodiment of the present disclosure, the sulfone substituent is any one of following groups:

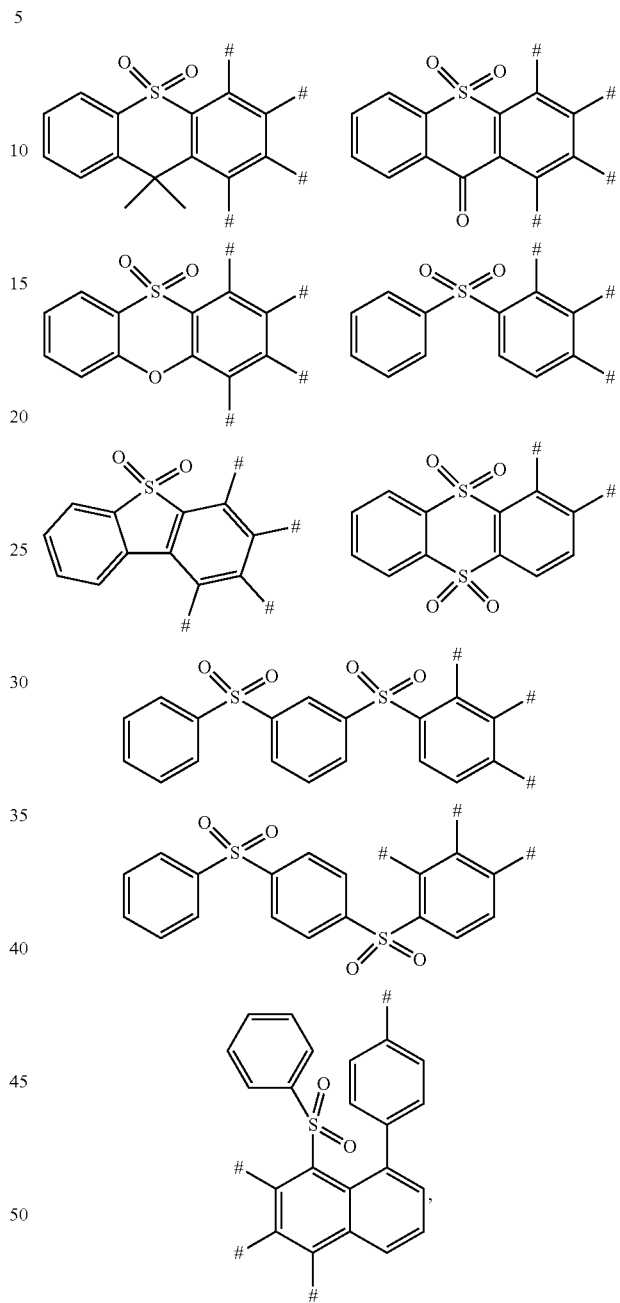

in which # indicates the bonding position.

In this embodiment of the compound according to the present disclosure, the sulfone substituent, as an electron acceptor, has good electron-withdrawing ability and has a certain torsion angle at the center of molecular to obtain a lower $\Delta E_{ST}$ value. Therefore, the sulfone substituent can be used as an electron acceptor to form D-A type TADF molecules.

In the compound according to another embodiment of the present disclosure, the electron acceptor A is any one of following groups:

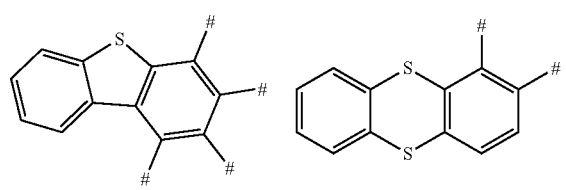
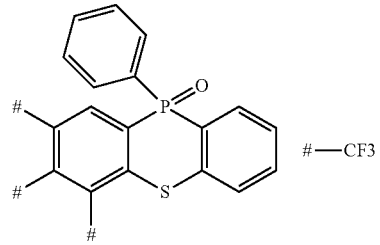
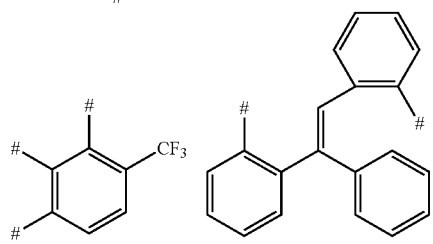
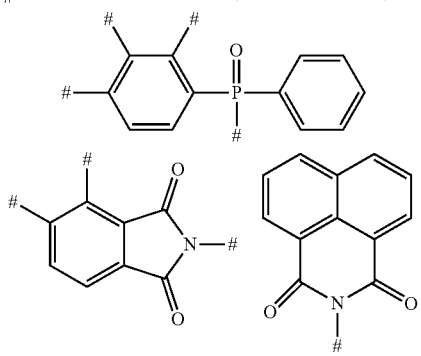
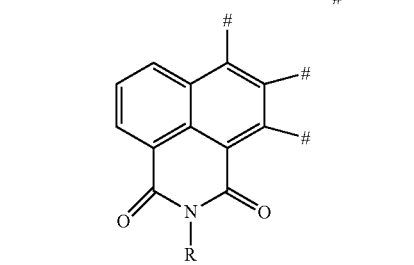
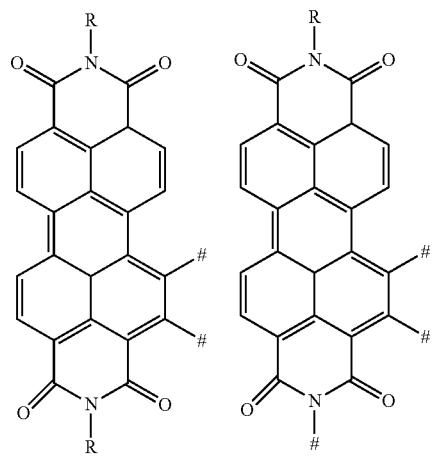
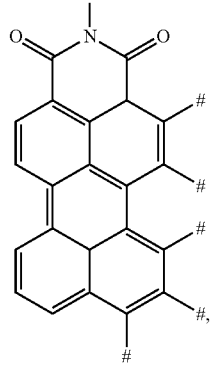
in which # indicates the bonding position,
R is selected from a group consisting of C1-C20 alkyl, C1-C20 alkoxy, C2-C20 alkenyl, C2-C20 alkynyl, C4-C8 cycloalkyl, C6-C40 aryl, and C4-C40 heteroaryl.
According to some embodiments according to the present disclosure, the compound according to the present disclosure is any one of following compounds:
P1
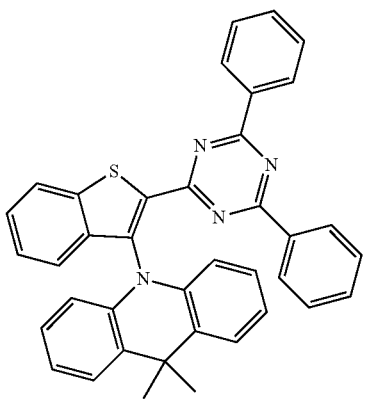
P2
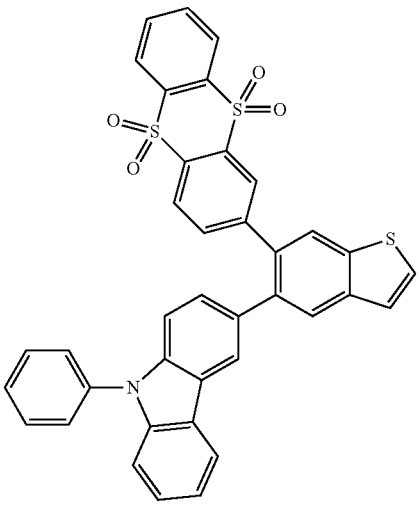

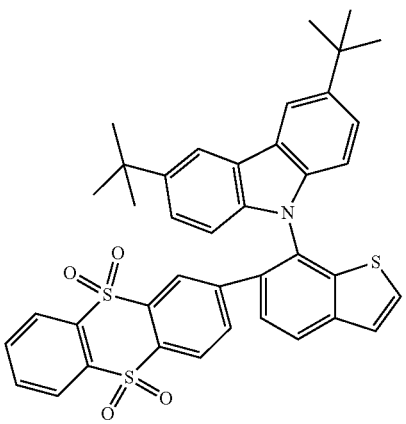
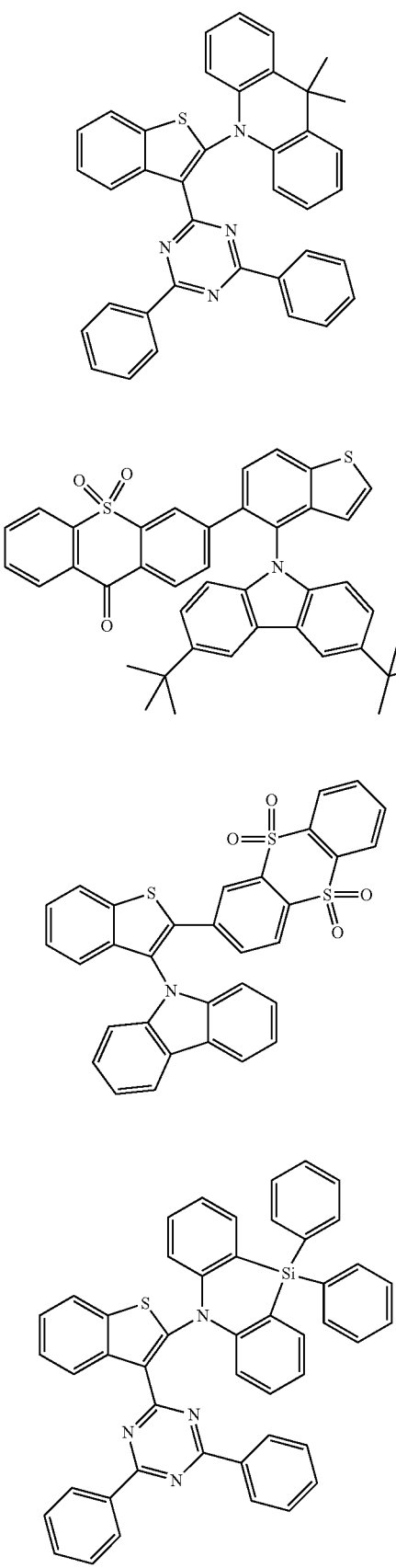

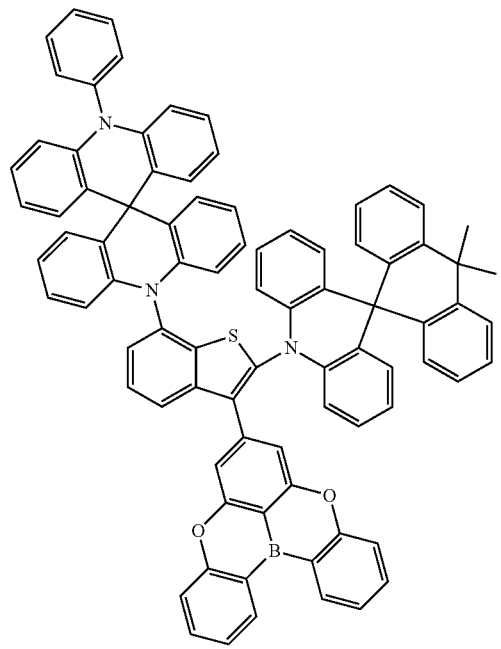
P15
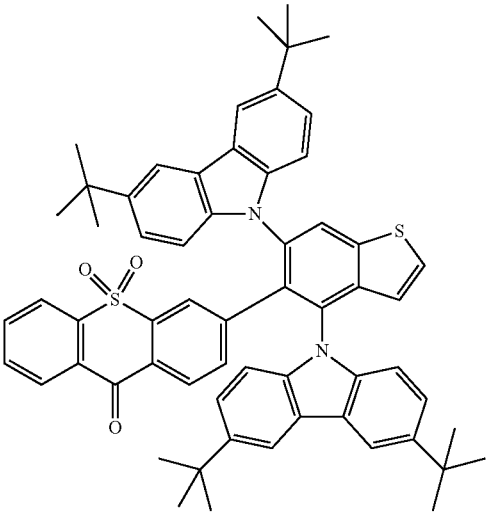
P13
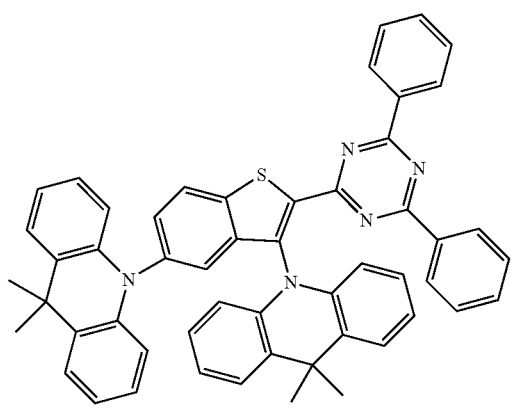
P11
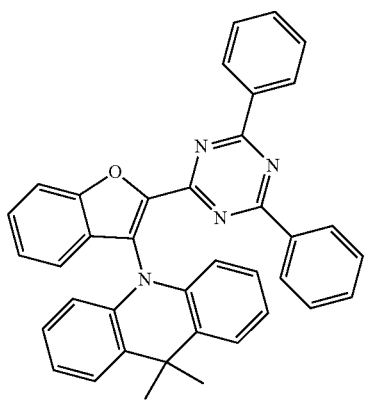
P16

P17
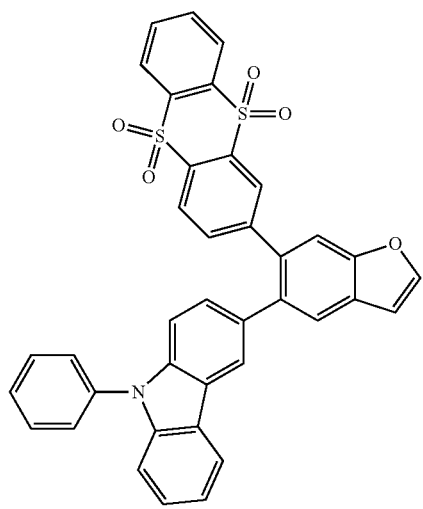
P18
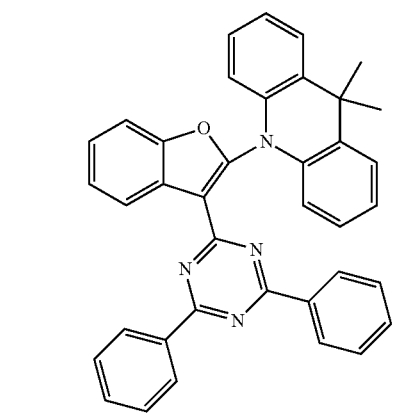
P19
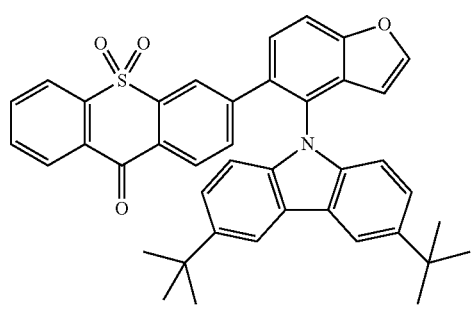
P20
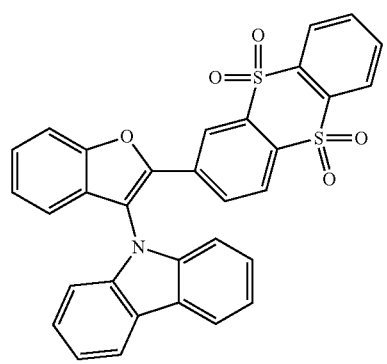
P21
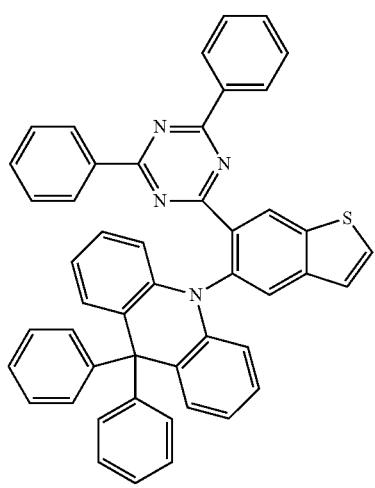
P22
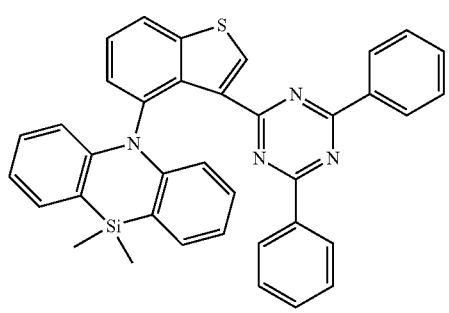
P23
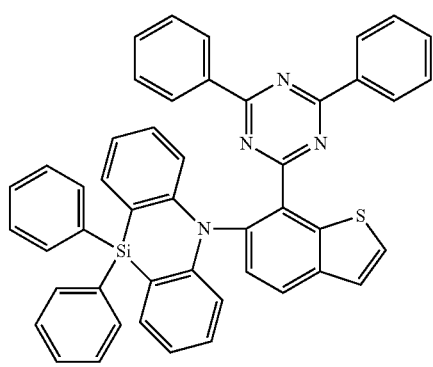
P24
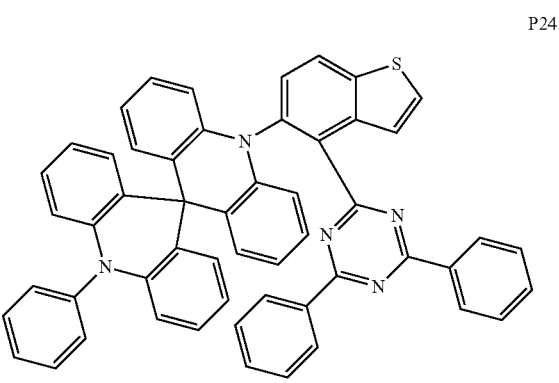

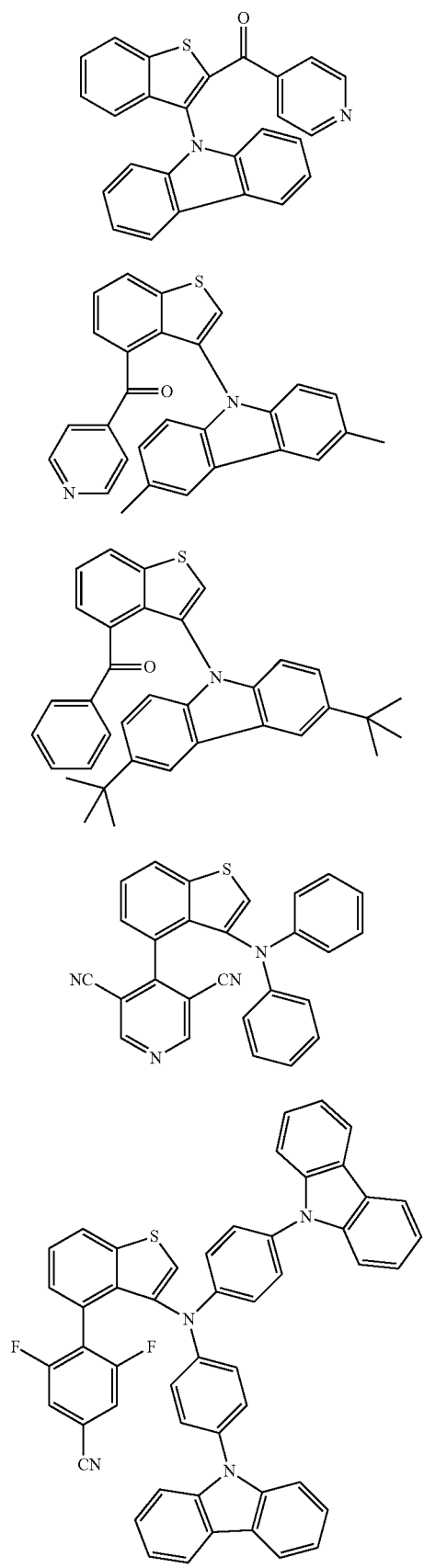
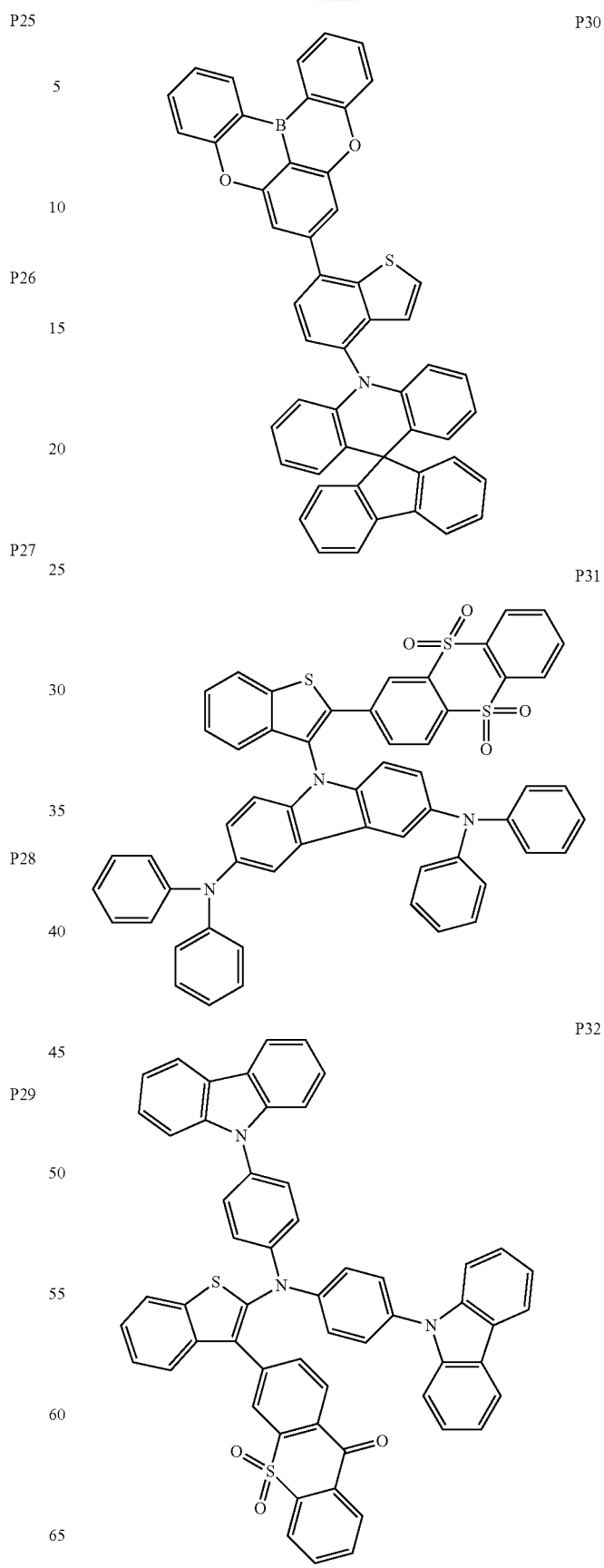

-continued
P33
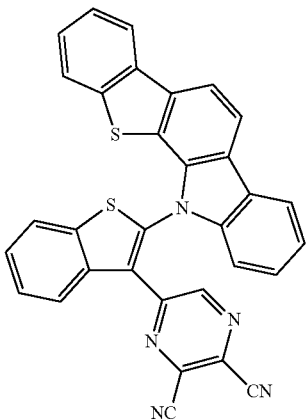
P34
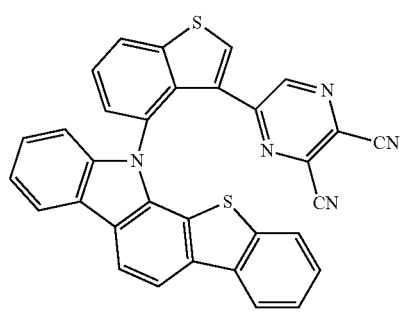
P35
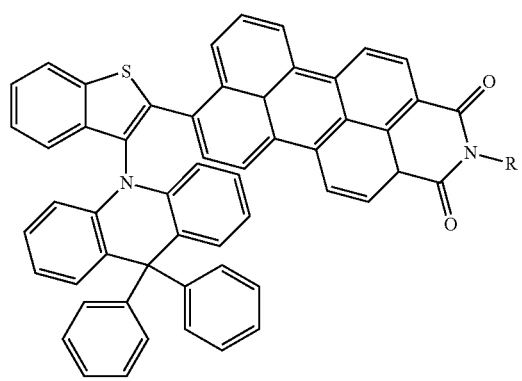
P37
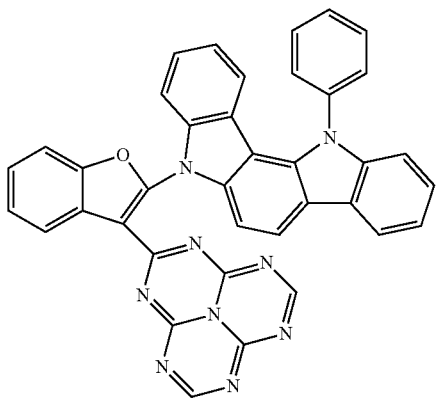
P38
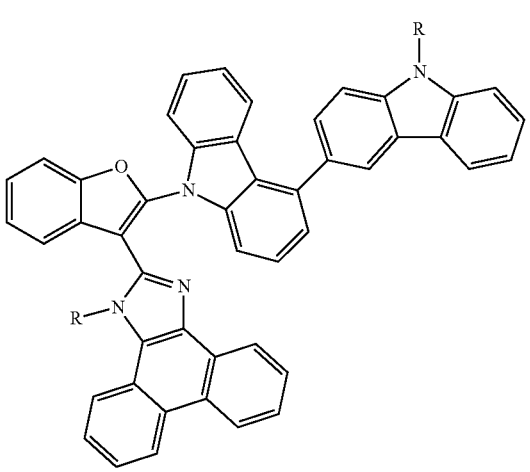
P39
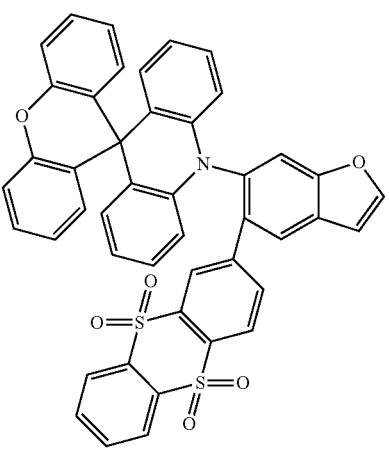
P36

P40
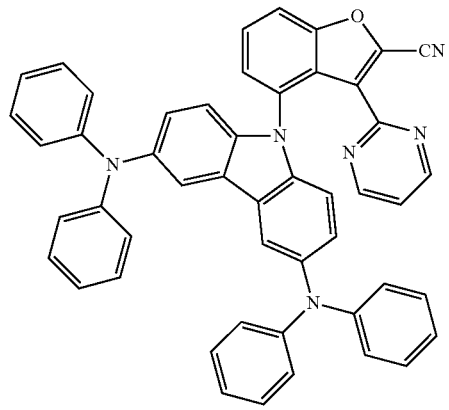
P41
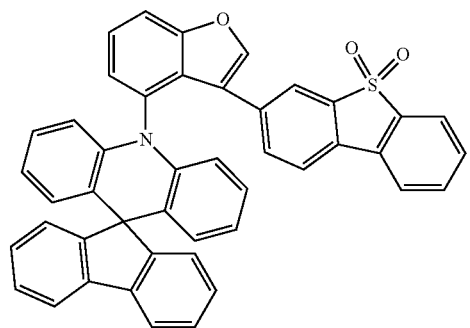
P42
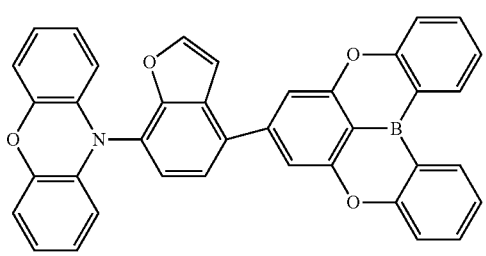
P43
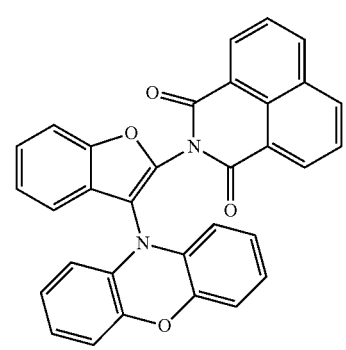
P44
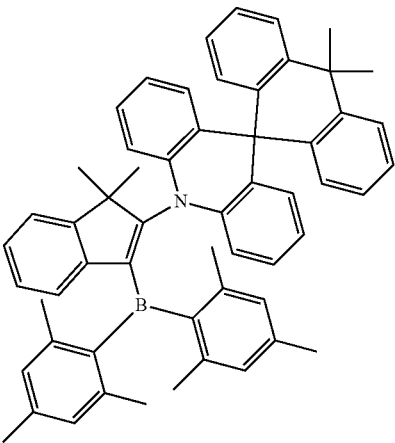
P45
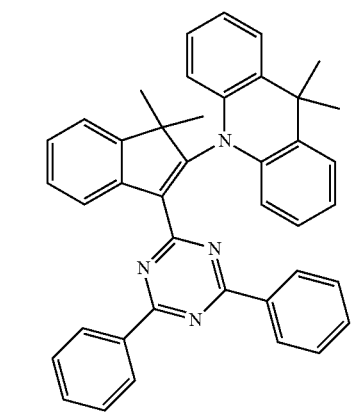
P46
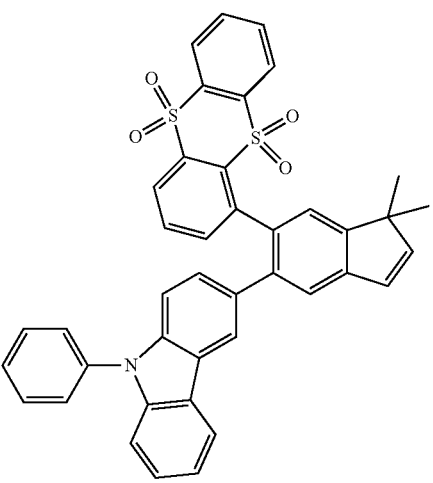

-continued

P47
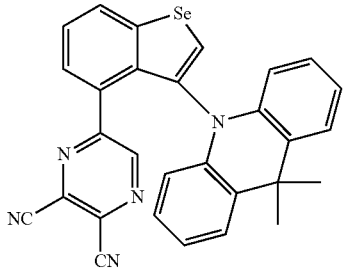

P48
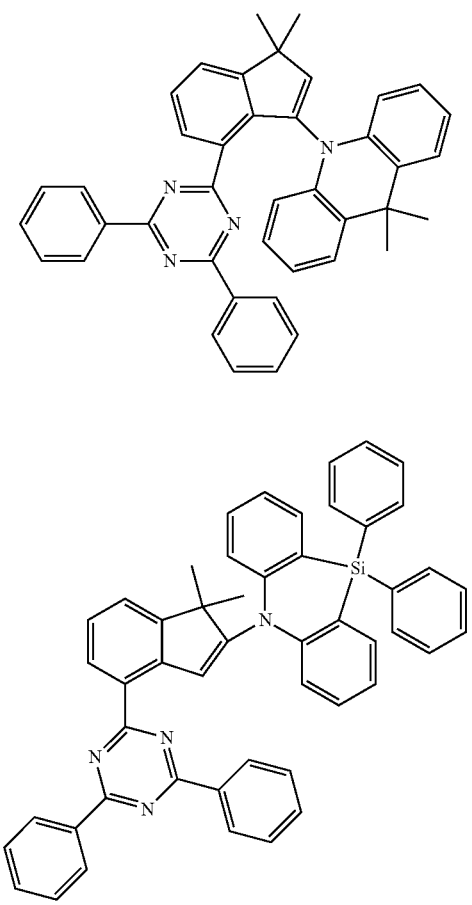

P49
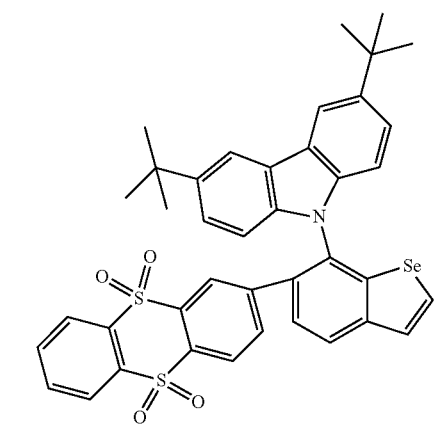

P50
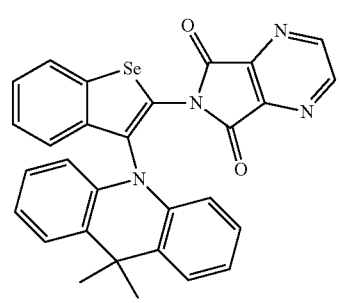

-continued

P51
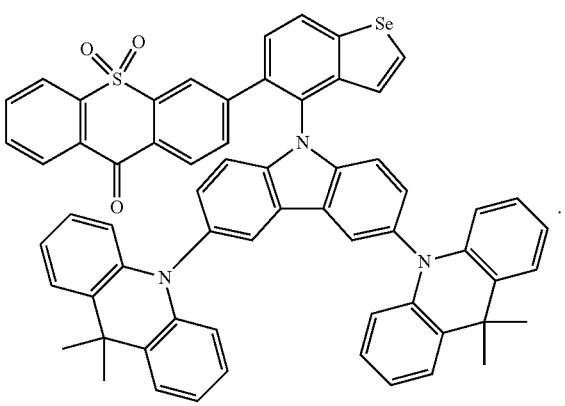

P52

In the compound according to the present disclosure, the electron donor D and the electron acceptor A are each independently bonded to the benzene ring and to the five-membered heterocyclic ring containing atom X in the Formula (I). The electron donor D and the electron acceptor A both can be bonded to the benzene ring or both can be bonded to the five-membered heterocyclic ring. In one embodiment, the electron donor D and the electron acceptor A are bonded to the compound represented by the Formula (I) in ortho-position. The ortho-position means that the electron donor D and the electron acceptor A are bonded to two adjacent carbon atoms of the compound represented by the Formula (I), no matter on the aromatic ring or on the five-membered heterocyclic ring. The ortho-position substitution has the following advantages: (1) more effective separation of HOMO from LUMO; (2) a larger dihedral angle between the electron donor D and electron acceptor A, which leads to a large steric hindrance between the electron donor D and the electron acceptor A and thus results in a smaller $\Delta E_{st}$ and (3) an increased intramolecular spatial restriction, which reduces the positive solvation color change effect, and at the same time, improves excitation purity and reduces the half peak width.

Preferably, in the compound according to the present disclosure, an energy difference $\Delta E_{st}$ between a lowest singlet energy level S1 and a lowest triplet energy level T1 of the compound satisfies $\Delta E_{st}=E_{S1}-E_{T1} \leq 0.30$ eV, and more preferably $\Delta E_{st}=E_{S1}-E_{T1} \leq 0.25$ eV.

Since the compound according to the present disclosure has the TADF property, it can be used as a light-emitting material of a light-emitting layer in an organic light-emitting display device, or it can be used as a host or guest material of a light-emitting layer. Meanwhile, the compound according to the present disclosure can be used as a red light-emitting material, as a green light-emitting material or as a blue light-emitting material of the light-emitting layer in the organic light-emitting display device. Therefore, the present disclosure also provides uses of the above compounds in organic light-emitting display devices.

The compounds according to the present disclosure have high luminescence efficiency due to the luminescent mechanism of TADF. When applied to an organic light-emitting display device, the luminescence efficiency thereof also can be improved. Further, the organic compound according to the present disclosure, as TADF material, has advantage of lower cost, comparing with the phosphorescent metal complex.

The present disclosure provides a method for preparing the compounds according to several embodiments of the present disclosure. In the following examples, synthesis schemes of compounds P1, P2, P4 and P11 are described as follow.

Example 1

Synthesis of Compound P1

Compound P1 was synthesized according to the following schemes:

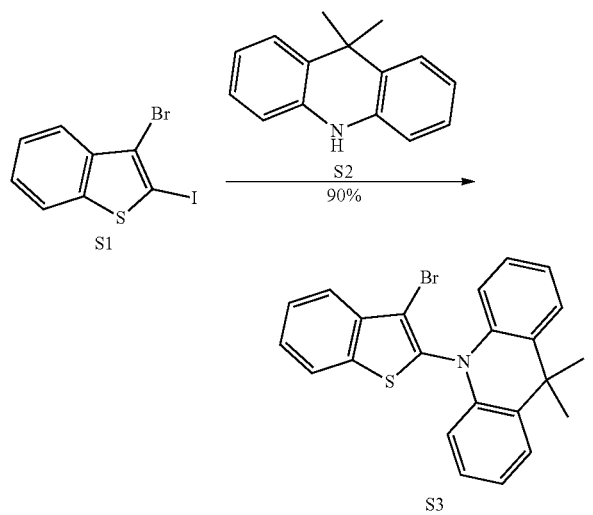

Compound S1 (10 mmol), 9,9-dimethyl-9,10-dihydroacridine (Compound S2, 10.5 mmol). (dibenzylideneacetone) dipalladium (0) (0.05 mmol), sodium t-butoxide (14 mmol) and 4,5-bis(diphenylphosphino)-9,9-dimethylxanthene (0.2 mmol) were added to a 50 mL flask with three necks, degasification and nitrogen replacement were repeated three times during stirring, and then 20 mL of toluene was added through a syringe. The mixture was refluxed for 3 hours under nitrogen stream. After the reaction was completed, the mixture was cooled to room temperature, extracted with dichloromethane after adding water, and washed with saturated brine. After the organic phase was dried with anhydrous sodium sulfate, the solvent was removed by evaporation, and the crude product was purified by column chromatography to obtain an intermediate Compound S3 (9 mmol, 90%).

MALDI-TOF MS: m/z calcd for $C_{23}H_{18}BrNS$: 419.0; found: 419.6.

Elemental Analysis:
Calculated: C, 65.72; H, 4.32; Br, 19.01; N, 3.33; S, 7.63;
Measured: C, 65.70; H, 4.33; N, 3.34; S, 7.63.

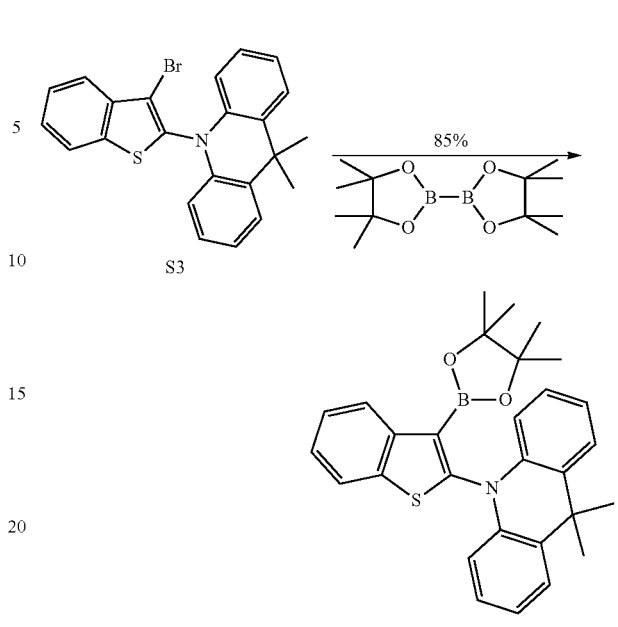

Compound S3 (30 mmol), bis(pinacolato)diboron (36 mmol), [1,1'-bis(diphenylphosphino)ferrocene]dichloropalladium(II) (0.3 mmol) and potassium acetate (75 mmol) were added to a 250 mL flask with three necks, then degasification and nitrogen replacement were repeated for three times during stirring, and 100 mL of tetrahydrofuran was added through a syringe. After stirring at a certain rotation speed, the mixture was refluxed at a reaction temperature of 80° C. for 5 hours. After the reaction was completed, the mixture was cooled to room temperature, extracted with diethyl ether after adding 100 ml of water, and the organic phase was dried over anhydrous sodium sulfate. The solvent was removed by evaporation, and the crude product was purified by column chromatography to obtain an intermediate Compound S4 (25.5 mmol, 85%).

MALDI-TOF MS: m/z calcd for $C_{29}H_{30}BNO_2S$: 467.2; found: 466.8.

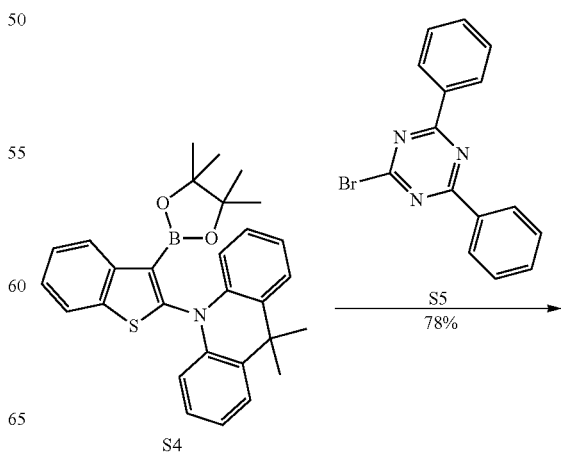

-continued

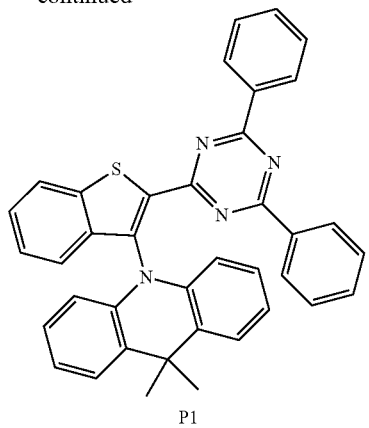

P1

Under protection of nitrogen, Compound S4 (20 mmol), Compound S5 (20 mmol), [Pd$_2$(dba)$_3$].CHCl$_3$ (0.4 mmol) and HP(t-Bu)$_3$.BF$_4$ (0.8 mmol) were weighed and then added to a 250 mL flask with two necks. 100 mL of toluene (N$_2$ was introduced in advance for 15 minutes to remove oxygen) was added into the flask, and then 12 mL of 1M aqueous solution of K$_2$CO$_3$ (N$_2$ was introduced in advance for 15 minutes to remove oxygen) was added dropwise and stirred at room temperature overnight. After the reaction was completed, 100 mL of deionized water and a few drops of 2M HCl were added. The organic phase was collected and dried over anhydrous Na$_2$SO$_4$ after extracting with dichloromethane. The dried solution was filtered, and the solvent was removed using a rotary evaporator to obtain a crude product. The crude product was purified through a silica gel column chromatography to obtain a solid P1 (15.6 mmol, 78%).

MALDI-TOF MS: m/z calcd for C$_{38}$H$_{28}$N$_4$S: 572.2.1; found: 572.5.

Elemental Analysis:
Calculated: C, 79.69; H, 4.93; N, 9.78; S, 5.60;
Measured: C, 79.68; H, 4.95; N, 9.77; S, 5.60.

Example 2

Synthesis of Compound P2
Compound P2 was synthesized according to the following schemes:

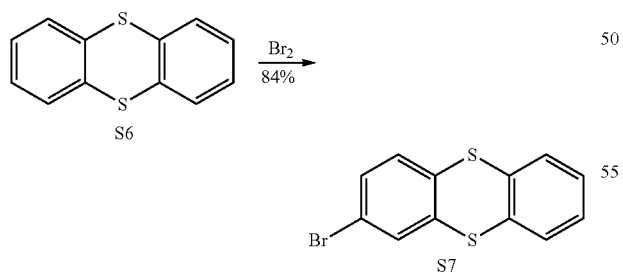

Under protection of nitrogen, Compound S6 (30 mmol) was weighed and mixed with 60 mL of acetic acid, and liquid bromine (36 mmol) was added dropwise. The obtained mixture was stirred at 80° C. for 5 hours. The excess elemental bromine was quenched with an aqueous solution of NaHSO$_3$, and then the mixture was extracted with dichloromethane (100 mL) for 3 times. The organic phase was collected and dried over anhydrous Na$_2$SO$_4$. After performing a filtration, the solvent was removed under a reduced pressure by using a rotary evaporator to obtain a crude product. The crude product was purified by silica gel column chromatography, and finally purified by recrystallization with n-hexane to obtain a solid powder S7 (25.2 mmol, 84%).

MALDI-TOF MS: m/z calcd for C$_{12}$H$_7$BrS$_2$: 293.9; found: 293.8.

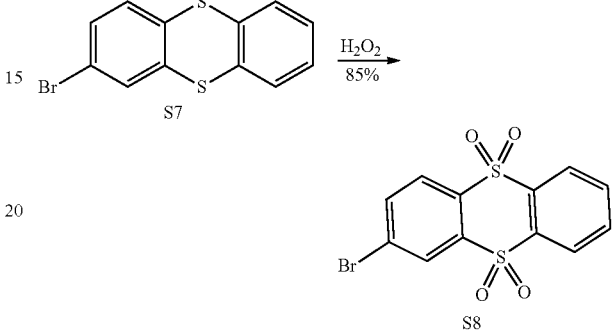

40 mL of acetic acid and 20 mL of dichloromethane were added to a 50 mL flask with one neck at room temperature. Then the intermediate Compound S7 (6 mmol), 5 times equivalent amount of 30% hydrogen peroxide were added, and the mixture was stirred at a temperature of 55-60° C. for 20-24 h. After being cooled to room temperature and extracted with dichloromethane, a white solid S8 (5.1 mmol, 85%) is obtained by column chromatography.

MALDI-TOF MS: m/z calcd for C$_{12}$H$_7$BrO$_4$S$_2$: 357.9; found: 358.0.

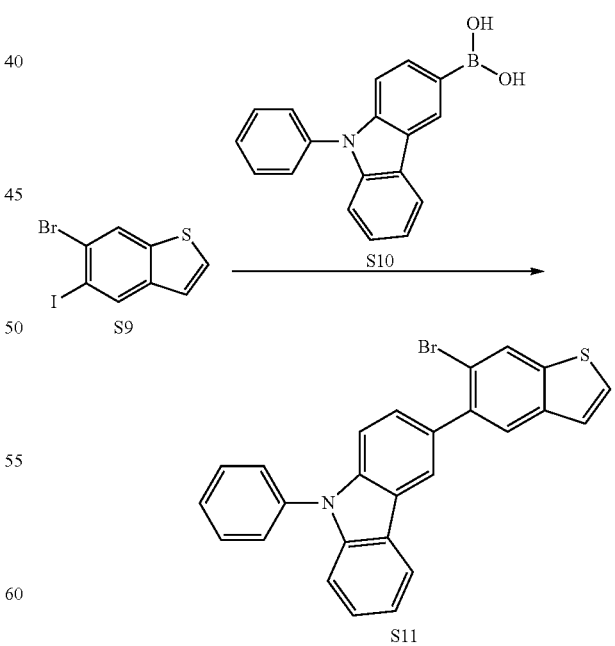

Under protection of nitrogen, compounds S9 (16.0 mmol), S10 (16.5 mmol), [Pd$_2$(dba)$_3$].CHCl$_3$ (0.4 mmol) and HP(t-Bu)$_3$.BF$_4$ (0.8 mmol) were weighed and then added to a 250 mL flask with two necks. 100 mL of toluene (N₂ was introduced in advance for 15 minutes to remove oxygen) was added into the flask, then 12 mL of 1M aqueous solution of K₂CO₃ (N₂ was introduced in advance for 15 minutes to remove oxygen) was added dropwise, and the mixture was stirred at room temperature overnight. After the reaction was completed, 100 mL of deionized water and a few drops of 2M HCl were added. The organic phase was collected and dried over anhydrous Na₂SO₄ after performing an extraction with dichloromethane. The dried solution was filtered, and the solvent was removed using a rotary evaporator to obtain a crude product. The crude product was further purified through silica gel column chromatography to obtain a solid S11 (11 mmol, 69%).

MALDI-TOF MS: m/z calcd for $C_{26}H_{16}BrNS$: 453.0; found: 453.3.

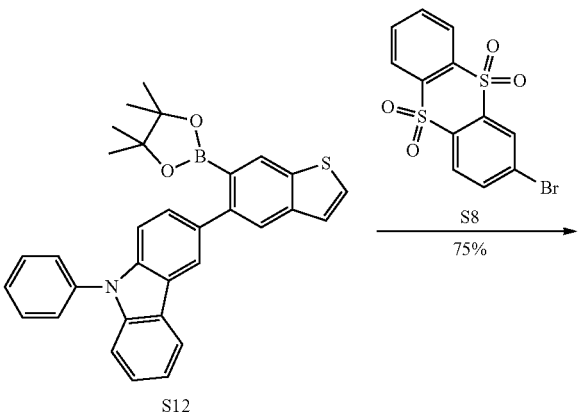

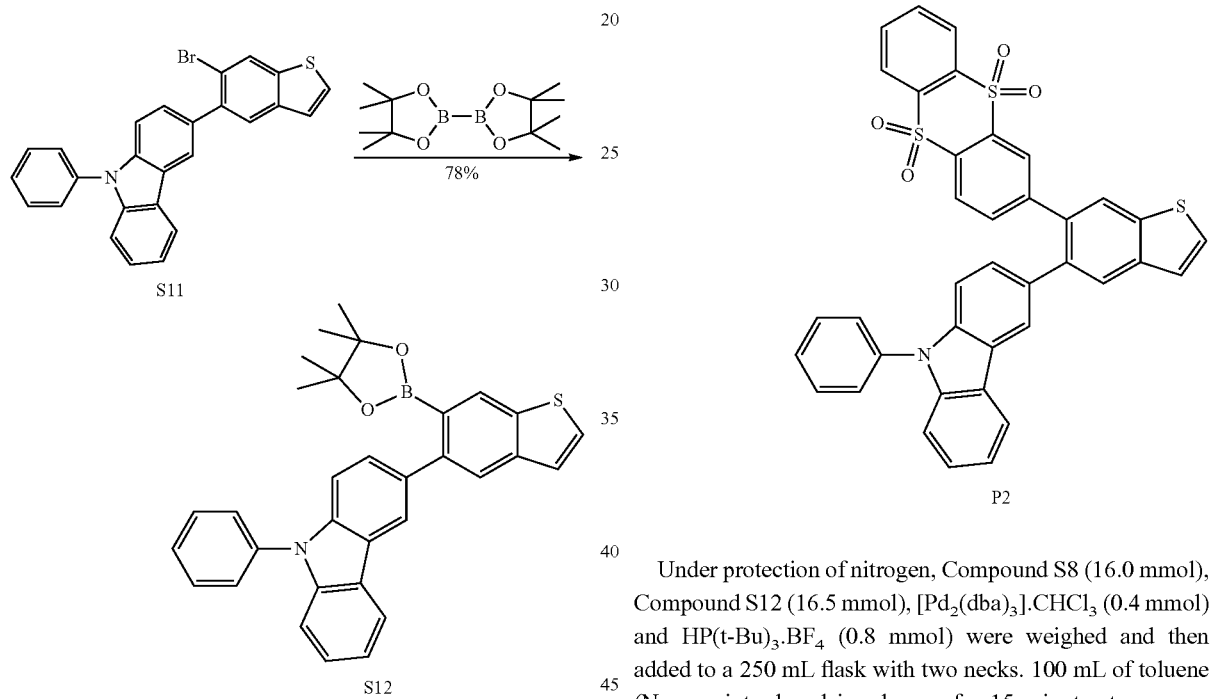

Compound S11 (30 mmol), bis(pinacolato)diboron (36 mmol), [1,1'-bis(diphenylphosphino)ferrocene]dichloropalladium(II) (0.3 mmol) and potassium acetate (75 mmol) were added into a 250 ml flask with three necks, degasification and nitrogen replacement were repeated three times during stirring, and 100 mL of tetrahydrofuran was added through a syringe. After stirring at a certain rotation speed, the mixture was refluxed at a reaction temperature of 80° C. for 5 hours. After the reaction was completed, the reaction mixture was cooled to room temperature, extracted with diethyl ether after adding 100 ml of water, and the obtained organic phase was dried over anhydrous sodium sulfate. The solvent was removed by evaporation to obtain a crude product, which was further purified by column chromatography to obtain an intermediate Compound S12 (24.0 mmol, 80%).

MALDI-TOF MS: m/z calcd for $C_{32}H_{28}BNO_2S$: 501.2; found: 501.0.

Under protection of nitrogen, Compound S8 (16.0 mmol), Compound S12 (16.5 mmol), [Pd₂(dba)₃].CHCl₃ (0.4 mmol) and HP(t-Bu)₃.BF₄ (0.8 mmol) were weighed and then added to a 250 mL flask with two necks. 100 mL of toluene (N₂ was introduced in advance for 15 minutes to remove oxygen) was added into the flask, and then 12 mL of 1M aqueous solution of K₂CO₃ (N₂ was introduced in advance for 15 minutes to remove oxygen) was added dropwise and stirred at room temperature overnight. After the reaction was completed, 100 mL of deionized water and a few drops of 2M HCl were added. The organic phase was collected and dried over anhydrous Na₂SO₄ after performing an extraction with dichloromethane. The dried solution was filtered, and the solvent was removed using a rotary evaporator to obtain a crude product. The crude product was purified through a silica gel column chromatography to obtain a solid P2 (12 mmol, 75%).

MALDI-TOF MS: m/z calcd for $C_{38}H_{23}NO_4S_3$: 653.1; found: 653.6.

Elemental Analysis

Calculated: C, 69.81; H, 3.55; N, 2.14; O, 9.79; S, 14.71;
Measured: C, 69.83; H, 3.53; N, 2.12; O, 9.81; S, 14.71.

Example 3

Synthesis of Compound P4

Compound P4 was synthesized according to the following schemes:

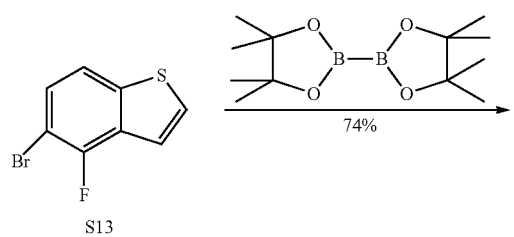

S13

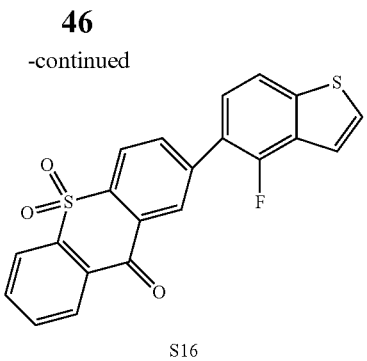

S16

Under protection of nitrogen, Compound S15 (15 mmol), Compound S14 (16.0 mmol). [Pd$_2$(dba)$_3$].CHCl$_3$ (0.4 mmol) and HP(t-Bu). BF$_4$ (0.8 mmol) were weighed and then added to a 250 mL flask with two necks. 100 mL of toluene (N$_2$ was introduced in advance for 15 minutes to remove oxygen) was added into the flask, then 12 mL of 1M aqueous solution of K$_2$CO$_3$ (N$_2$ was introduced in advance for 15 minutes to remove oxygen) was added dropwise, and stirred at room temperature overnight. After the reaction was completed, 100 mL of deionized water and a few drops of 2M HCl were added. The organic phase was collected and dried over anhydrous Na$_2$SO$_4$ after performing an extraction with dichloromethane. The dried solution was filtered, and the solvent was removed using a rotary evaporator to obtain a crude product, which was further purified through a silica gel column chromatography to obtain a solid S16 (10.2 mmol, 68%).

S14

Compound S13 (30 mmol), bis(pinacolato)diboron (36 mmol), [1,1'-bis(diphenylphosphino)ferrocene]dichloropalladium(II) (0.3 mmol) and potassium acetate (75 mmol) were added to a 250 mL flask with three necks, then degasification and nitrogen replacement were repeated three times during stirring, and 100 mL of tetrahydrofuran was added through a syringe. After stirring at a certain rotation speed, the mixture was refluxed at a reaction temperature of 80° C. for 5 hours. After the reaction was completed, the reaction mixture was cooled to room temperature, extracted with diethyl ether after adding 100 ml of water, and the organic phase was dried over anhydrous sodium sulfate. The solvent was removed by evaporation to obtain a crude product, which was further purified by column chromatography to obtain an intermediate Compound S14 (24 mmol, 80%).

MALDI-TOF MS: m/z calcd for C14H16BFO2S: 278.1; found: 278.2.

MALDI-TOF MS: m/z calcd for C$_{21}$H$_{11}$FO$_3$S$_2$: 394.0. found: 394.3.

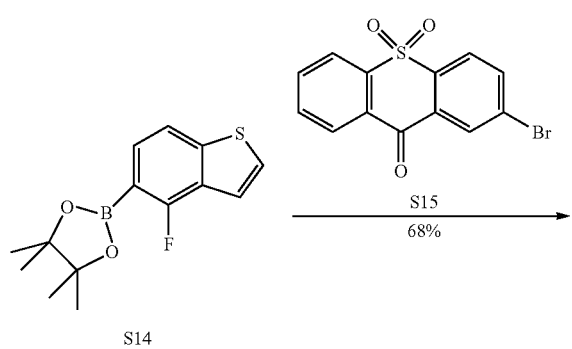

Compound S16 (10.0 mmol), 9,9-dimethyl-9,10-dihydroacridine (Compound S17, 10.5 mmol), (dibenzylideneacetone) dipalladium (0) (0.05 mmol), sodium t-butoxide (14.0 mmol) and 4,5-bis(diphenylphosphino)-9,9-dimethylxanthene (0.2 mmol) were added to a 50 mL flask with three necks, then degasification and nitrogen replacement were repeated for three times during stirring, and 20 mL of toluene was added through a syringe. The mixture was refluxed for 3 hours under nitrogen stream. After the reaction was completed, the mixture was cooled to room temperature, extracted with dichloromethane after adding water, and washed with saturated brine. After the organic phase was dried with anhydrous sodium sulfate, the solvent was removed by evaporation and the crude product was purified by column chromatography to obtain Compound P4 (6.5 mmol, 65%).

MALDI-TOF MS: m/z calcd for $C_{41}H_{35}NO_3S_2$: 653.2; found: 653.5.

Elemental Analysis:
Calculated: C, 75.31; H, 5.40; N, 2.14; O, 7.34; S, 9.81;
Measured: C, 75.31; H, 5.38; N, 2.15; O, 7.36; S, 9.80.

Example 4

Synthesis of Compound P11
Compound P11 was synthesized according to the following schemes:

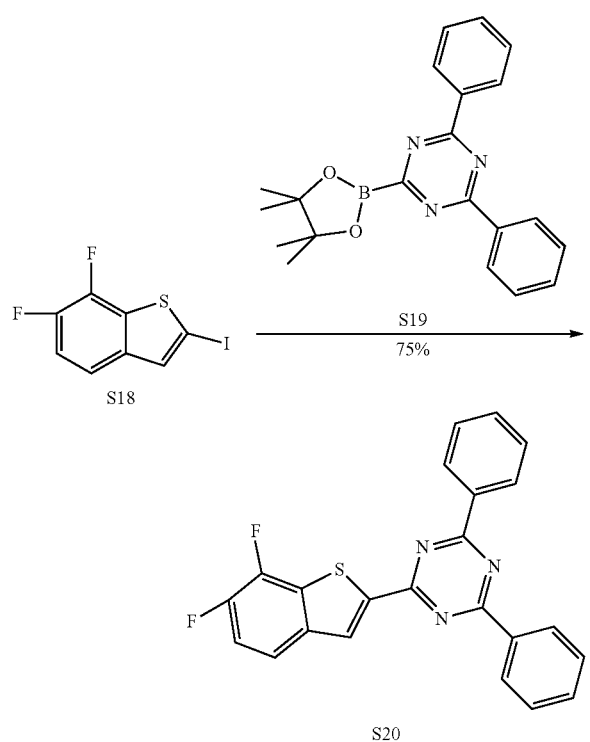

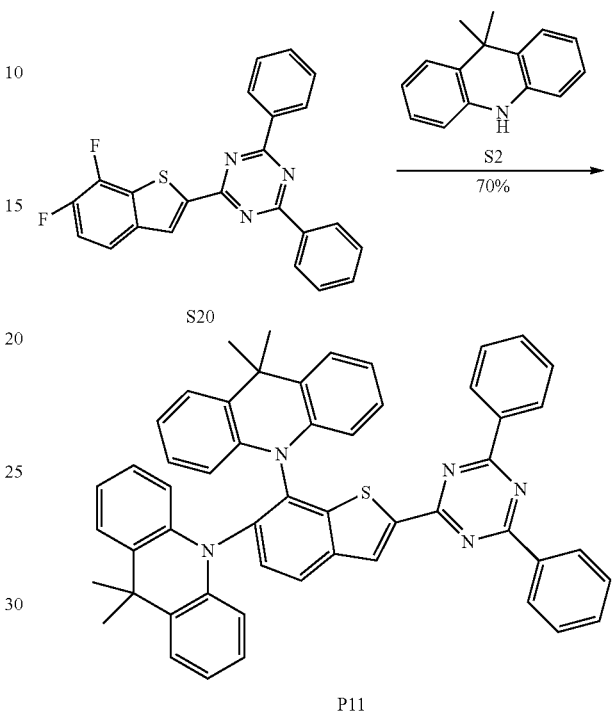

Under protection of nitrogen, Compound S18 (14.0 mmol), Compound S19 (15.3 mmol). [$Pd_2(dba)_3$].$CHCl_3$ (0.4 mmol) and HP(t-Bu)$_3$.BF$_4$ (0.8 mmol) were weighed and then added to 250 mL two-neck flask. 100 mL of toluene ($N_2$ was introduced in advance for 15 minutes to remove oxygen) was added into the two-neck flask, then 12 mL of 1M aqueous solution of $K_2CO_3$ ($N_2$ was introduced in advance for 15 minutes to remove oxygen) was added dropwise, and stirred at room temperature overnight. After the reaction was completed, 100 mL of deionized water and a few drops of 2M HCl were added. The organic phase was collected and dried over anhydrous $Na_2SO_4$ after performing an extraction with dichloromethane. The dried solution was filtered, and the solvent was removed using a rotary evaporator to obtain a crude product, which was further purified through a silica gel column chromatography to obtain a solid S20 (10.5 mmol, 75%).

MALDI-TOF MS: m/z calcd for $C_{23}H_{13}F_2N_3S$: 401.1; found: 400.7.

Compound S20 (10.0 mmol), 9,9-dimethyl-9,10-dihydroacridine (Compound S2, 21.0 mmol), (dibenzylideneacetone)dipalladium(0) (0.1 mmol), sodium t-butoxide (28.0 mmol) and 4,5-bis(diphenylphosphino)-9,9-dimethylxanthene (0.4 mmol) were added to a 100 mL flask with three necks, then degasification and nitrogen replacement were repeated for three times during stirring, and 40 mL of toluene was added through a syringe. The mixture was refluxed for 3 hours under nitrogen stream. After the reaction was completed, the mixture was cooled to room temperature, extracted with dichloromethane after adding water, and washed with saturated brine. After the organic layer with anhydrous sodium sulfate, the solvent was removed by evaporation and the obtained crude product was purified by column chromatography to obtain Compound P11 (7.0 mmol, 70%).

MALDI-TOF MS: m/z calcd for $C_{53}H_{41}N_5S$: 779.3; found: 779.8.

Elemental Analysis:
Calculated: C, 81.61; H, 5.30; N, 8.98; S, 4.11;
Measured: C, 81.59; H, 5.32; N, 8.97; S, 4.12.

Example 5

Figure 2:
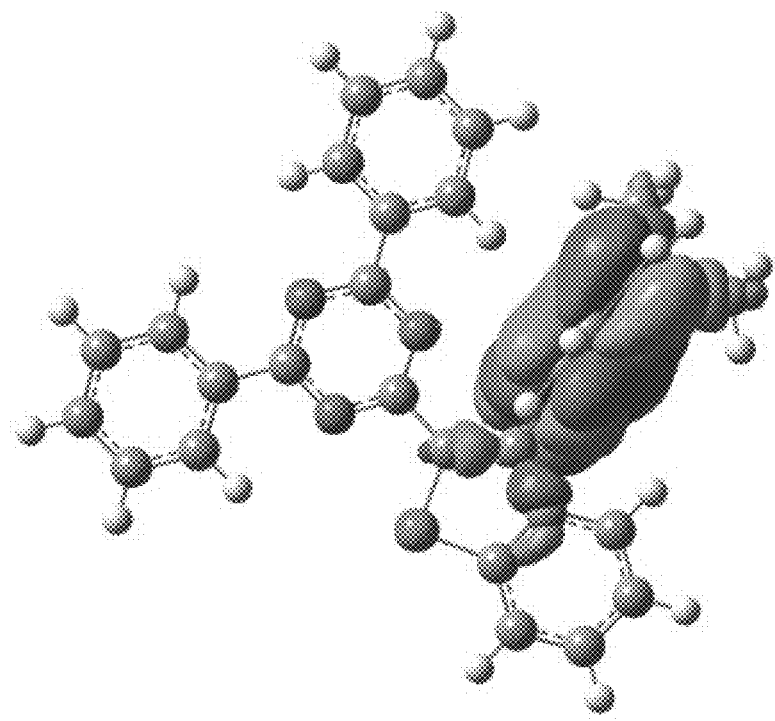
FIG. 2 is an energy level diagram of HOMO of a Compound P1 according to the present disclosure.
Figure 3:
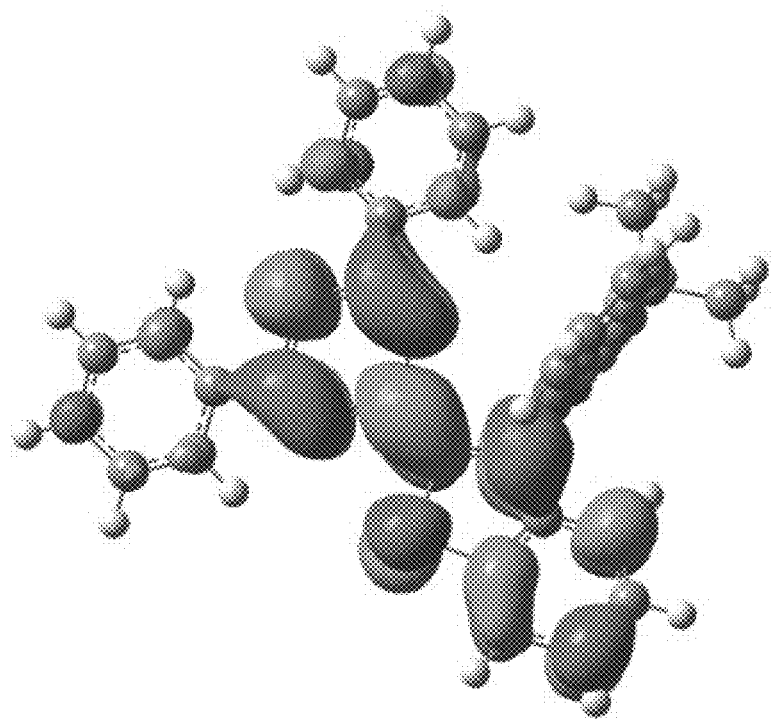
FIG. 3 is an energy level diagram of LUMO of the Compound P1 according to the present disclosure.

FIG. 2 and FIG. 3 illustrate orbital configurations of Compound P1. In one embodiment, FIG. 2 is an energy level diagram of HOMO of Compound P1, and FIG. 3 is an energy level diagram of LUMO of Compound P1. It can be seen from FIG. 2 that the HOMO and the LUMO of the Compound P1 are distributed on different units, i.e., a complete separation is achieved. Thus, the intersystem energy difference $\Delta E_{ST}$ can be reduced, thereby enhancing the reverse intersystem crossing ability.

With respect to Compounds P1 to P8, the distribution of the molecular frontier orbits was optimized and calculated by applying the density functional theory (DFT) and using a Gaussian 09 software with B3LYP/6-31G(d) calculation level. Meanwhile, the singlet energy level $S_1$ and the triplet energy level $T_1$ were simulated and calculated based on the time-dependent density functional theory (TDDFT).

Data of Compounds P1 to P8 are shown in Table 1.

TABLE 1

Relevant Performance Data of Compounds P1~P8

| No. | Compound | HOMO (eV) | LUMO (eV) | $S_1$ (eV) | $T_1$ (eV) | $\Delta E_{ST}$ (eV) | Eg (eV) |
|---|---|---|---|---|---|---|---|
| 1 | P1 | −5.53 | −3.22 | 1.90 | 1.89 | 0.01 | 2.31 |
| 2 | P2 | −5.66 | −3.22 | 2.95 | 2.84 | 0.11 | 2.44 |
| 3 | P3 | −5.74 | −3.02 | 2.63 | 2.62 | 0.01 | 2.72 |
| 4 | P4 | −5.94 | −3.59 | 2.77 | 2.49 | 0.28 | 2.35 |
| 5 | P5 | −5.91 | −3.31 | 3.14 | 2.87 | 0.27 | 2.60 |
| 6 | P6 | −5.85 | −3.04 | 2.65 | 2.61 | 0.04 | 2.81 |
| 7 | P7 | −5.93 | −3.24 | 2.99 | 2.76 | 0.23 | 2.69 |
| 8 | P8 | −5.72 | −2.97 | 3.14 | 3.09 | 0.05 | 2.75 |

In Table 1, $S_1$ represents a singlet energy level, $T_1$ represents a triplet energy level, $\Delta E_{ST}$ represents an energy difference between the singlet energy level and the triplet energy level, and Eg represents an energy difference between HOMO and LUMO energy level.

It can be seen from Table 1 that the $\Delta E_{ST}$ of respective compound is less than 0.3 ev, which means a small difference between the singlet energy level and the triplet energy level. At the same time, a fluorescence lifetime of respective compound is of a magnitude of microsecond, revealing a significant delayed fluorescence effect.

Figure 4:
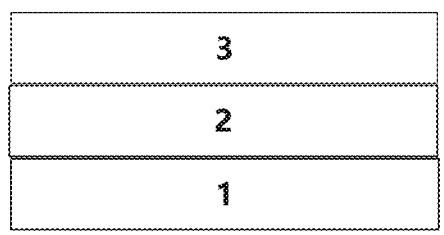
FIG. 4 is a structural schematic diagram of an organic light-emitting component according to an embodiment according to the present disclosure.

In one embodiment of the present disclosure provides an organic light-emitting display device. The organic light-emitting display device includes an anode, a cathode, and at least one organic thin film layer disposed between the anode and the cathode, as shown in FIG. 4. The organic thin film layer serves as a light-emitting layer of the organic light-emitting display device. A light-emitting material of the light-emitting layer is selected from a group consisting of the compounds according to the present disclosure, and combinations thereof.

FIG. 4 is a schematic structural diagram of an organic light-emitting component according to an embodiment of the present disclosure. The organic light-emitting component includes a first electrode 1, a light-emitting layer 2, and a second electrode 3 that are stacked sequentially. A substrate can be additionally provided under the first electrode 1 or above the second electrode 3. Any substrate known in the conventional organic light-emitting components can be used, and the substrate can be a glass substrate or a transparent plastic substrate that has excellent properties of mechanical strength, thermal stability, transparency, surface smoothness, operability, and water resistance.

The light-emitting layer 2 disposed on the first electrode 1 includes a hole transmission region, an emission layer, and an electron transmission region. The hole transmission region may be disposed between the first electrode 1 and the light-emitting layer 2. The hole transmission region may include at least one layer of a hole injection layer, a hole transmission layer, an electron blocking layer, or a buffering layer. In one embodiment, the hole transmission region includes multiple layers formed by any combination thereof.

The hole transmission region may only include a hole injection layer or a hole transmission layer. The hole transmission region may include a buffering layer. The buffering layer can compensate the optical resonance distance based on the wavelength of light emitted from the light-emitting layer 2, and thus improve the efficiency of the organic light-emitting component.

The light-emitting layer 2 may include a host material and a dopant. The electron transmission region may include at least one of a hole blocking layer, an electron transmission layer, an electron injection layer, or the electron transmission region may include multiple layers formed by any combination thereof. For example, the electron transmission region may have a structure of hole blocking layer/electron transmission layer/electron injection layer, or a structure of electron transmission layer/electron injection layer, which is not limited thereto. The electron transmission layer may have a single layer structure or a multilayer structure that contains two or more different materials.

In the organic light-emitting display device provided by the present disclosure, the anode can be made of metal selected from a group consisting of copper, gold, silver, iron, chromium, nickel, manganese, palladium, platinum, etc., and alloys thereof. The anode can be made of metal oxide, such as indium oxide, zinc oxide, indium tin oxide (ITO), indium zinc oxide (IZO), and the like. The anode also can be made of a conductive polymer, such as polyaniline, polypyrrole, poly(3-methylthiophene) and the like. In addition to the anode material mentioned above, the anode also can be made of any suitable material selected from the anode materials known in the related art, and combinations thereof, as long as the material of the anode is conductive to injecting holes.

In the organic light-emitting display device provided by the present disclosure, the cathode can be made of metal, such as aluminum, magnesium, silver, indium, tin, titanium, etc., or alloys thereof. The cathode also can be made of multiple-layer metal material, such as LiF/Al, $LiO_2$/Al, $BaF_2$/Al, and the like. In addition to the cathode materials listed above, the cathode also can be made of any suitable material selected from the cathode material known in the related art, and combinations thereof, as long as the material of the cathode is conductive to injecting holes.

In the present disclosure, the organic light-emitting display device can be manufactured by forming an anode on a transparent or opaque smooth substrate, forming an organic thin layer on the anode, and further forming a cathode on the organic thin layer. The organic thin layer can be formed by a known method such as vapor deposition, sputtering, spin coating, dipping, ion plating, and the like.

The compound according to the present disclosure can be used as a dopant, a co-dopant, or a host material in the light-emitting layer.

In the organic light-emitting display device provided by the present disclosure, the light-emitting layer of the organic light-emitting display device includes a host material or a guest material. The host material or the guest material is selected from a group consisting of the compounds according to the present disclosure, and combinations thereof.

In the organic light-emitting display device according to an embodiment of the present disclosure, the light-emitting material of the light-emitting layer is a red light-emitting material, and the red light-emitting material has a singlet energy level of 1.61-1.99 eV.

In the organic light-emitting display device according to an embodiment of the present disclosure, the light-emitting material of the light-emitting layer is a green light-emitting material, and the green light-emitting material has a singlet energy level of 2.15-2.52 eV.

In the organic light-emitting display device according to an embodiment of the present disclosure, the light-emitting material of the light-emitting layer is a blue light-emitting material, and the blue light-emitting material has a singlet energy level of 2.52 to 2.73 eV.

In the organic light-emitting display device according to an embodiment of the present disclosure, the light-emitting material includes a host material and a guest material. The host material is selected from a group consisting of 2,8-bis(diphenylphosphinyl)dibenzothiophene, 4,4'-bis(9-carbazolyl)biphenyl, 3,3'-bis(N-carbazolyl)-1,1'-biphenyl, 2,8-bis(diphenylphosphinyl)dibenzofuran, bis(4-(9H-carbazolyl-9-yl)phenyl)diphenylsilane, 9-(4-tert-butylphenyl)-3,6-bis(triphenylsilyl)-9H-carbazole, bis(2-diphenylphosphinyl)diphenyl ether, 1,3-bis[3,5-di(pyridine-3-yl)phenyl]benzene, 4,6-bis(3,5-di(3-pyridyl)phenyl)-2-methylpyrimidine, 9-(3-(9H-carbazolyl-9-yl)phenyl)-9H-carbazole-3-cyano, 9-phenyl-9-[4-(triphenylsilyl)phenyl]-9H-fluorene, 1,3,5-tris(1-phenyl-1H-benzoimidazol-2-yl)benzene, diphenyl[4-(triphenylsilyl)phenyl]phosphine oxide, 4,4',4''-tris(carbazol-9-yl)triphenylamine, 2,6-dicarbazolyl-1,5-pyridine, polyvinylcarbazole, polyfluorene, and combinations thereof. The guest material is selected from a group consisting of the compounds according to the present disclosure, and combinations thereof. An energy difference between a HOMO energy level of the host material and a HOMO energy level of the guest material is less than 0.6 eV, or an energy difference between LUMO energy level of the host material and LUMO energy level of the guest material is less than 0.6 eV.

In the organic light-emitting display device according to an embodiment of the present disclosure, a singlet energy level of the host material is higher than a singlet energy level of the guest material, and an energy difference between the singlet energy level of the host material and the singlet energy level of the guest material is less than 1.0 eV.

In the organic light-emitting display device according to an embodiment of the present disclosure, the light-emitting material of the light-emitting layer includes a host material and a guest material. The host material is selected from a group consisting of the compounds according to the present disclosure, and combinations thereof. The guest material is selected from a group consisting of fluorescent material, thermally activated delayed fluorescent material, and phosphorescent material. An energy difference between a HOMO energy level of the host material and a HOMO energy level of the guest material is less than 0.6 eV, or an energy difference between a LUMO energy level of the host material and a LUMO energy level of the guest material is less than 0.6 eV.

In the organic light-emitting display device according to an embodiment of the present disclosure, the light-emitting material of the light-emitting layer includes a host material and a guest material, the host material is selected from a group consisting of the compounds according to the present disclosure, and combinations thereof. The guest material is selected from a fluorescent material or a thermally activated delayed fluorescent material. A singlet energy level of the guest material is less than singlet energy level of the host material, and a difference between the singlet energy level of the host material and the singlet energy level of the guest material is less than 1.0 eV.

In the organic light-emitting display device according to an embodiment of the present disclosure. The light-emitting material of the light-emitting layer includes a host material and a guest material. The host material is selected from a group consisting of the compounds according to the present disclosure, and combinations thereof. The guest material is a phosphorescent material. A triplet energy level of the guest material is lower than a triplet energy level of the host material, and an energy difference between the triplet energy level of the host material and the triplet energy level of the guest material is less than 1.0 eV.

According to an embodiment of the present disclosure, the light-emitting material is a thermally activated delayed fluorescent material.

The organic functional layer according to the present disclosure further includes at least one of a hole injection layer (HIL), a hole transmission layer (HTL), an electron blocking layer (EBL), a hole blocking layer (HBL), an electron transmission layer (ETL), and an electron injection layer (EIL).

The hole injection layer, the hole transmission layer, and the electron blocking layer are each made of a material selected from a group consisting of N,N'-diphenyl-N,N'-bis(1-naphthyl)-1,1'biphenyl-4,4''diamine (α-NPD), 4,4',4''-tris(carbazol-9-yl)-triphenylamine (TCTA), 1,3-bis(N-carbazolyl)benzene (mCP), 4,4'-bis(9-carbazole)biphenyl (CBP), 3,3'-bis(N-carbazolyl)-1,1'-biphenyl (mCBP), 2,3,6,7,10,11-hexacyano-1,4,5,8,9,12-hexaazatriphenylene (HATCN), 4,4'-cyclohexylidenebis[N,N-bis(4-methylphenyl)aniline] (TAPC), N,N'-diphenyl-N,N'-(1-naphthyl)-1, 1'-biphenyl-4, 4''-diamine (α-NPB), N,N'-bis (naphthalen-2-yl)-N,N'-di(phenyl)biphenyl-4,4'-diamine (NPB), poly(3,4-ethylenedioxythiophene)-polystyrenesulfonate (PEDOT:the PSS), polyvinyl carbazole (PVK), 9-phenyl-3,9-bicarbazolyl (CCP), molybdenum trioxide ($MoO_3$). However, the material is not limited thereto.

The hole blocking layer, the electron transmission layer, or the electron injection layer each can be made of a material selected from a group consisting of 2,8-bis(diphenylphosphinyl)dibenzothiophene (PPT), TSPO1, TPBi, 2,8-bis(diphenylphosphinyl)dibenzofuran (PPF), bis[2-(diphenylphosphino)phenyl] ether oxide (DPEPO), lithium fluoride (LiF), 4,6-bis(3,5-di-3-pyridylphenyl)-2-methylpyrimidine (B3PYMPM), 4,7-diphenyl-1,10-phenanthroline (Bphen), 1,3,5-tris[(3-pyridyl)-3-phenyl]benzene (TmPyBP), tris[2,4,6-trimethyl-3-(3-pyridyl)phenyl]borane (3TPYMB), 1,3-bis(3,5-dipyridine-3-yl-phenyl]benzene (B3PYPB), 1,3-bis[3,5-di(pyridin-3-yl)phenyl]benzene (BMPYPHB), 2,4,6-Tris(biphenyl-3-yl)-1,3,5-triazine (T2T), diphenylbis(4-(pyridin-3-yl)phenyl)silane (DPPS), cesium carbonate ($Cs_2O_3$), bis(2-methyl-8-quinolinolato-N1,O8)-(1,1'-Biphenyl-4-olato)aluminum (BAlq), 8-hydroxyquinoline lithium (Liq), and tris(8-hydroxyquinoline) aluminum ($Alq_3$). However, the material is not limited thereto.

The substrate according to the present disclosure can be a rigid substrate (borosilicate glass, float soda-lime glass, high refractive index glass, stainless steel, etc.), or a flexible substrate (for example, a polyimide (PI) plastic substrate, polyethylene terephthalate (PET) plastic substrate, poly(ethylene naphthalate) (PEN) plastic substrate, polyethersulfone resin substrate (PES), polycarbonate plastic substrate (PC), ultra-thin flexible glass substrate, metal foil substrate, etc.).

Figure 5:
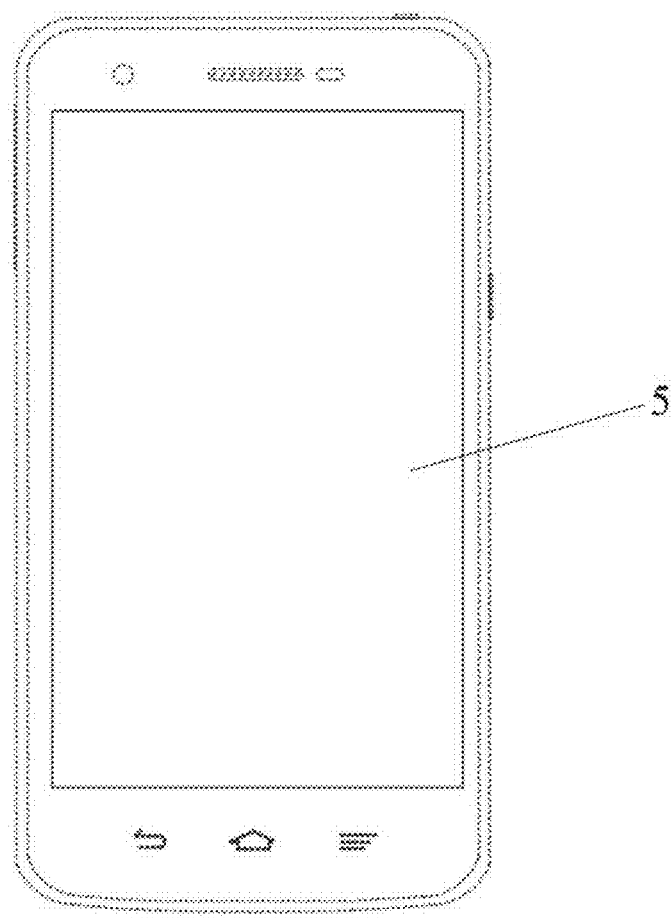
FIG. 5 is a structural schematic diagram of an organic light-emitting display device according to an embodiment according to the present disclosure.

In the present disclosure, the organic light-emitting display device can be an organic light-emitting display device having OLED. The organic light-emitting display device may be a display screen or display panel of mobile phone, computer, liquid crystal television, smart watch, smart car, VR or AR helmet, and other smart devices. FIG. 5 is a schematic diagram of a display screen of mobile phone, in which the display screen is denoted with number 5.

The following Example 6 to Example 8 aim to show the manufacturing process and performances of the organic light-emitting components.

Example 6

Manufacturing Process of Organic Light-Emitting Component by Vapor Deposition Method A substrate having an ITO film with a thickness of 100 nm was ultrasonically washed with distilled water, acetone, and isoinol, then dried in an oven, and the surface was subjected to UV treatment for 30 minutes. Then the substrate was transferred to a vacuum vapor deposition chamber. The vapor deposition of each layer was carried out under a vacuum of $2 \times 10^{-6}$ Pa. A hole injection layer was formed by deposing 5 nm of HATCN. A hole transmission layer (HTL) was formed by deposing 40 nm of N,N'-diphenyl-N,N'-bis(1-naphthyl)-1,1'biphenyl-4,4"diamine (α-NPD) and then deposing 10 nm of 4,4',4"-tris(carbazol-9-yl)-triphenylamine (TCTA). The compound according to the present disclosure used as a dopant of the light-emitting layer, and 3,3'-bis (N-carbazolyl)-1,1'-biphenyl (mCBP) used as a host material of the light-emitting layer, are deposited on the hole transmission layer at the same time, so as to form a light-emitting having a thickness of 30 nm. A hole blocking layer (HBL) having a thickness of 5 nm was deposited on the light-emitting layer with diphenyl [4-(triphenylsilyl) phenyl] phosphine oxide (TSPO1). An electron transmission layer (ETL) having a thickness of 30 nm was deposited on the hole blocking layer with 4,7-diphenyl-1,10-phenanthroline (Bphen). Then, a LiF layer having a thickness of 2.5 nm and an Al layer having a thickness of 100 nm were deposited on the electron transmission layer sequentially, serving as an electron injection layer (EIL) and a cathode respectively, so as to obtain an organic light-emitting display component.

The organic light-emitting component also can be manufactured by a solution method.

The process of manufacturing a non-doped component includes following steps: ultrasonically washing an ITO glass with acetone, alkaline washing solution, ultrapure water, and isopropyl alcohol sequentially for two times, 15 minutes for each time; treating the ITO glass with an ozone cleaner for 15 minutes; spraying 40 nm of PEDOT:PSS solution onto the glass substrate with a ink-jet printer, and placing the glass substrate in a vacuum oven at 120° C. for 45 minutes for drying; preparing a TAPC layer and an mCP layer on PEDOT:PSS layer, serving as a hole transmission layer and an electron blocking layer, respectively; spraying a toluene solution of the compound according to the present disclosure (concentration: 12 mg/mL) with ink-jet printer so as to form a light-emitting layer having a thickness of 40 nm; transferring the substrate to a vacuum chamber; and vapor-depositing an electron transmission layer (TmPyPb, 50 nm), an electron injection layer (LiF, 0.5-1 nm), and a cathode (Al, 100 nm) to form a complete component.

The process of manufacturing a doped component is the same as that of manufacturing the non-doped component, but further includes several additional steps: preparing solutions of a host material of the light-emitting material and a guest material of the light-emitting material in o-dichlorobenzene (concentration: 12 mg/mL), separately; adding, by a micropipette, 50 uL (5%) of the solution of the guest material into the solution of the host material, and stirring the mixture homogenously by a magnetic stirrer; and then coating the light-emitting layer.

The solution method includes an ink-jet printing method, spin coating, blade coating, screen printing, roll-to-roll printing, and the like. In one embodiment, the solution method of the present disclosure is the ink-jet printing method.

Example 7

Components Manufactured with Vacuum Vapor Deposition Method

Non-doped Components N1 to N8, in which Compounds P1 to P8 are used as light-emitting material respectively, were manufactured and each has a structure: ITO (100 nm)/α-NPD (40 nm)/TCTA (10 nm)/P (40 nm)/TmPyPb (50 nm)/LiF (0.5 nm)/Al (100 nm), and their performances are shown in Table 2.

TABLE 2

Performance of Non-doped Components Manufactured with Vacuum Vapor Deposition Method (Compounds P1 to P8 as Light-Emitting Material)

| Component | $V_{on}$ [V] | $CE_{(10mA/cm^2)}$ (cd A$^{-1}$) | $EQE_{(max)}$ (%) |
|---|---|---|---|
| N1 | 4.76 | 18.2 | 9.8 |
| N2 | 5.27 | 16.8 | 9.4 |
| N3 | 5.25 | 20.4 | 10.2 |
| N4 | 5.30 | 17.5 | 8.2 |
| N5 | 5.32 | 12.5 | 7.2 |
| N6 | 4.95 | 11.8 | 6.5 |
| N7 | 4.98 | 14.2 | 7.8 |
| N8 | 4.56 | 9.8 | 5.8 |

Doped Components $N_9$ to N16, in which Compounds P1 to P8 are used as fluorescent dopant respectively, were manufactured and each has a structure: ITO (100 nm)/α-NPD (40 nm) TCTA (10 nm)/CBP: P (40 nm)/TmPyPb (50 nm)/LiF (0.5 nm)/Al (100 nm). Moreover, as a comparative example, a doped Component C1, in which BCzVBi was used as fluorescent dopant and CBP was used as host material, was manufactured and has a structure: ITO (100 nm)/α-NPD (40 nm)/TCTA (10 nm)/CBP: BCzVBi (40 nm, 5%)/TmPyPb (50 nm)/LiF (0.5 nm)/Al (100 nm). The performances data are shown in Table 3.

TABLE 3

Performance of Doped Components Manufactured with Vacuum Vapor Deposition Method (Compounds P1 to P8 as Fluorescent Dopant)

| Component | $V_{on}$ [V] | $CE_{(10mA/cm^2)}$ (cd A$^{-1}$) | $EQE_{(max)}$ (%) |
|---|---|---|---|
| N9 | 4.89 | 35.1 | 18.9 |
| N10 | 5.35 | 26.9 | 17.8 |
| N11 | 5.18 | 38.4 | 19.5 |
| N12 | 5.02 | 25.7 | 15.2 |
| N13 | 4.96 | 24.0 | 14.5 |
| N14 | 5.45 | 24.8 | 16.2 |
| N15 | 5.34 | 28.4 | 15.3 |
| N16 | 5.20 | 27.4 | 14.0 |
| C1 | 4.8 | 7.2 | 4.8 |

It can be seen from Table 2 and Table 3 that, among the non-doped components, which were manufactured by using Compounds P1 to P8 as light-emitting material with vacuum vapor deposition method, a maximum external quantum efficiency of 10.2% was reached. This indicates that, by introducing benzothiophene group, the interaction between the electron donor D and the electron acceptor A is more intense, the molecular distortion strength is increased and thus a larger dihedral angle is formed, thereby achieving an effective separation HOMO from LUMO and solving a problem about exciton quenching caused by π-π stacking. Meanwhile, a certain rigidity of the molecules can be maintained, and a high photoluminescence quantum yield can be achieved, so as to obtain a component having satisfying performances.

Further, it can be seen from Table 3 that the doped Components N9 to N16 each has a significantly higher $EQE_{(max)}$ than the comparative Component C1, in which a conventional blue light-emitting material BCzVBi was used as fluorescent dopant. This can be attributed to the property of TADF of Compounds P1 to P8. The property of TADF achieves that triplet excitons can emit light to improve the efficiency of the component, which is inhibited in the conventional fluorescent molecules (such as BCzVBi).

Among the doped components, in which Compounds P1 to P8 were used as dopant light-emitting material and mCBP was used as host material, a maximum external quantum efficiency of 19.5% was achieved, which is significantly improved compared with the non-doped components. This indicates that the π-π stacking effect and concentration quenching can be reduced by introducing dopant into the host material.

Doped Components N17 to N18, in which Compound P2 was used as host material and a fluorescent material or a phosphorescent material was used as dopant, were manufactured and each has a structure: ITO (100 nm)/α-NPD (40 nm)/TCTA (10 nm)/P2: dopant (fluorescent material or phosphorescent material) (40 nm)/TmPyPb (50 nm)/LiF (0.5 nm)/Al (100 nm). The fluorescent material is rubrene, and the phosphorescent material is Ir(ppy)3. Their performances are shown in Table 4.

TABLE 4

Performances of Doped Components Manufactured by Vacuum Vapor Deposition Method

| Component | $V_{on}$ [V] | $CE_{(10\ mA/cm^2)}$ (cd A$^{-1}$) | $EQE_{(max)}$ (%) |
|---|---|---|---|
| N17 | 4.84 | 14.6 | 8.6 |
| N18 | 5.20 | 40.3 | 19.4 |

It can be seen from Table 4 that among the doped components, in which the Compound P2 according to the present disclosure was used as the host material, and rubrene and Ir(ppy)3 were used as the dopant material, maximum external quantum efficiencies of 8.6% and 19.4% were achieved. That indicates that the compounds according to the present disclosure can be used as host material of the fluorescent material and the phosphorescent material.

Example 8

Components Manufactured by Solution Method

A corresponding doped Component N19 and a corresponding non-doped Component $N_{20}$ were manufactured by a solution method. The doped Component $N_{19}$ has a structure: ITO (100 nm)/PEDOT: PSS (40 nm)/PVK: P1 (40 nm)/TmPyPb (50 nm)/LiF (0.5 nm)/Al (100 nm).

In the doped Component N19, a conventional polymer PVK was used as host material.

The non-doped Component N20 has a structure: ITO (100 nm)/PEDOT: PSS (40 nm)/P1 (40 nm)/TmPyPb (50 nm)/LiF (0.5 nm)/Al (100 nm).

Relevant data of the above components are shown in Table 5.

TABLE 5

Performances of Components Manufactured by Solution Method

| Component | $V_{on}$ [V] | $CE_{(10\ mA/cm^2)}$ (cd A$^{-1}$) | $EQE_{(max)}$ (%) |
|---|---|---|---|
| N19 | 4.8 | 24.6 | 13.4 |
| N20 | 4.4 | 12.3 | 8.4 |

As shown in Table 5, among the non-doped and doped components manufactured by the solution method, maximum external quantum efficiencies of 8.4% and 13.4% are achieved, respectively. Comparing with the vapor deposition method, the performance is slightly decreased, and the degradation may be caused by residual solvents in the solution method.

What is claimed is:

1. A compound, having a structure represented by Formula (I):

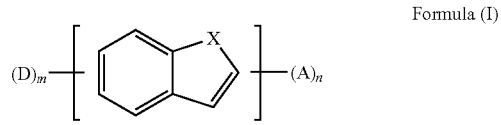

Formula (I)

wherein X is S, O, Se, or -C(Me)$_2$-;

D is a chemical group acting as an electron donor, A is a chemical group acting as an electron acceptor;

m is a number of the electron donors D, and the m electron donors D are the same or different from one another;

n is a number of the electron acceptors A, the n electron acceptors A are the same or different from one another;

m and n are integers each independently selected from 1, 2, 3, 4 or 5, and m+n≤6, and at least two of the m electron donors D and the n electron acceptors A are bonded to the compound represented by the Formula (I) in an ortho-position, wherein the electron acceptor A is selected from a group consisting of nitrogenous heterocyclic substituent, triaryl boron substituent, benzophenone substituent, aromatic heterocyclic ketone substituent, and sulfone substituent; or the electron acceptor A is any one of following chemical groups;

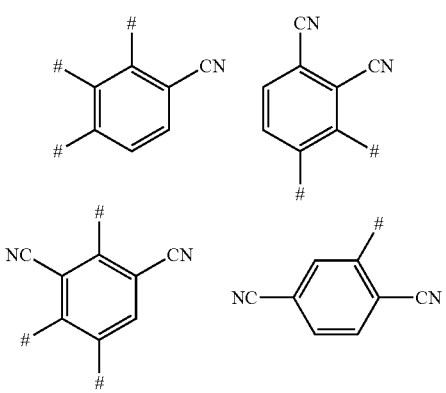

57
-continued
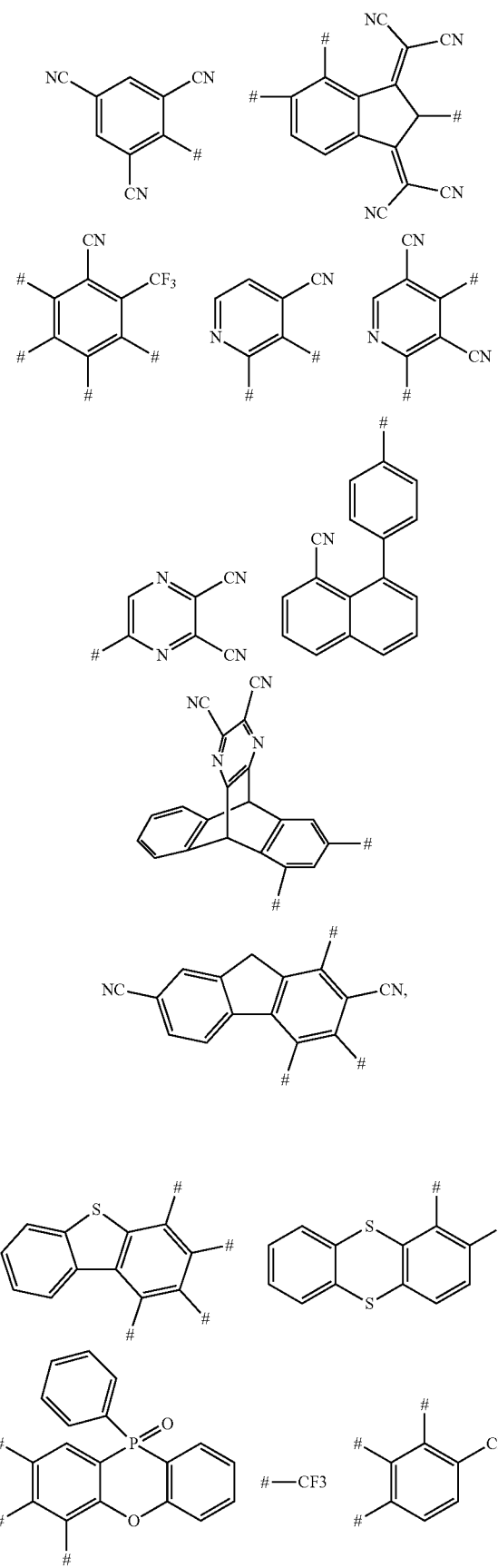
58
-continued
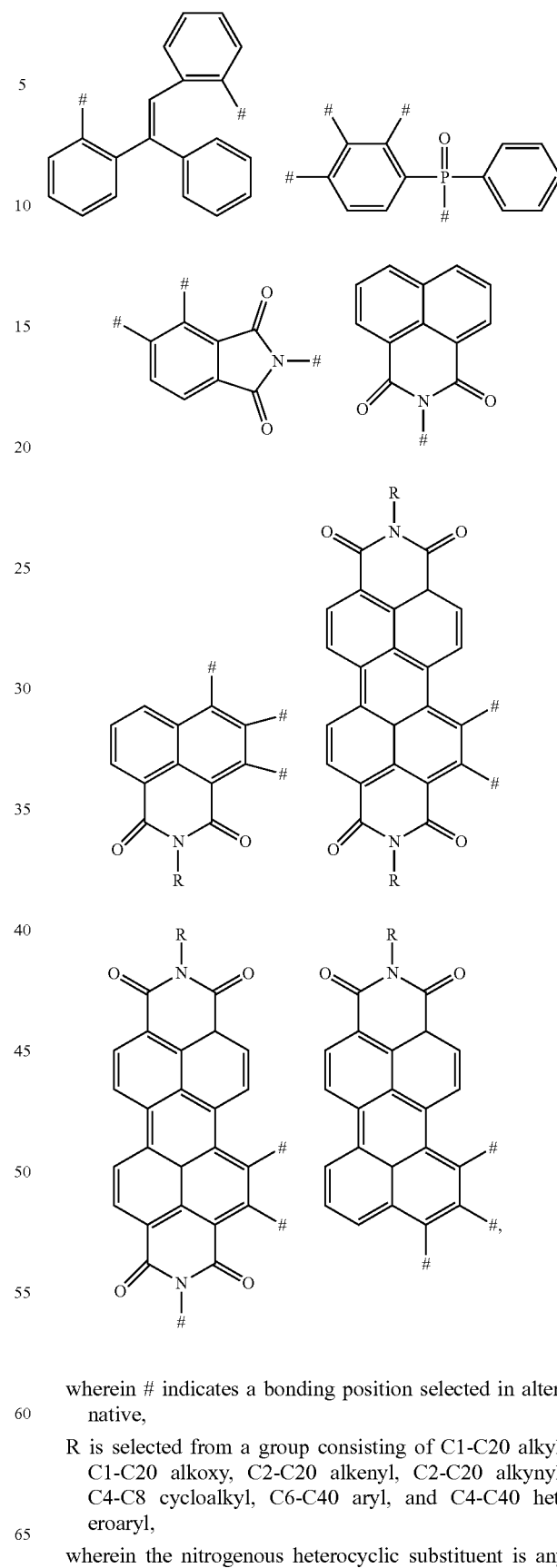
wherein # indicates a bonding position selected in alternative,
R is selected from a group consisting of C1-C20 alkyl, C1-C20 alkoxy, C2-C20 alkenyl, C2-C20 alkynyl, C4-C8 cycloalkyl, C6-C40 aryl, and C4-C40 heteroaryl,
wherein the nitrogenous heterocyclic substituent is any one of following chemical groups;

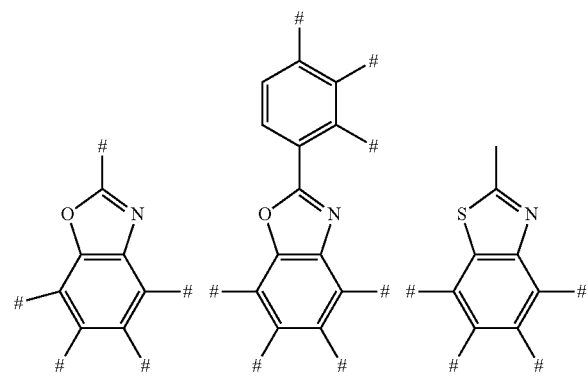
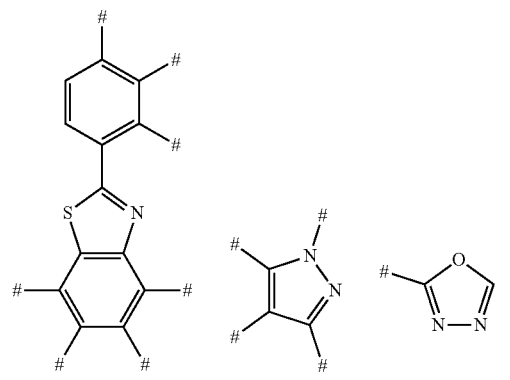
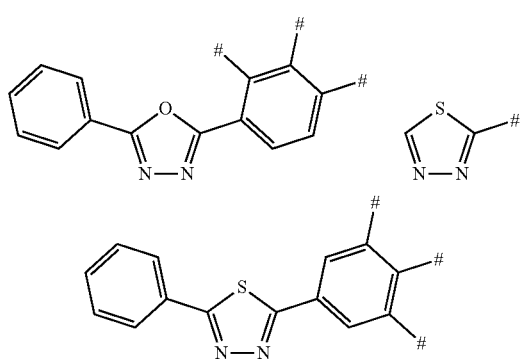
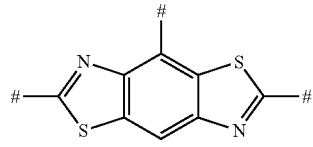
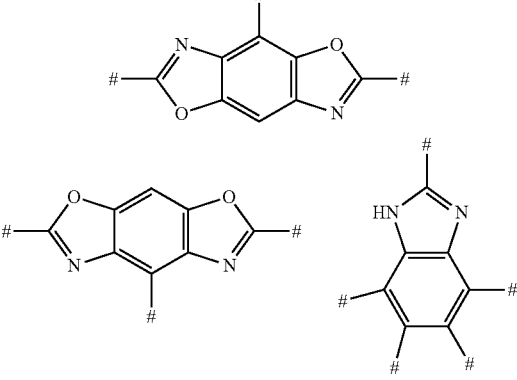
-continued
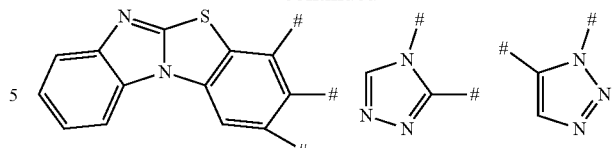
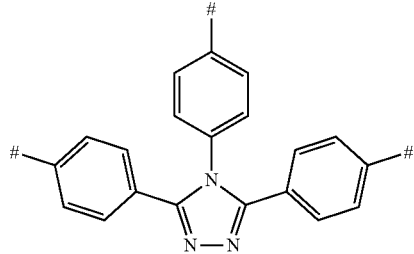
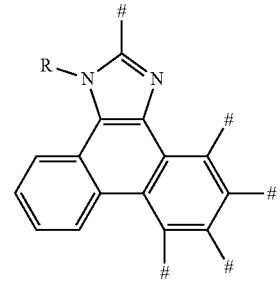
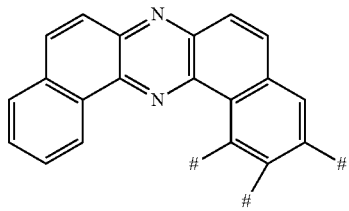
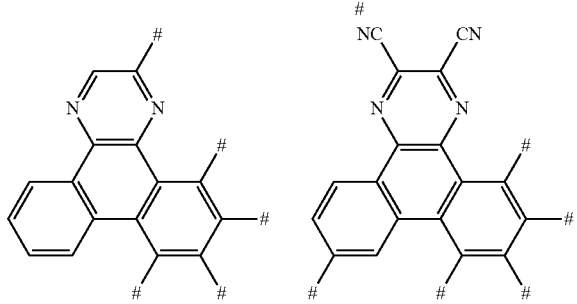
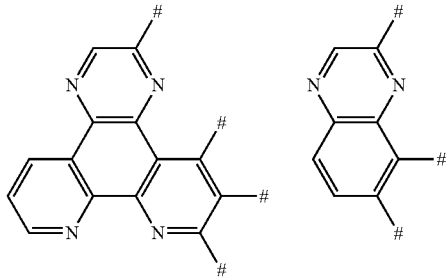
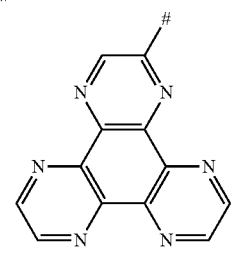

-continued
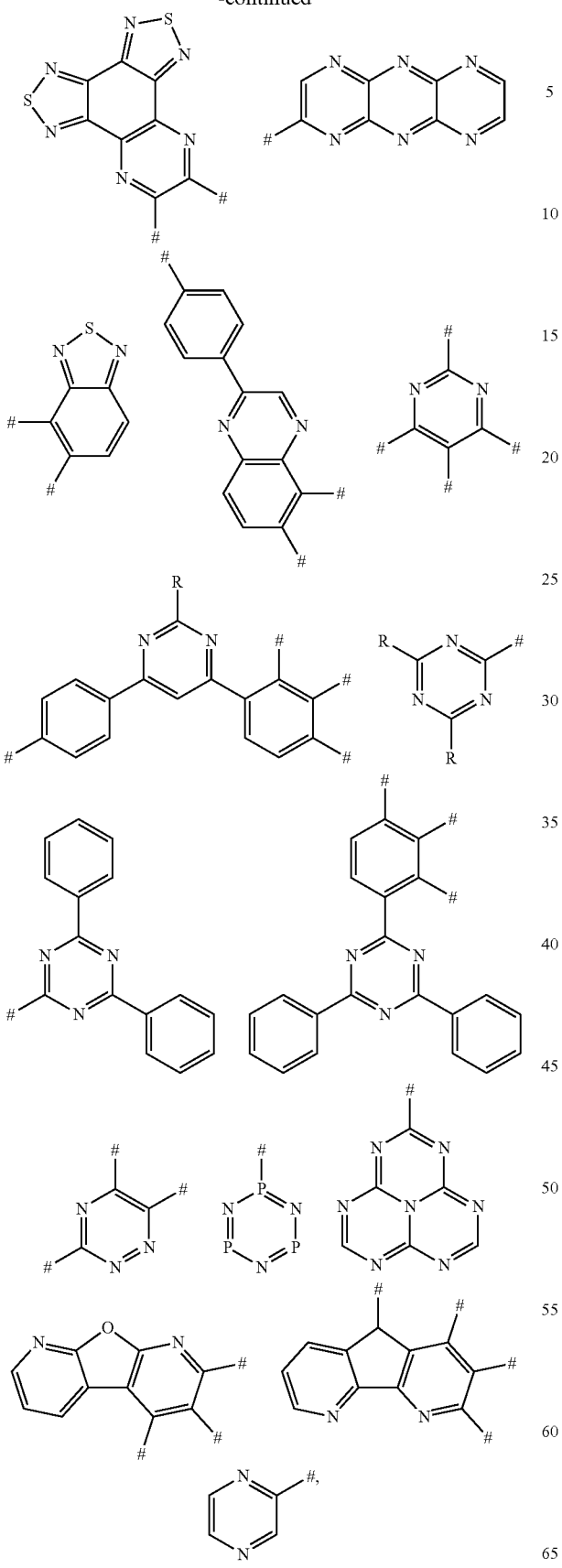
wherein # indicates a bonding position selected in alternative; and
R' is selected from a group consisting of hydrogen, C1-C20 alkyl, C1-C20 alkoxy, C4-C8 cycloalkyl, C6-C40 aryl, and C4-C40 heteroaryl.
2. The compound according to claim 1, wherein the electron donor D is any one of following chemical groups:
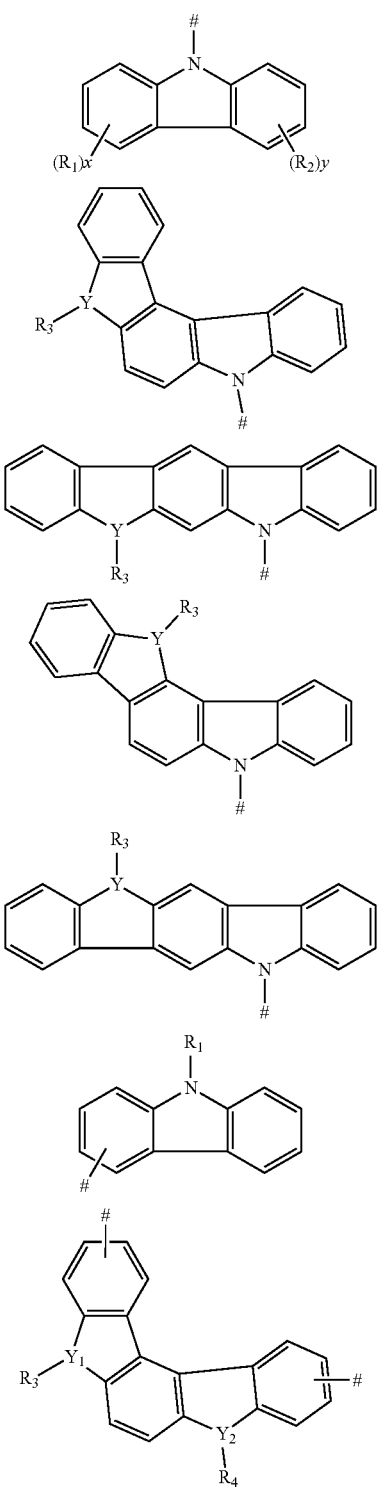

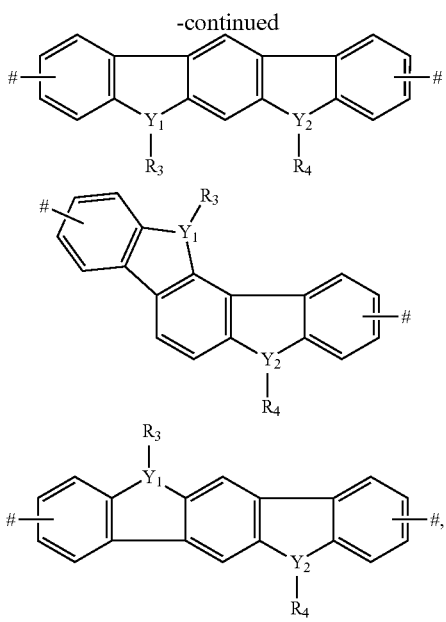

wherein Y, Y$_1$ and Y$_2$ are each independently selected from a group consisting of nitrogen, oxygen, and sulfur;

x and y are integers each independently selected from 0, 1, 2 or 3;

# indicates a bonding position selected in alternative;

when Y is oxygen or sulfur, R$_3$ is absent;

when Y$_1$ is oxygen or sulfur, R$_3$ is absent;

when Y$_2$ is oxygen or sulfur, R$_4$ is absent; and

R$_1$, R$_2$, R$_3$ and R$_4$ are each independently selected from a group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl, substituted or unsubstituted C12-C40 diphenylamino, substituted or unsubstituted C3-C40 azine group, and groups represented by Formula (21):

Formula (21)

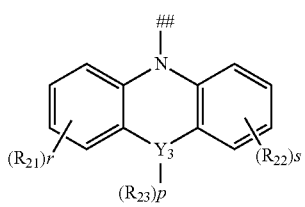

wherein Y$_3$ is selected from a group consisting of carbon, nitrogen, oxygen, sulfur, and silicon;

R$_{21}$, R$_{22}$ and R$_{23}$ are each independently selected from a group consisting of hydrogen, C1-C20 alkyl, C1-C20 alkoxy, substituted or unsubstituted C6-C40 aryl, and substituted or unsubstituted C4-C40 heteroaryl;

r and s are integers each independently selected from 0, 1, 2 or 3, and p is 0, 1 or 2;

when Y$_3$ is oxygen or sulfur, p=0; and indicates a bonding position.

3. The compound according to claim 2, wherein the electron donor D is any one of following chemical groups:

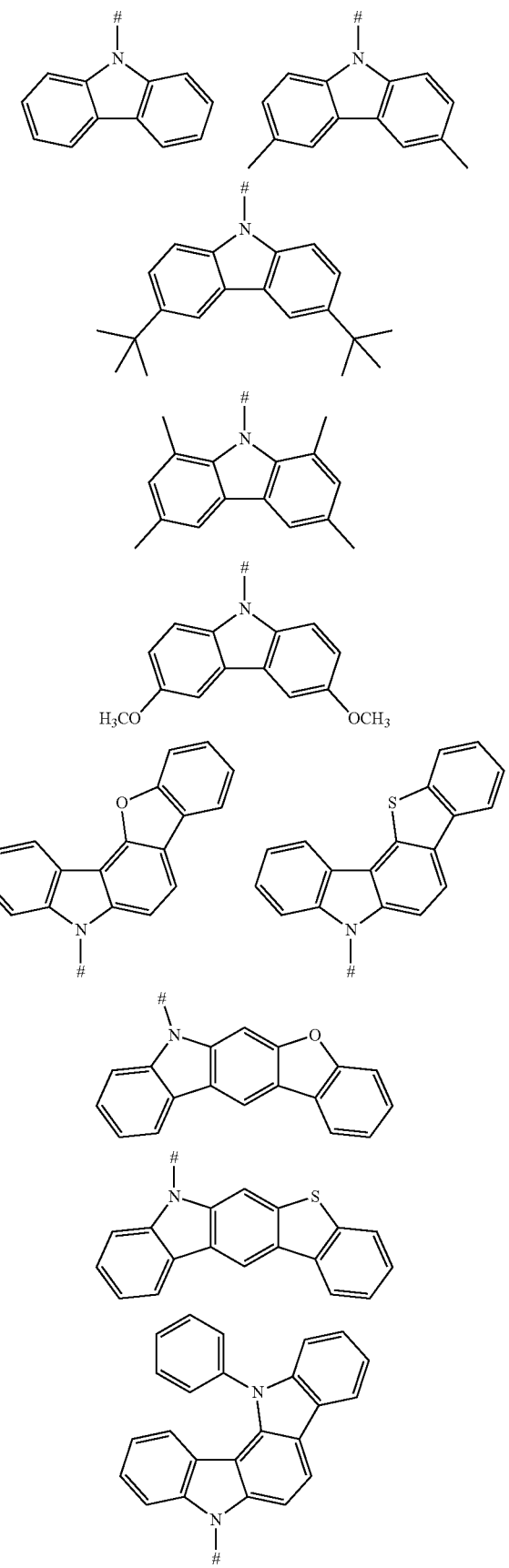

-continued
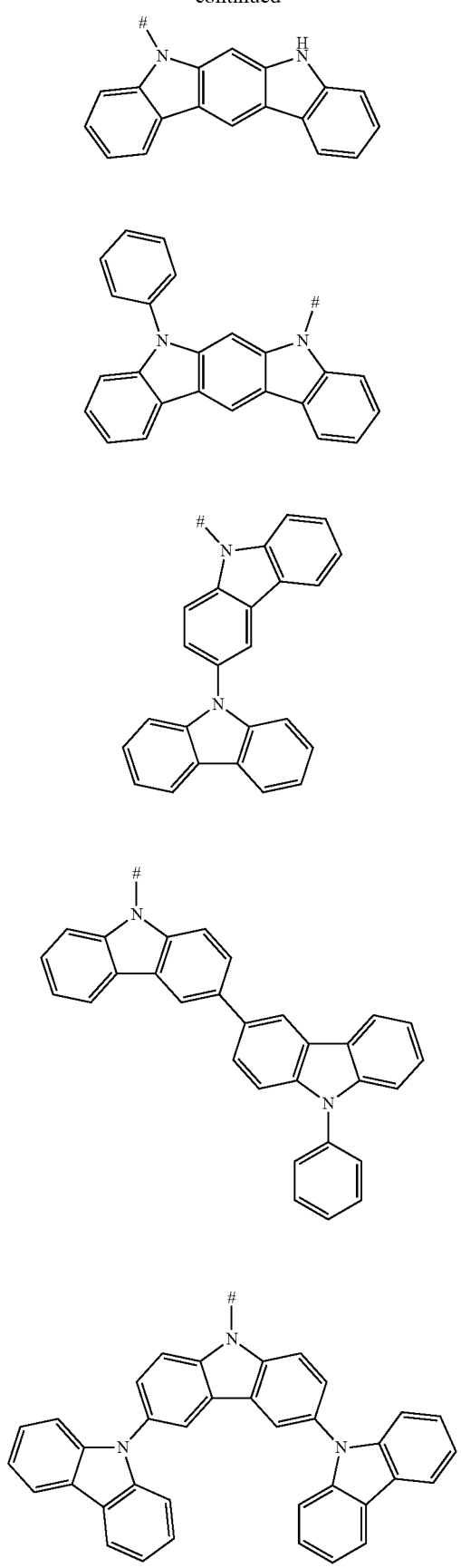
-continued
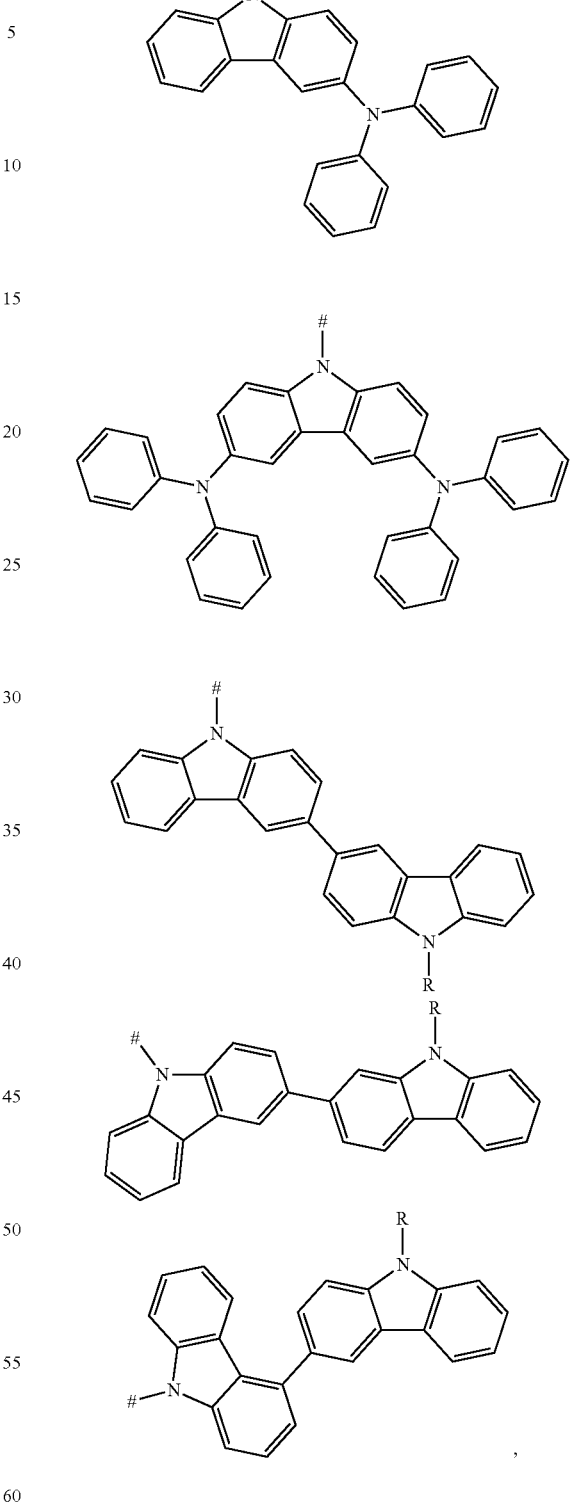
wherein R is selected from a group consisting of C1-C20 alkyl, C1-C20 alkoxy, C2-C20 alkenyl, C2-C20 alkynyl, C6-C40 aryl, and C4-C40 heteroaryl; and
# indicates a bonding position selected in alternative.
4. The compound according to claim 1, wherein the electron donor D is any one of following chemical groups:

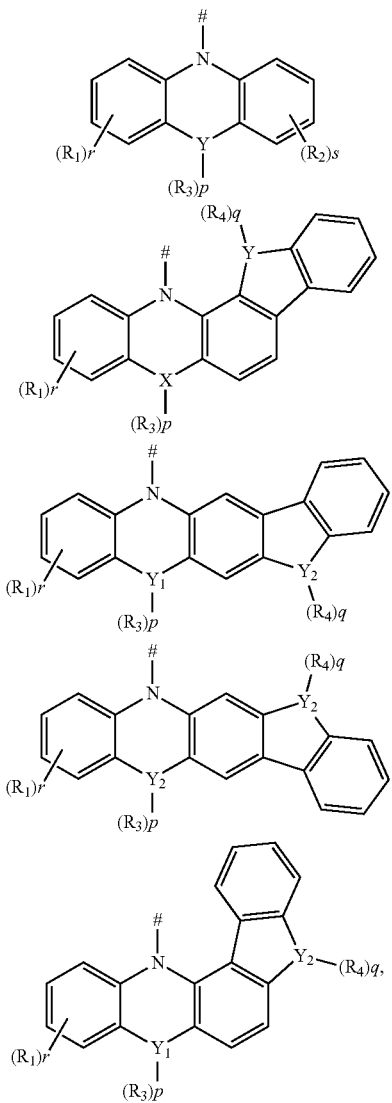

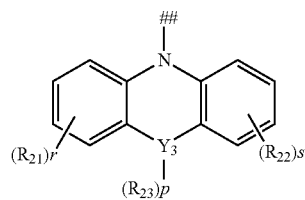

Formula (21)

wherein $Y_3$ is selected from a group consisting of carbon, nitrogen, oxygen, sulfur, and silicon;

$R_{21}$, $R_{22}$ and $R_{23}$ are each independently selected from a group consisting of hydrogen, C1-C20 alkyl, C1-C20 alkoxy, substituted or unsubstituted C6-C40 aryl, and substituted or unsubstituted C4-C40 heteroaryl;

r and s are integers each independently selected from 0, 1, 2 or 3, and p is 0, 1 or 2;

when $Y_3$ is oxygen or sulfur, p=0; and indicates a bonding position.

5. The compound according to claim 4, wherein the electron donor D is any one of following chemical groups:

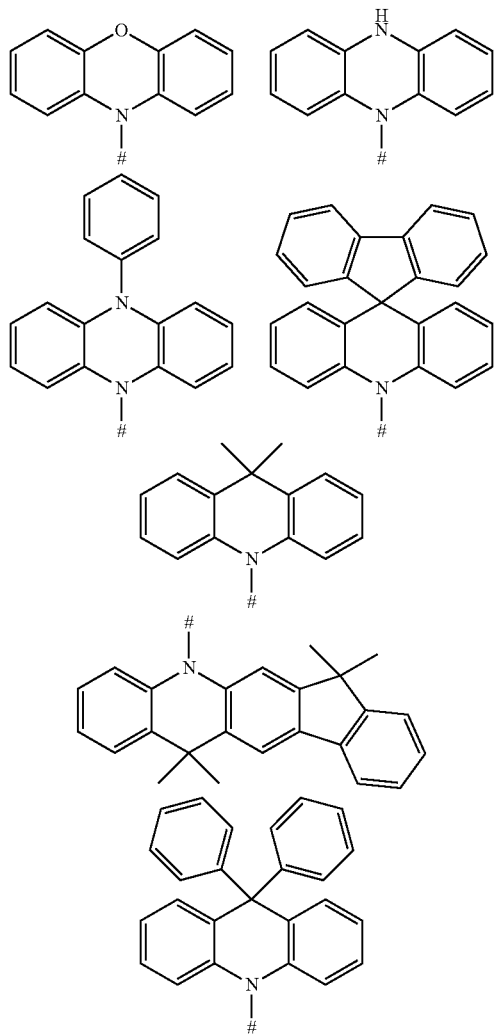

wherein Y, $Y_1$ and $Y_2$ are each independently selected from a group consisting of carbon, nitrogen, oxygen, sulfur, and silicon;

# indicates a bonding position;

r and s are integers each independently selected from 0, 1, 2 or 3, and p and q are integers each independently selected from 0, 1 or 2;

when Y is oxygen or sulfur, p=0 or q=0;

when Y is a nitrogen atom, p and q are each independently 1;

when Y is a carbon atom or a silicon atom, p and q are each independently 2; and $R_1$, $R_2$, $R_3$ and $R_4$ are each independently selected from a group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl, substituted or unsubstituted C12-C40 diphenylamino, substituted or unsubstituted C3-C40 azine group, and groups represented by formula (21):

-continued

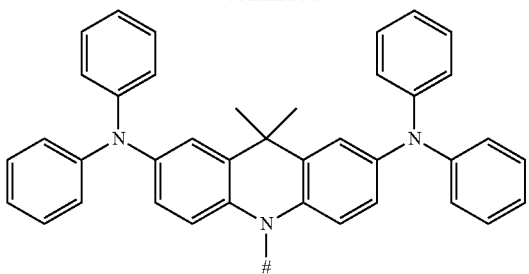

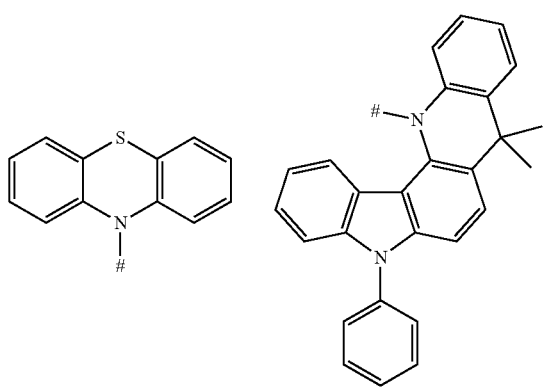

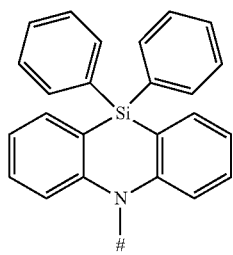

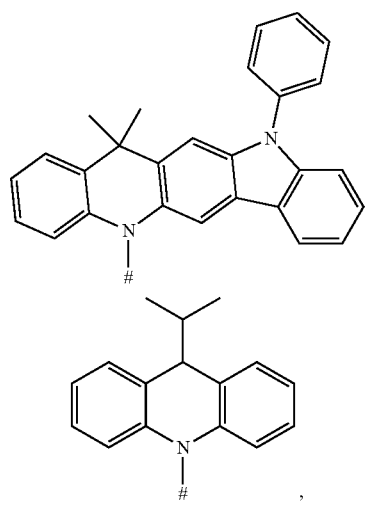

wherein # indicates a bonding position.

6. The compound according to claim 1, wherein the electron donor D is any one of following chemical groups:

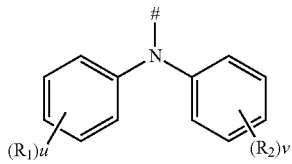

# indicates a bonding position;

u and v are integers each independently selected from 0, 1, 2 or 3;

$R_1$ and $R_2$ are each independently selected from a group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl, substituted or unsubstituted C12-C40 diphenylamino, substituted or unsubstituted C3-C40 azine group, and groups represented by formula (21):

Formula (21)

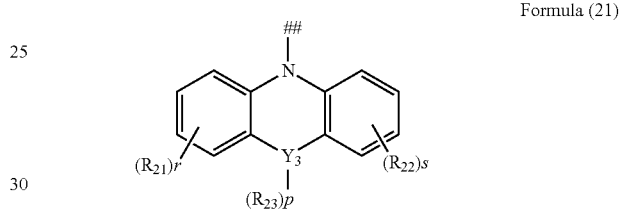

wherein $Y_3$ is selected from a group consisting of carbon, nitrogen, oxygen, sulfur, and silicon;

$R_{21}$, $R_{22}$ and $R_{23}$ are each independently selected from a group consisting of hydrogen, C1-C20 alkyl, C1-C20 alkoxy, substituted or unsubstituted C6-C40 aryl, and substituted or unsubstituted C4-C40 heteroaryl;

r and s are integers each independently selected from 0, 1, 2 or 3, and p is 0, 1 or 2;

when $Y_3$ is oxygen or sulfur, p=0; and indicates a bonding position.

7. The compound according to claim 6, wherein the electron donor D is any one of following chemical groups:

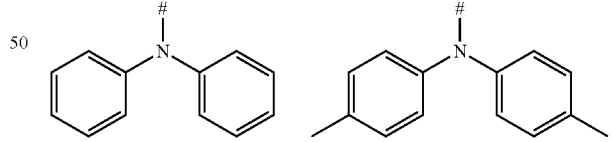

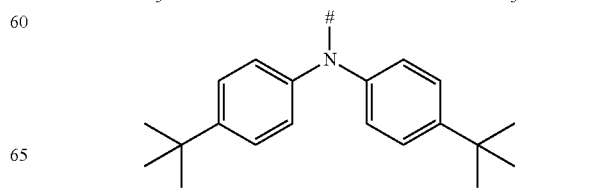

-continued
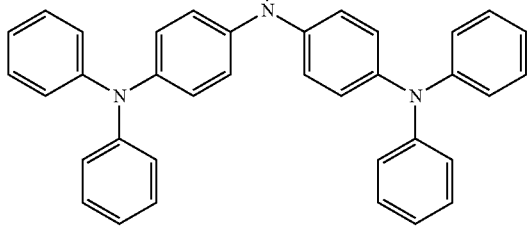
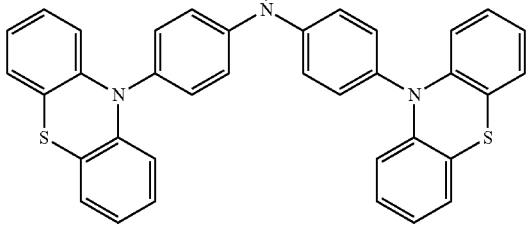
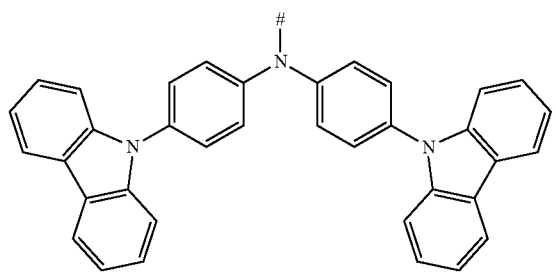
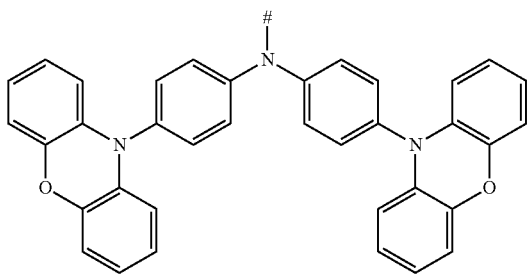
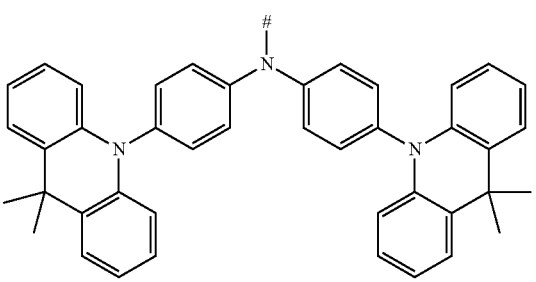
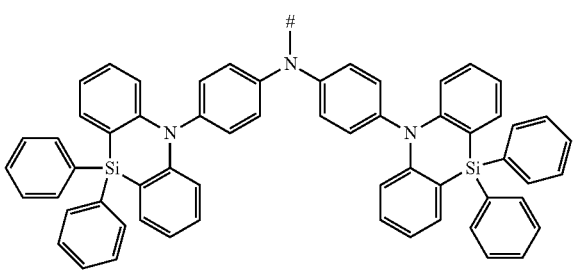
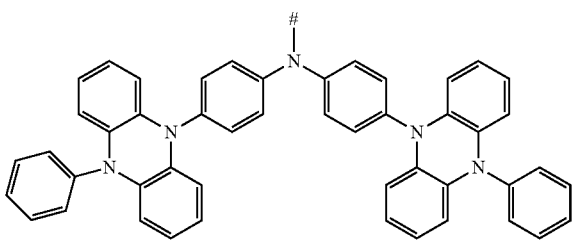
wherein # indicates a bonding position.
8. The compound according to claim 1, wherein the electron donor D is any one of following chemical groups:
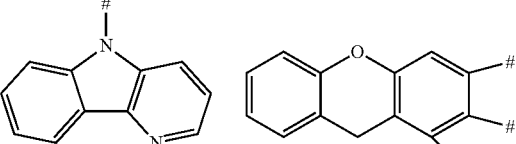
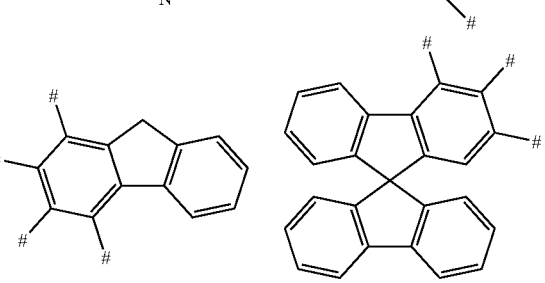
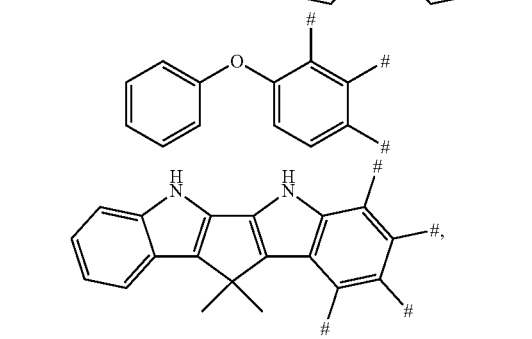
wherein # indicates a bonding position selected in alternative.
9. The compound according to claim 1, wherein the triaryl boron substituent is any one of following chemical groups:
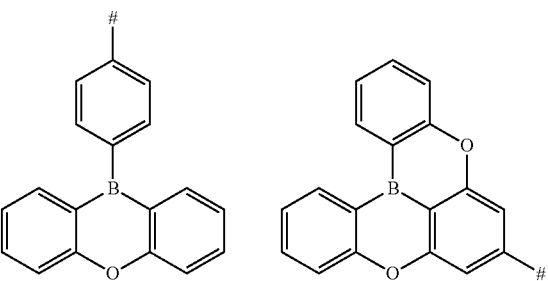

-continued
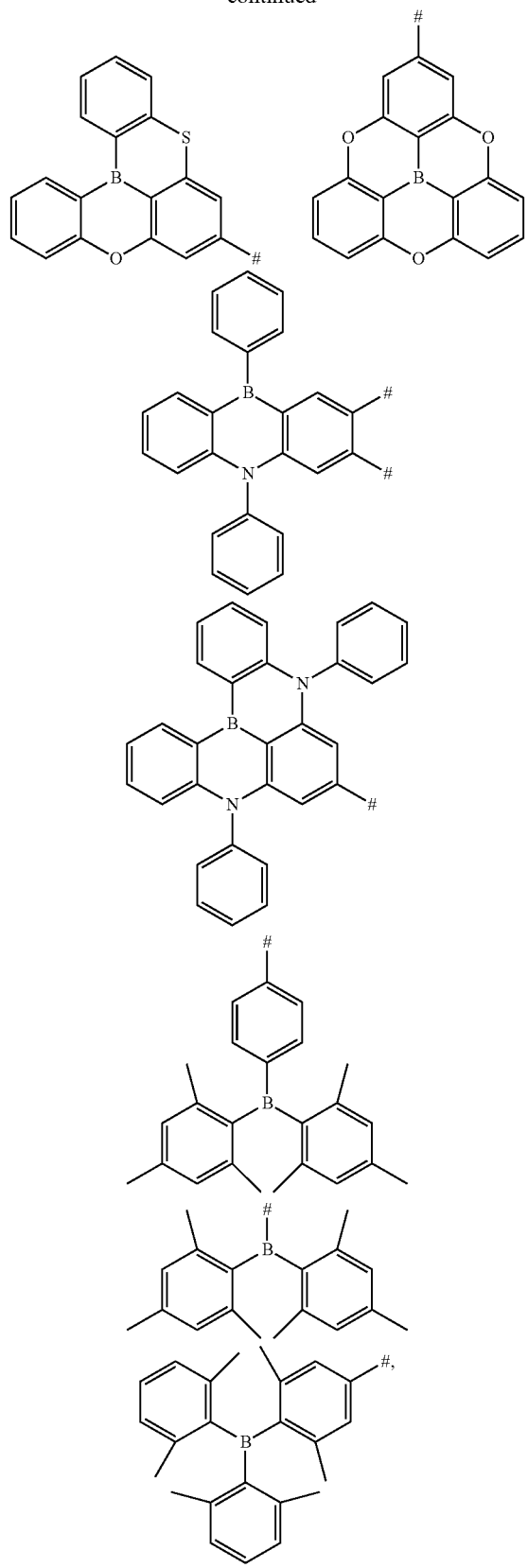
wherein # indicates a bonding position selected in alternative.
10. The compound according to claim 1, wherein the benzophenone substituent and the aromatic heterocyclic ketone substituent are each any one of following chemical groups:
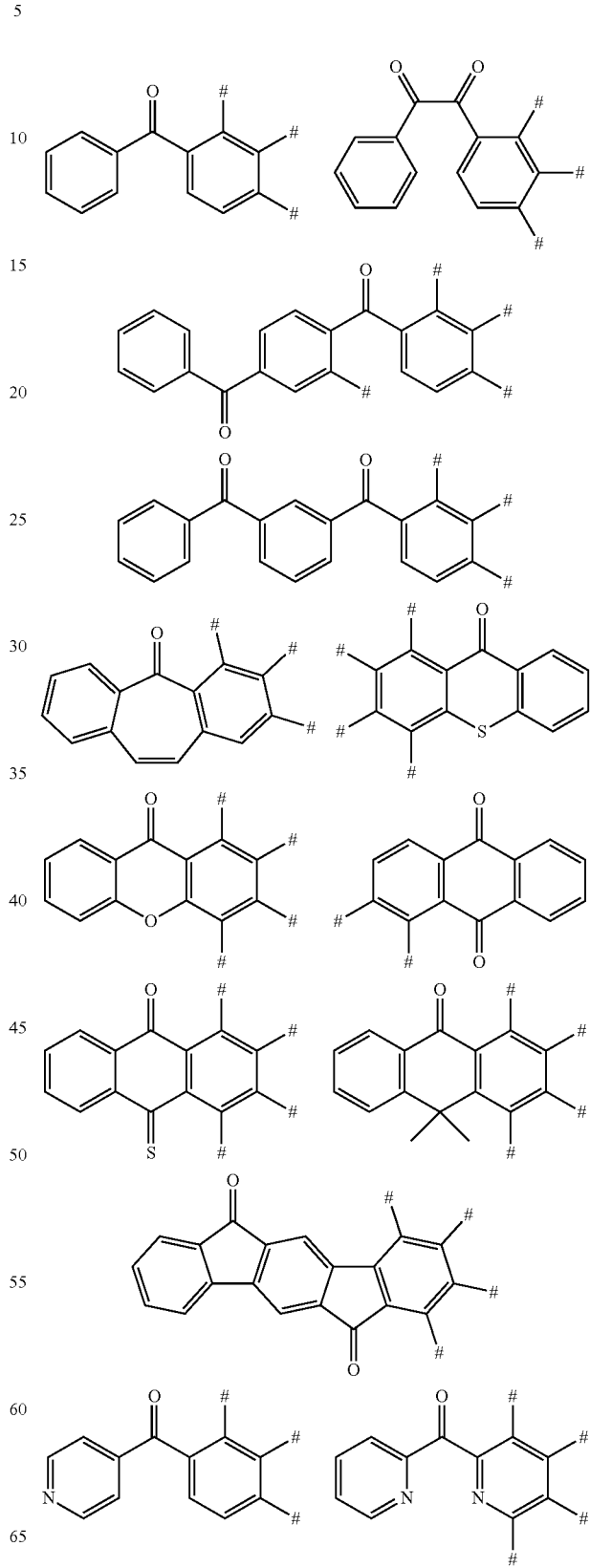

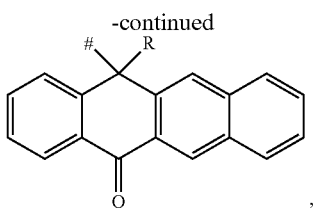

wherein # indicates a bonding position selected in alternative; and

R is selected from a group consisting of C1-C20 alkyl, C1-C20 alkoxy, C2-C20 alkenyl, C2-C20 alkynyl, C4-C8 cycloalkyl, C6-C40 aryl, and C4-C40 heteroaryl.

11. The compound according to claim 1, wherein the sulfone substituent is any one of following chemical groups:

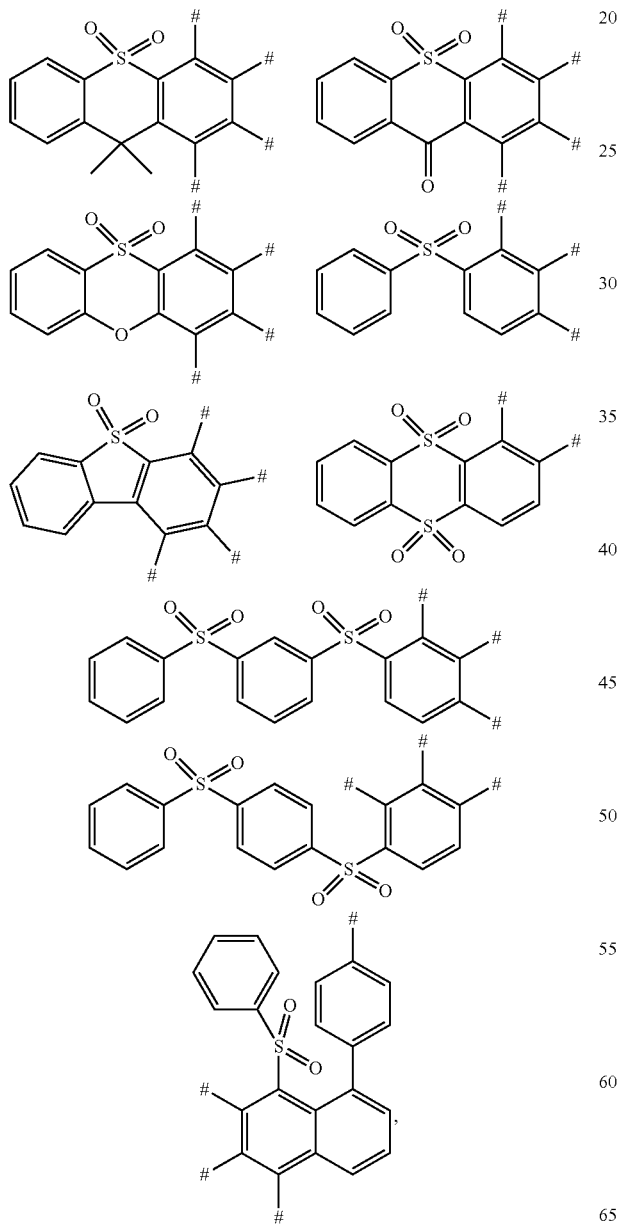

wherein # indicates a bonding position selected in alternative.

12. The compound according to claim 1, wherein an energy difference $\Delta E_{st}$ between a lowest singlet energy level S1 of the compound and a lowest triplet energy level T1 of the compound satisfies an equation $\Delta E_{st} = E_{S1} - E_{T1} \leq 0.30$ eV.

13. An organic light-emitting display device, comprising
an anode;
a cathode; and
a light-emitting layer disposed between the anode and the cathode, wherein a light-emitting material of the light-emitting layer comprises a host material and/or a guest material selected from a group consisting of compounds according to claim 1, and combinations thereof.

14. The organic light-emitting display device according to claim 13, wherein when the light-emitting material of the light-emitting layer is a red light-emitting material, the red light-emitting material has a singlet energy level of 1.61-1.99 eV;

when the light-emitting material of the light-emitting layer is a green light-emitting material, the green light-emitting material has a singlet energy level of 2.15-2.52 eV; and when the light-emitting material of the light-emitting layer is a blue light-emitting material, the blue light-emitting material has a singlet energy level of 2.52-2.73 eV.

15. The organic light-emitting display device according to claim 13, wherein the light-emitting layer comprises the host material and the guest material, a singlet energy level of the host material is higher than a singlet energy level of the guest material, and an energy difference between the singlet energy level of the host material and the singlet energy level of the guest material is less than 1.0 eV, the host material is selected from a group consisting of compounds according to claim 1, and combinations thereof, the guest material is selected from a group consisting of fluorescent material, thermally activated delayed fluorescent material, and phosphorescent material, and an energy difference between a HOMO energy level of the host material and a HOMO energy level of the guest material is less than 0.6 eV, or an energy difference between a LUMO energy level of the host material and a LUMO energy level of the guest material is less than 0.6 eV.

16. A compound being any one of following compounds:

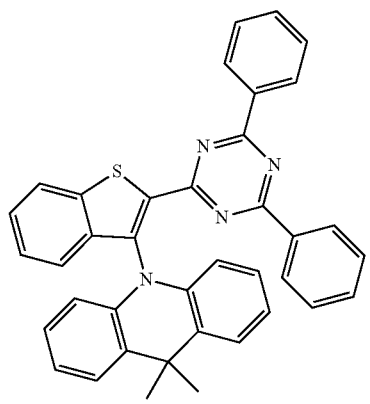

P1

P2
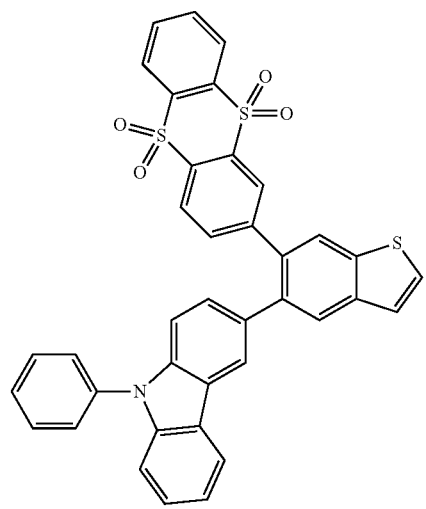
P3
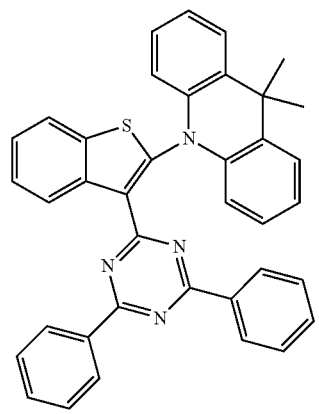
P4
P5
P6
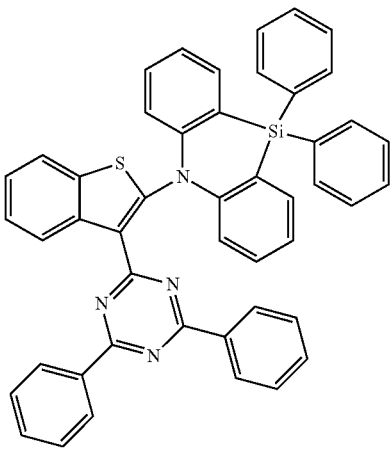
P7
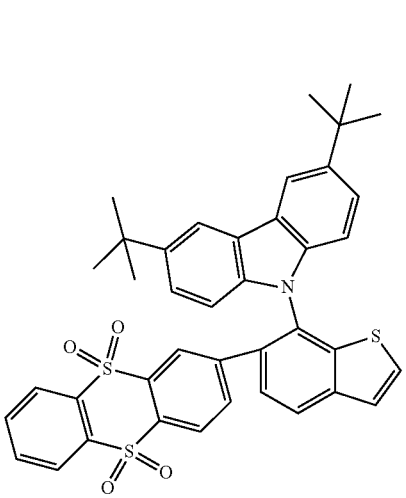
P8
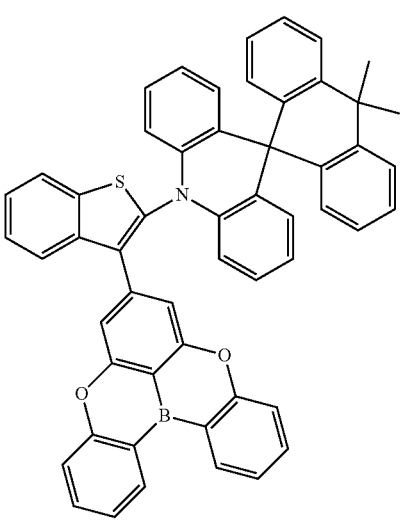

P9
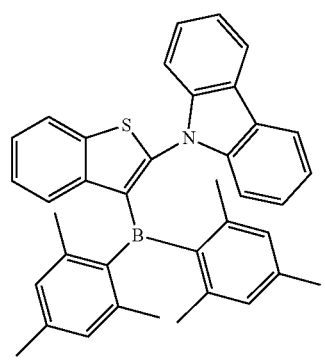
P10
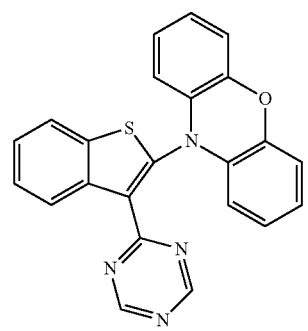
P15
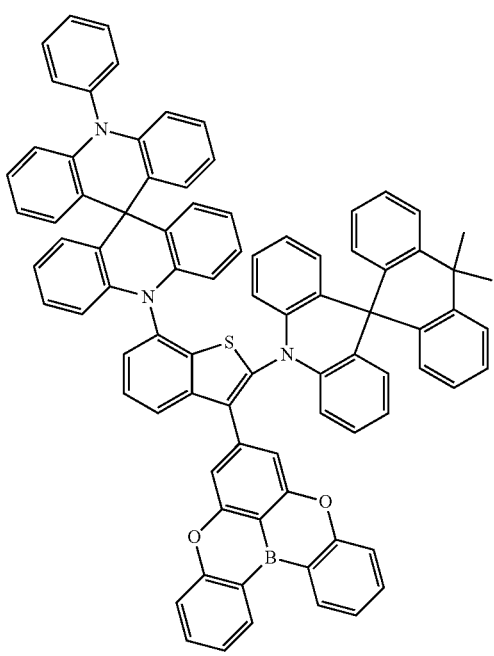
P11
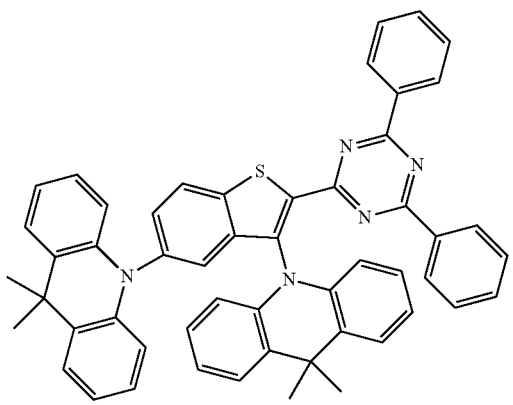
P12
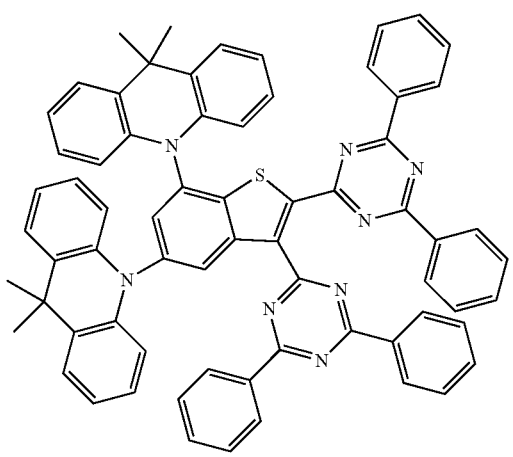
P13
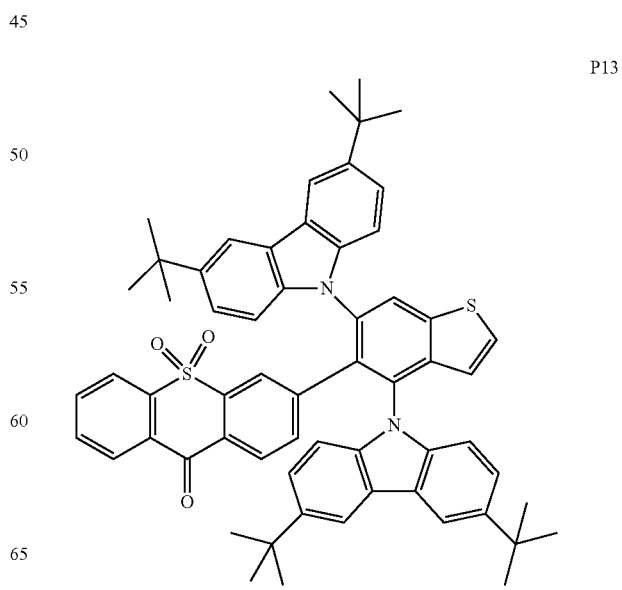

-continued
P14
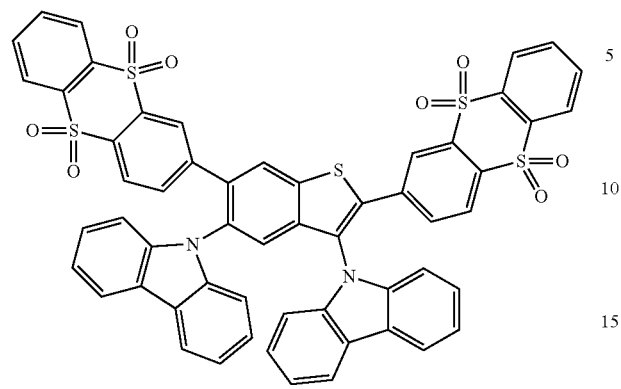
P16
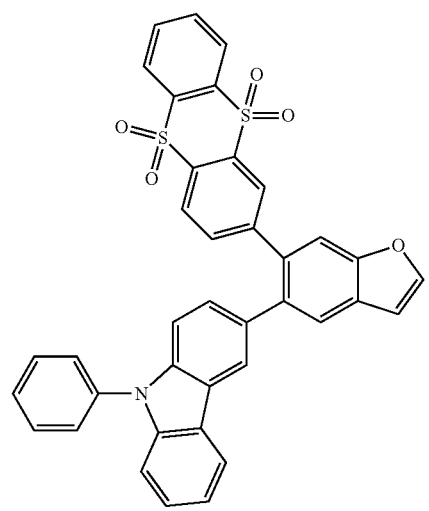
P17
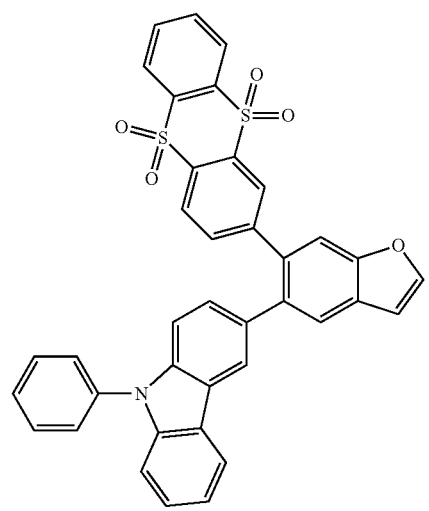
-continued
P18
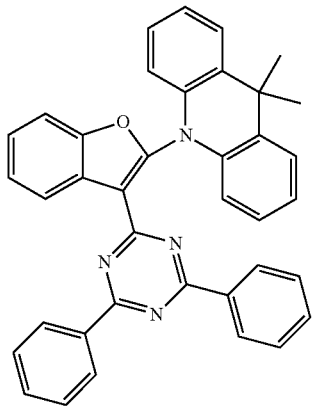
P19
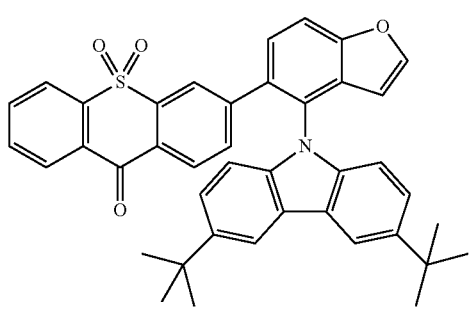
P20
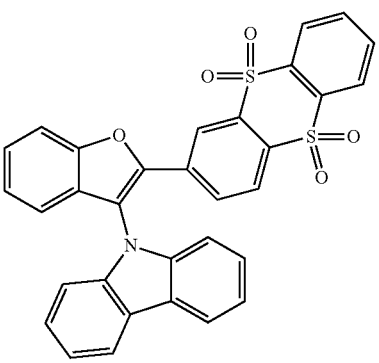
P21
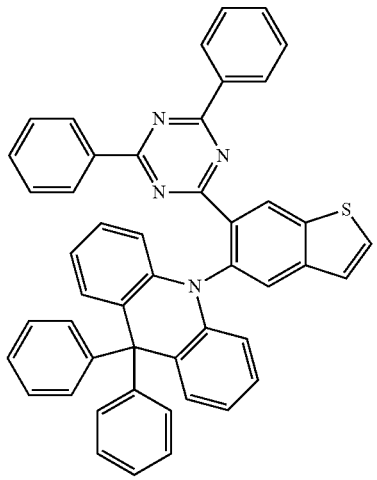

P22 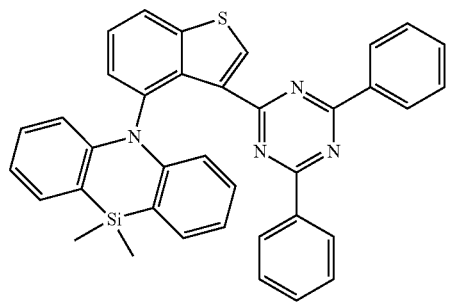
P23 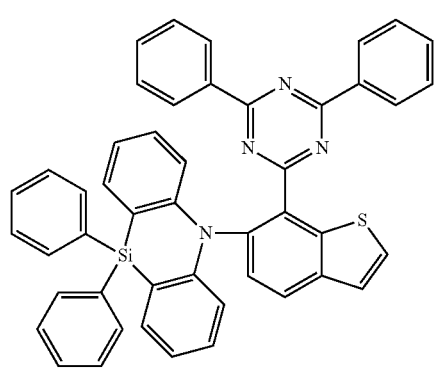
P24 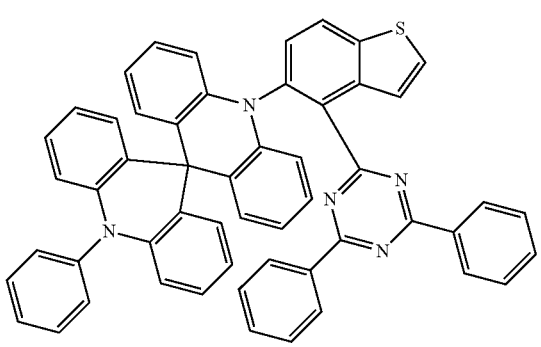
P25 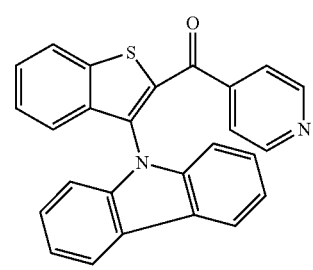
P26 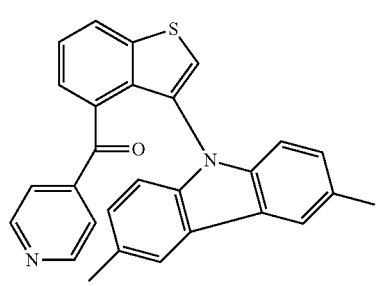
P27 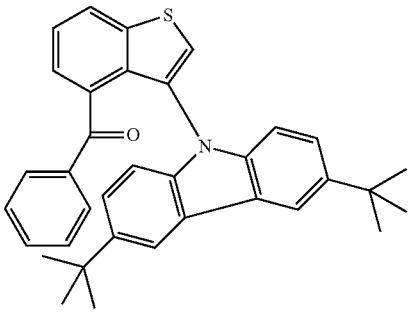
P28 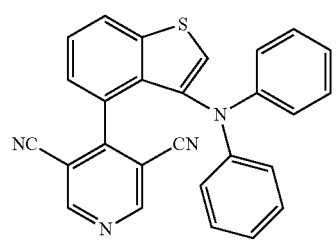
P29 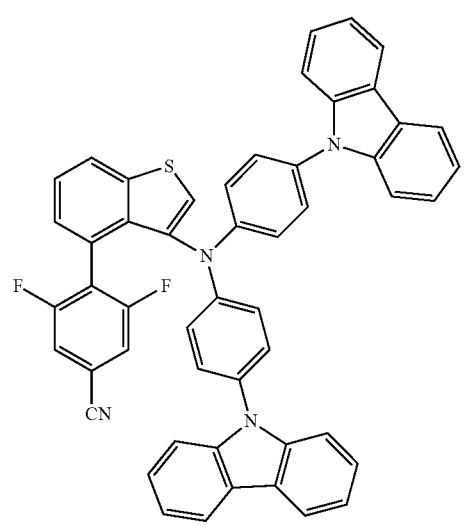
P30 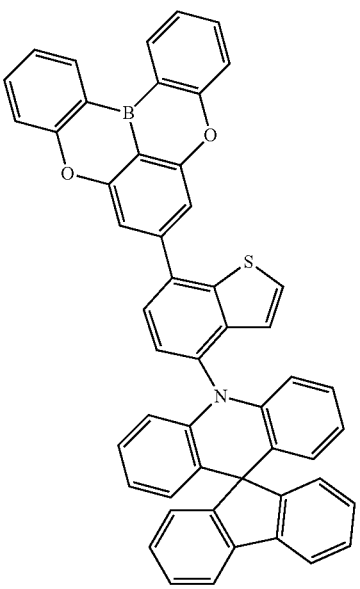

-continued
P31
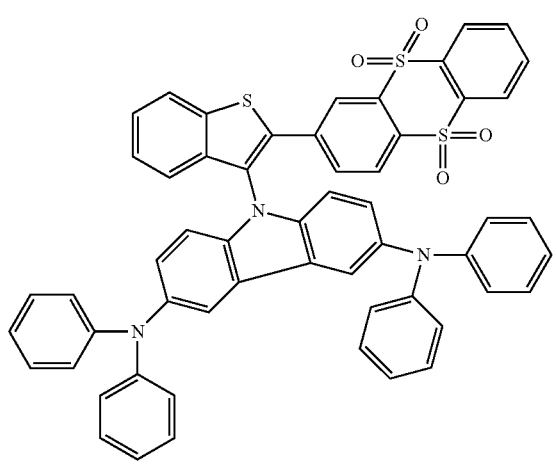
P32
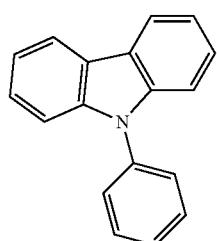
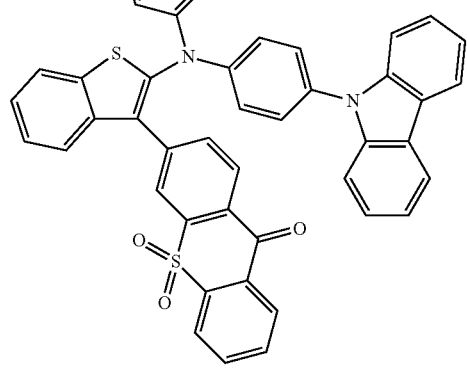
P33
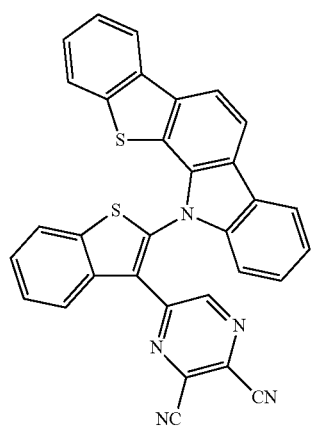
P34
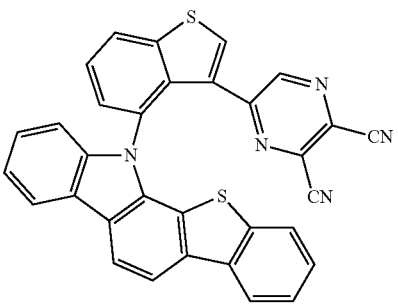
P35
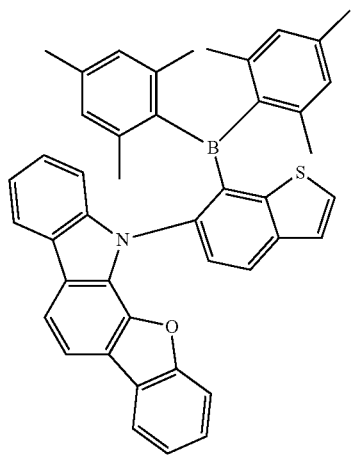
P36
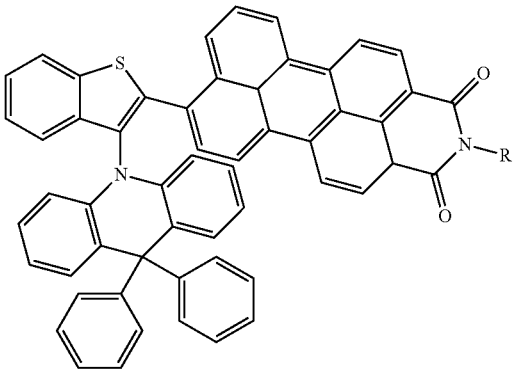
P37
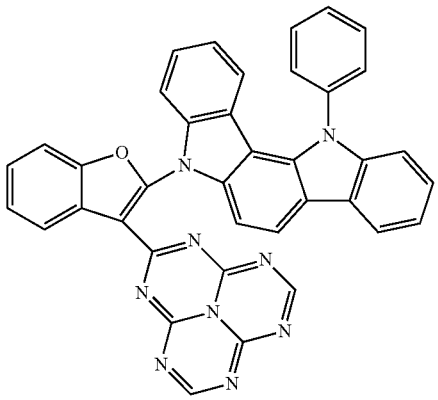

P38
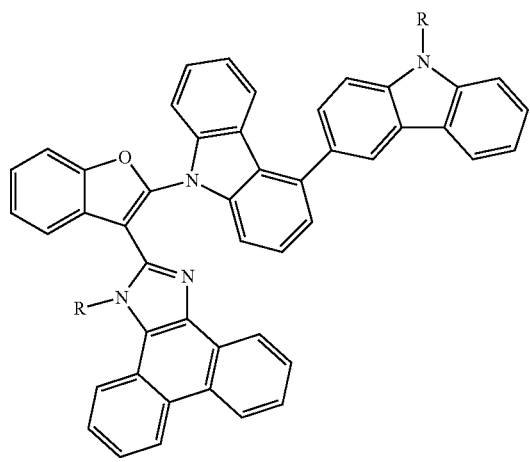
P39
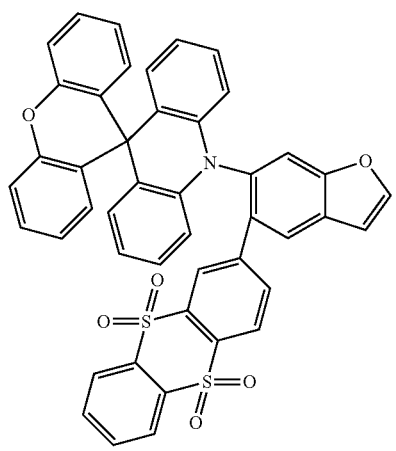
P40
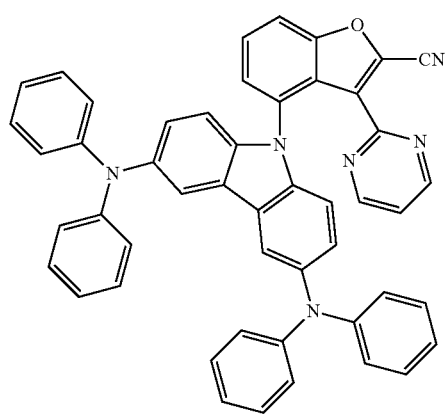
P41
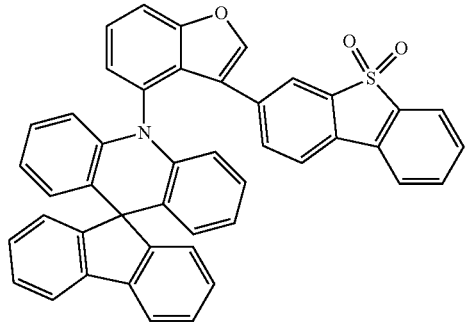
P42
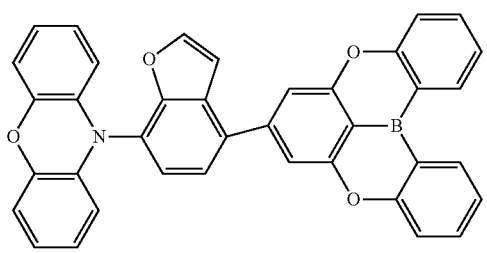
P43
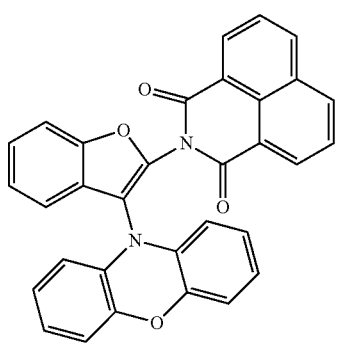
P44
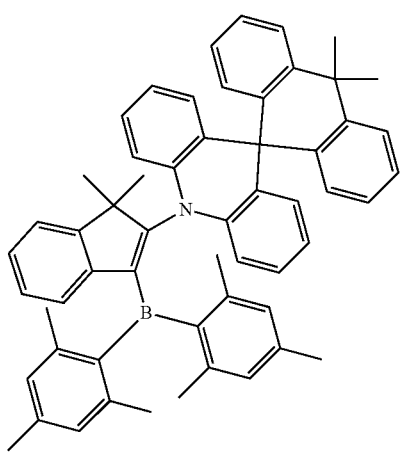

P45
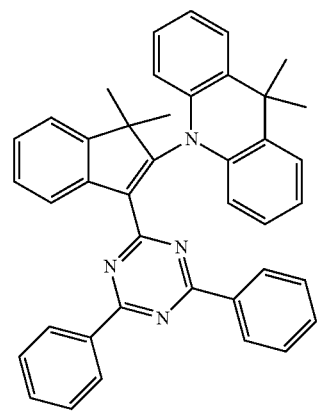
P46
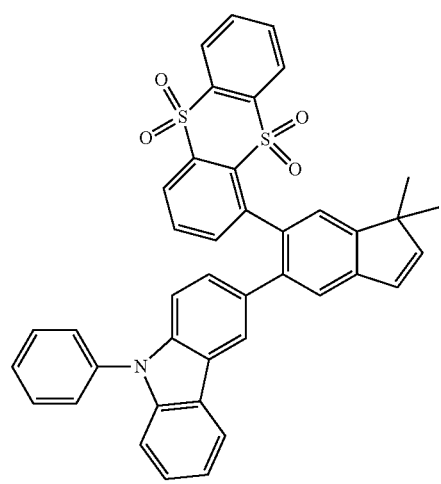
P47
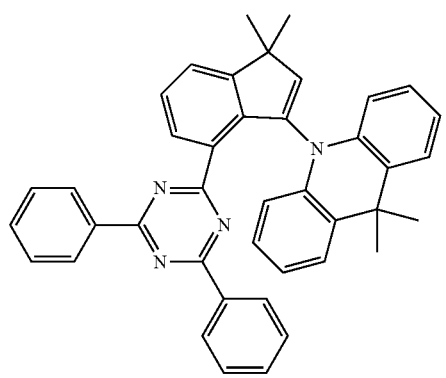
P48
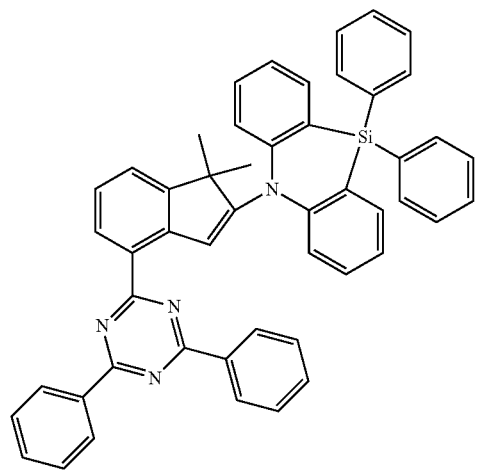
P49
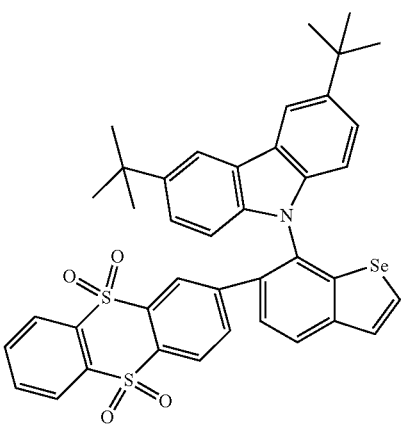
P50
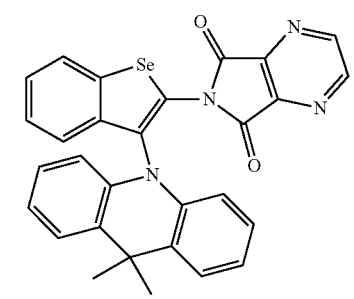
P51
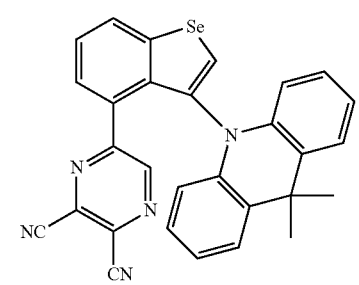

-continued
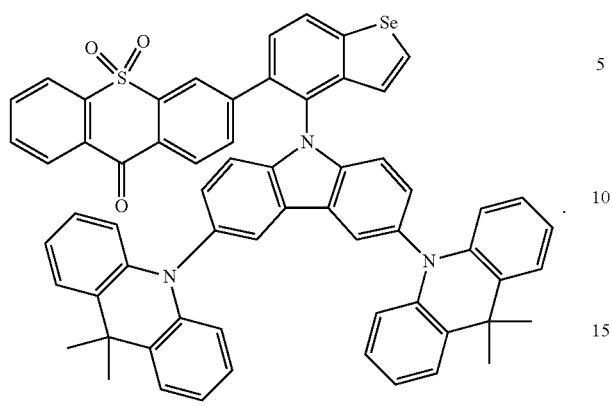
P52
* * * * *